United States Patent
Cotter et al.

(10) Patent No.: US 8,142,460 B2
(45) Date of Patent: Mar. 27, 2012

(54) BONE ABRADING ULTRASONIC HORNS

(75) Inventors: Daniel J. Cotter, North Easton, MA (US); Maria Benson, West Boylston, MA (US); Matthew Shinopulos, Burlington, MA (US); James P. O'Connor, Billerica, MA (US); Amin Kassam, Ottawa, CA (US)

(73) Assignee: Integra LifeSciences (Ireland) Ltd., Dublin (IE)

( * ) Notice: Subject to any disclaimer, the term of this patent is extended or adjusted under 35 U.S.C. 154(b) by 1008 days.

(21) Appl. No.: 11/404,981

(22) Filed: Apr. 14, 2006

(65) Prior Publication Data

US 2006/0235305 A1    Oct. 19, 2006

Related U.S. Application Data

(60) Provisional application No. 60/748,826, filed on Dec. 9, 2005, provisional application No. 60/671,739, filed on Apr. 15, 2005.

(51) Int. Cl.
*A61B 17/32* (2006.01)
(52) U.S. Cl. .................................................. 606/169
(58) Field of Classification Search .......... 433/118–119; 606/169–170; 604/22
See application file for complete search history.

(56) References Cited

U.S. PATENT DOCUMENTS

| RE25,033 | E | * | 8/1961 | Balamuth et al. ............... 451/36 |
| 4,063,557 | A | | 12/1977 | Wuchinich et al. |
| 4,223,676 | A | | 9/1980 | Wuchinich et al. |
| 4,425,115 | A | | 1/1984 | Wuchinich |
| 4,643,717 | A | * | 2/1987 | Cook et al. ...................... 604/22 |
| 4,750,488 | A | | 6/1988 | Wuchinich et al. |
| 4,750,901 | A | | 6/1988 | Molteno |
| 4,827,911 | A | | 5/1989 | Broadwin et al. |
| 4,922,902 | A | | 5/1990 | Wuchinich et al. |
| 4,931,047 | A | | 6/1990 | Broadwin et al. |
| 5,015,227 | A | | 5/1991 | Broadwin et al. |
| 5,989,208 | A | * | 11/1999 | Nita ................................ 604/22 |
| 6,214,017 | B1 | | 4/2001 | Stoddard et al. |
| 6,450,975 | B1 | * | 9/2002 | Brennan et al. ............... 600/585 |
| 6,910,889 | B1 | * | 6/2005 | Hickok .......................... 433/119 |

OTHER PUBLICATIONS

Integra Radionics, *2006 CUSA Excel Ultrasonic Surgical Aspirator Product Catalog*, 2006, 15 pages, Burlington, Massachusetts.

* cited by examiner

*Primary Examiner* — Ryan Severson
*Assistant Examiner* — Ashley Cronin
(74) *Attorney, Agent, or Firm* — Thomas A. Runk; Fulwider Patton LLP

(57) ABSTRACT

Ultrasonic horns configured for use with a surgical ultrasonic handpiece including a resonator are described. The ultrasonic horns include an elongated member having a longitudinal internal channel extending therethrough. Disposed on the distal end of the elongated member is a tip lead configured for cutting and/or abrading hard tissue, for example bone. The tip lead includes an abrasive surface.

44 Claims, 32 Drawing Sheets

$$N = \frac{S_{go}(\text{Area})}{S_c(\text{Area})}$$

New Profile First Past 23 kHz Bone Tip

| | Elastic Modulus $E_g$ (lb/in²) | Weight Density (lb/in³) | Density ρ (lbsec²/in⁴) | Acoustic Velocity $c_g$ (in/sec) | Length Tip $L_{tip}$ (in) | Gaussian Large Diameter $D_{go}$ (in) | Gaussian Channel Diameter $d_g$ (in) | Gaussian Small Diameter $D_c$ (in) | Channel Diameter $d_c$ (in) | Gaussian Start Area $S_{go}$ (in²) | Gaussian End Area $S_g$ (in²) | Gaussian Area Ratio N | Angular Frequency ωi (1/sec) | Frequency $f_c$ (Hz) | Length Gaussian $L_g$ (in) | Length Remaining Horn $L_c$ (in) |
|---|---|---|---|---|---|---|---|---|---|---|---|---|---|---|---|---|
| Gaussian | 16,500,000 | 0.16 | 0.0004147 | 199472.8 | 2.75 | 0.1650 | 0.0780 | 0.1200 | 0.0780 | 0.01660 | 0.00653 | 2.542 | 144,922 | 23,065 | 1.880 | 0.870 |

| | λ@Freq | λ/2@Freq | λ/4@Freq |
|---|---|---|---|
| Titanium | 8.648 | 4.324 | 2.162 |

Wall Thickness (in) = 0.021

*Density based on acceleration due to gravity on 9.8 m/sec2.*

*Original Profile 23 kHz Standard Tip*

| Index | Gaussian Location $x_g$ (in) | Gaussian Area Function $S_{g0}e^{-(\frac{1}{2})(\frac{\omega x}{c})^2}$ (in²) | Diameter $D_{g(x)}$ (in) | Radius $R_{g(x)}$ (in) | Radius $R_{g(x)}$ (in) |
|---|---|---|---|---|---|
| 0  | 0.000 | 0.01664 | 0.1651 | 0.0826 | -0.0826 |
| 1  | 0.083 | 0.01660 | 0.1650 | 0.0825 | -0.0825 |
| 2  | 0.166 | 0.01651 | 0.1646 | 0.0823 | -0.0823 |
| 3  | 0.249 | 0.01635 | 0.1640 | 0.0820 | -0.0820 |
| 4  | 0.332 | 0.01613 | 0.1631 | 0.0816 | -0.0816 |
| 5  | 0.414 | 0.01585 | 0.1621 | 0.0810 | -0.0810 |
| 6  | 0.497 | 0.01551 | 0.1607 | 0.0804 | -0.0804 |
| 7  | 0.580 | 0.01513 | 0.1592 | 0.0796 | -0.0796 |
| 8  | 0.663 | 0.01469 | 0.1575 | 0.0787 | -0.0787 |
| 9  | 0.746 | 0.01422 | 0.1555 | 0.0778 | -0.0778 |
| 10 | 0.829 | 0.01370 | 0.1534 | 0.0767 | -0.0767 |
| 11 | 0.912 | 0.01315 | 0.1511 | 0.0756 | -0.0756 |
| 12 | 0.995 | 0.01258 | 0.1487 | 0.0743 | -0.0743 |
| 13 | 1.077 | 0.01198 | 0.1461 | 0.0730 | -0.0730 |
| 14 | 1.160 | 0.01137 | 0.1434 | 0.0717 | -0.0717 |
| 15 | 1.243 | 0.01075 | 0.1406 | 0.0703 | -0.0703 |
| 16 | 1.326 | 0.01012 | 0.1377 | 0.0689 | -0.0689 |
| 17 | 1.409 | 0.00949 | 0.1348 | 0.0674 | -0.0674 |
| 18 | 1.492 | 0.00887 | 0.1318 | 0.0659 | -0.0659 |
| 19 | 1.575 | 0.00826 | 0.1288 | 0.0644 | -0.0644 |
| 20 | 1.658 | 0.00765 | 0.1258 | 0.0629 | -0.0629 |

1b

New Profile, First Pass 23 kHz Bone Tip

| Index | Gaussian Location $x_g$ (in) | Gaussian Area Function $S_{g0}e^{-\left(\frac{1}{2}\right)\left(\frac{\omega x}{c}\right)^2}$ (in²) | Diameter $D_g(x)$ (in) | Radius $R_g(x)$ (in) | Radius $R_g(x)$ (in) | Remaining Tip Location $x_{tip}$ (in) | Exponential Diameter $D_c \cdot e^{-(0.5)x}$ (in) | Exponential Radius (in) | Exponential Radius (in) | Tangent (in) | Tangent (in) |
|---|---|---|---|---|---|---|---|---|---|---|---|
| 0 | 0.000 | 0.01660 | 0.1650 | 0.0825 | -0.0825 | 1.880 | 0.1200 | 0.0600 | -0.0600 | | |
| 1 | 0.094 | 0.01657 | 0.1649 | 0.0824 | -0.0824 | 1.924 | 0.1174 | 0.0587 | -0.0587 | | |
| 2 | 0.188 | 0.01645 | 0.1644 | 0.0822 | -0.0822 | 1.967 | 0.1149 | 0.0574 | -0.0574 | | |
| 3 | 0.282 | 0.01626 | 0.1637 | 0.0818 | -0.0818 | 2.011 | 0.1124 | 0.0562 | -0.0562 | | |
| 4 | 0.376 | 0.01600 | 0.1626 | 0.0813 | -0.0813 | 2.054 | 0.1100 | 0.0550 | -0.0550 | | |
| 5 | 0.470 | 0.01566 | 0.1613 | 0.0807 | -0.0807 | 2.098 | 0.1076 | 0.0538 | -0.0538 | | |
| 6 | 0.564 | 0.01527 | 0.1598 | 0.0799 | -0.0799 | 2.141 | 0.1053 | 0.0527 | -0.0527 | | |
| 7 | 0.658 | 0.01481 | 0.1579 | 0.0790 | -0.0790 | 2.185 | 0.1031 | 0.0515 | -0.0515 | | |
| 8 | 0.752 | 0.01430 | 0.1559 | 0.0779 | -0.0779 | 2.228 | 0.1008 | 0.0504 | -0.0504 | | |
| 9 | 0.846 | 0.01375 | 0.1536 | 0.0768 | -0.0768 | 2.272 | 0.0987 | 0.0493 | -0.0493 | | |
| 10 | 0.940 | 0.01315 | 0.1511 | 0.0755 | -0.0755 | 2.315 | 0.0965 | 0.0483 | -0.0483 | | |
| 11 | 1.034 | 0.01252 | 0.1484 | 0.0742 | -0.0742 | 2.359 | 0.0945 | 0.0472 | -0.0472 | | |
| 12 | 1.128 | 0.01187 | 0.1456 | 0.0728 | -0.0728 | 2.402 | 0.0924 | 0.0462 | -0.0462 | | |
| 13 | 1.222 | 0.01119 | 0.1426 | 0.0713 | -0.0713 | 2.446 | 0.0905 | 0.0452 | -0.0452 | | |
| 14 | 1.316 | 0.01051 | 0.1395 | 0.0698 | -0.0698 | 2.489 | 0.0885 | 0.0443 | -0.0443 | | |
| 15 | 1.410 | 0.00982 | 0.1364 | 0.0682 | -0.0682 | 2.533 | 0.0866 | 0.0433 | -0.0433 | | |
| 16 | 1.504 | 0.00914 | 0.1331 | 0.0666 | -0.0666 | 2.576 | 0.0847 | 0.0424 | -0.0424 | | |
| 17 | 1.598 | 0.00846 | 0.1298 | 0.0649 | -0.0649 | 2.620 | 0.0829 | 0.0415 | -0.0415 | 0.0411 | -0.0411 |
| 18 | 1.692 | 0.00780 | 0.1265 | 0.0633 | -0.0633 | 2.663 | | | | 0.0274 | -0.0274 |
| 19 | 1.786 | 0.00715 | 0.1233 | 0.0616 | -0.0616 | 2.707 | | | | 0.0137 | -0.0137 |
| 20 | 1.880 | 0.00653 | 0.1200 | 0.0600 | -0.0600 | 2.750 | | | | 0.0000 | 0.0000 |

θ=360° under US Patent 8,142,460 B2

BONE ABRADING ULTRASONIC HORNS

CROSS-REFERENCES TO RELATED APPLICATIONS

This application claims priority to U.S. Provisional Patent Application Ser. No. 60/748,826 entitled Ultrasonic Horns, filed Dec. 9, 2005, and U.S. Provisional Patent Application Ser. No. 60/671,739 entitled Ultrasonic Horns, filed Apr. 15, 2005 the entirety of which are incorporated herein by reference.

BACKGROUND OF THE INVENTION

1. Technical Field

This disclosure relates to surgical systems and, more particularly, to ultrasonic horns for fragmenting tissue during a surgical procedure.

2. Background of Related Art

Devices which effectively utilize ultrasonic energy for a variety of applications are well-known in a number of diverse arts. The Ampulla (Gaussian) profile was published by Kleesattel (as early as 1962), and is employed as a basis for many ultrasonic horns in surgical applications including devices patented and commercialized by Cavitron and Valleylab (patents by Wuchinich, et al, 1977, Stoddard, et al, 2001) for use in ultrasonic aspiration. The Gaussian profile is used in practice to establish and control the resonance and mechanical gain of horns. A resonator, a connecting body and the horn act together as a three-body system to provide a mechanical gain, which is defined as the ratio of output stroke amplitude of the radiating tip to the input amplitude of the resonator. The mechanical gain is the result of the strain induced in the materials of which the resonator, the connecting body and the ultrasonic horn are composed. The magnetostrictive transducer coupled with the connecting body functions as the first stage of the booster horn with a mechanical gain of about 2:1.

The magnetostrictive transducer coupled with the connecting body functions as the first stage of the booster horn with a mechanical gain of about 2:1, due to the reduction in area ratio of the wall of the complex geometry. The major diameter of the horn transitions to the large diameter of the Gaussian in a stepped horn geometry with a gain of as large as about 5:1, again due to reduction in area ratio. The mechanical gain increases in the Gaussian due to the Square Root of (1+2*Ln (Area Ratio)), where Ln is the natural logarithm, or about 2:1 for the horns of interest. The total mechanical gain is the product of these constituents, or as large as 20:1 for this example. Thus, the application of ultrasonically vibrating surgical devices used to fragment and remove unwanted tissue with significant precision and safety has led to the development of a number of valuable surgical procedures. Accordingly, the use of ultrasonic aspirators for the fragmentation and surgical removal of tissue from a body has become known. Initially, the technique of surgical aspiration was applied for the fragmentation and removal of cataract tissue. Later, such techniques were applied with significant success to neurosurgery and other surgical specialties where the application of ultrasonic technology through a handheld device for selectively removing tissue on a layer-by-layer basis with precise control has proven feasible.

Certain devices known in the art characteristically produce continuous vibrations having substantially constant amplitude at a predetermined frequency (i.e. 20-30 kHz). Certain limitations have emerged in attempts to use such devices in a broad spectrum of surgical procedures. For example, the action of a continuously vibrating tip may not have a desired effect in breaking up certain types of body tissue, bone, etc. Because the ultrasonic frequency is limited by the physical characteristics of the handheld device, only the motion available at the tip provides the needed motion to break up a particular tissue. All interaction with the tissue is at the tip, some is purely mechanical and some is ultrasonic. Some teach in the art that interaction with the tissue at the tip lead is due only to mechanical interaction. In any case, the devices have limitations in fragmenting some tissues. The limited focus of such a device may render it ineffective for certain applications due to the vibrations which may be provided by the handheld device. For certain medical procedures, it may be necessary to use multiple hand held devices or it may be necessary to use the same console for powering different handheld devices.

Certain devices known in the art characteristically produce continuous vibrations having a substantially constant amplitude at a frequency of about twenty to about thirty kHz up to about forty to about fifty kHz. The amplitude is inversely proportional to frequency and directly proportional to wavelength because the higher frequency transducers generally have less powerful resonators. For example, U.S. Pat. Nos. 4,063,557, 4,223,676 and 4,425,115 disclose devices suitable for the removal of soft tissue which are particularly adapted for removing highly compliant elastic tissue mixed with blood. Such devices are adapted to be continuously operated when the surgeon wishes to fragment and remove tissue, and generally is operated by a foot switch.

A known instrument for the ultrasonic fragmentation of tissue at an operation site and aspiration of the tissue particles and fluid away from the site is the CUSA™ 200 System Ultrasonic Aspirator manufactured and sold by Radionics, Inc. of Burlington, Mass., a subsidiary of Tyco Healthcare Group LP; see also U.S. Pat. No. 4,827,911, now sold by Radionics, Inc. as the CUSA EXcel™. When the longitudinally vibrating tip in such an aspirator is brought into contact with tissue, it gently, selectively and precisely fragments and removes the tissue. Depending on the reserve power of the transducer, the CUSA™ transducer amplitude can be adjusted independently of the frequency. In simple harmonic motion devices, the frequency is independent of amplitude. Advantages of this unique surgical instrument include minimal damage to healthy tissue in a tumor removal procedure, skeletoning of blood vessels, prompt healing of tissue, minimal heating or tearing of margins of surrounding tissue, minimal pulling of healthy tissue, and excellent tactile feedback for selectively controlled tissue fragmentation and removal.

In many surgical procedures where ultrasonic fragmentation instruments are employed, additional instruments are required for tissue cutting and hemostasis at the operation site. For example, hemostasis is needed in desiccation techniques for deep coagulation to dry out large volumes of tissue and also in fulguration techniques for spray coagulation to dry out the surface of tissues.

The apparatus disclosed in U.S. Pat. Nos. 4,931,047 and 5,015,227 provide hemostasis in combination with an ultrasonically vibrating surgical fragmentation instrument and aspirator. The apparatus effectively provide both a coagulation capability and an enhanced ability to fragment and aspirate tissue in a manner which reduces trauma to surrounding tissue.

U.S. Pat. No. 4,750,488 and its two continuation Patents, U.S. Pat. Nos. 4,750,901 and 4,922,902 disclose methods and apparatus which utilize a combination of ultrasonic fragmentation, aspiration and cauterization.

In an apparatus which fragments tissue by the ultrasonic vibration of a tool tip, it is desirable, for optimum efficiency and energy utilization, that the transducer which provides the ultrasonic vibration operate at resonant frequency. The transducer design establishes the resonant frequency of the system, while the generator tracks the resonant frequency. The generator produces the electrical driving signal to vibrate the transducer at resonant frequency. However, changes in operational parameters, such as changes in temperature, thermal expansion and load impedance, result in deviations in the resonant frequency. Accordingly, controlled changes in the frequency of the driving signal are required to track the resonant frequency. This is controlled automatically in the generator.

During surgery, fragmentation devices, such as the handpieces described above, are used internally to a patient. A surgeon manipulates the handpiece manually at an operative site, and therefore, the handpiece itself may reduce visibility of the operative site. It would therefore be advantageous to provide an apparatus with the above-described features with a smaller profile such that a greater field of view is provided for the surgeon at the operative site.

Emergent requirements for ultrasonic surgical devices include removal of more tenacious brain tumors with calcified or fibrous tissues, cutting or abrading bone encountered given the evolution of transsphenoidal or endoscopic surgical approaches to deeper regions of the brain, and extending openings in bony cavities or sectioning bone to reveal underlying surgical sites with greater control than afforded by existing manual or motorized tissue cutting instruments. Improved approaches to surgery on the spine and orthopedic applications often require cutting or abrading bone for "opening" surgical sites, sculpting, and creating notches, grooves, and blind holes. Inherent in the emergent requirements is the need to protect the critical anatomy (e.g., the carotid artery, optical nerve, other nerves, and glands) in proximity to portions of the instrument while it is inserted and operated. The evolving surgical approaches require the transmission of cutting and abrasion power through small openings, with space shared by endoscopes or the necessary visual field of microscopes, and other surgical instruments (e.g., suction devices, coagulators, etc.).

SUMMARY OF THE INVENTION

In accordance with the present invention, an ultrasonic horn is provide which is configured to remove bone in a controlled manner. The ultrasonic horn of the present invention provides reserve power that is far greater than is needed to readily cut or abrade bone.

In one aspect of the present invention, an ultrasonic horn is provided which can be utilized to remove very fine layers of bone. In yet another aspect of the present invention an ultrasonic horn is provided having fine control characteristics typically exhibited by ultrasonic abrasive devices with file-like structures, while better supporting defined cutting or abrasion of sections, planes, notches, grooves, and holes in bone. Yet another aspect of the present invention is an ultrasonic horn with a profile that affords superior bulk removal of bone as compared to existing ultrasonic devices.

One aspect of the present invention is an ultrasonic horn configured for use with a surgical ultrasonic handpiece having a resonator that generates ultrasound waves. The elongated member has a longitudinal centerline, a proximal end, and a distal end. There is a first intermediate point disposed between the proximal end of the elongated member and the distal end of the elongated member. There is a second intermediate point disposed between the first intermediate point and the distal end of the elongated member. There is a third intermediate point disposed between the second intermediate point and the distal end of the elongated member. There is a fourth intermediate point disposed between the third intermediate point and the distal end of the elongated member. A first hollow portion disposed in the elongated member has a Gaussian profile extending from the proximal end of the elongated member to the first intermediate point of the elongated member. A second hollow portion disposed in the elongated member has a straight profile extending from the first intermediate point to the second intermediate point. A third hollow portion disposed in the elongated member has a flared exponential profile extending from the second intermediate point to the third intermediate point. A fourth hollow portion disposed in the elongated member has an inverse conical profile extending from the third intermediate point to the fourth intermediate point. A fifth hollow portion disposed in the elongated member has a tapering profile extending from the fourth intermediate point to the distal end of the elongated member. There is a tip lead configured on the distal end of the elongated member, the tip lead including the fourth hollow portion and the fifth hollow portion. The tip lead may have a generally planar distal end. The tip lead has an exterior surface that includes an abrasive structure, for example, a mill-file structure.

In still another aspect of the present invention, an extension member is connected to the proximal end of the elongated member by a flared member. An adapter may be disposed on the proximal end of the extension member. An internal channel is longitudinally disposed within the elongated member, the extension member, and the adapter. The internal channel forms a hollow length extending from the proximal end of the elongated member to the distal end of the elongated member. In yet another aspect of the present invention, the internal channel also extends through the extension member and throughout the length of the adapter. The internal channel may terminate before the resonator.

In one aspect of the present invention, the abrasive structure is a mill-file structure. In still another aspect of the present invention, the abrasive structure is configured for lateral abrasion and longitudinal abrasion. Yet another aspect of the present invention is an ultrasonic horn configured to operate at a target frequency of about 36 kHz. In still another aspect of the present invention, the ultrasonic horn is configured to operate at a target frequency of about 23 kHz.

Still another aspect of the present invention is an ultrasonic horn configured for use with a surgical ultrasonic resonator. The ultrasonic horn includes an elongated member having a proximal end and a distal end. The distal end may be planar in configuration. There is a first intermediate point disposed between the proximal end and the distal end. There is a second intermediate point disposed between the first intermediate point and the distal end. There is a third intermediate point disposed between the second intermediate point and the distal end. There is a fourth intermediate point disposed between the third intermediate point and the distal end. There is a fifth intermediate point disposed between the fourth intermediate point and the distal end. An internal channel is longitudinally disposed through the elongated member. The internal channel may have a substantially constant diameter. There is a first hollow portion having a Gaussian profile disposed within the elongated member, the first hollow portion extending from the proximal end of the elongated member to the first intermediate point. There is a second hollow portion having a substantially straight constant diameter profile extending distally from the first intermediate point to the second intermediate point. The substantially straight constant diameter profile has an outer diameter that corresponds to an outer diameter of the first hollow portion at the first intermediate point. A third hollow portion having a flared exponential profile extends distally from the second intermediate point to the third intermediate point. There is a fourth hollow portion having a generally conical profile and an abraded outer surface extending distally from the third intermediate point to the fourth intermediate point. A fifth hollow portion has a generally conical profile and a substantially smooth outer surface and extends distally from the fourth intermediate point to the fifth intermediate point. There is a sixth hollow portion having a tapering profile and a substantially smooth outer surface extending distally from the fifth intermediate point to the distal end.

Yet another aspect of the present invention is an ultrasonic horn configured for use with a surgical ultrasonic handpiece having a resonator. The ultrasonic horn includes an elongated member having a longitudinal centerline, a proximal end, and a distal end. A first hollow portion disposed in the elongated member has a Gaussian profile. A second hollow portion disposed in the elongated member has a straight profile. A third hollow portion is disposed on the distal end of the elongated member. The third hollow portion includes a tip lead configured for removing bone. There is an internal channel longitudinally disposed in the first hollow portion, the second hollow portion, and the third hollow portion. At least a portion of an exterior surface of the tip lead includes an abrasive structure. In one aspect of the present invention, the abrasive structure may include an array of pyramid shaped protrusions aligned both transversely and linearly with respect to the longitudinal centerline of the elongated member. The abrasive structure may also include a plurality of transverse grooves and longitudinal grooves.

In still another aspect of the present invention, an ultrasonic horn is configured for use with a surgical ultrasonic resonator. The ultrasonic horn includes an elongated member having a proximal end and a distal end. The distal end may have a planar configuration. There is a first intermediate point disposed between the proximal end and the distal end, a second intermediate point disposed between the first intermediate point and the distal end, and a third intermediate point disposed between the second intermediate point and the distal end. An internal channel is longitudinally disposed through the elongated member. The internal channel may have a substantially constant diameter throughout its length. The ultrasonic horn also includes a first hollow portion having a Gaussian profile disposed within the elongated member. The first hollow portion extends from the proximal end of the elongated member to the first intermediate point. The ultrasonic horn further includes a second hollow portion having a substantially straight constant diameter profile extending distally from the first intermediate point to the second intermediate point. The outer diameter of the straight constant diameter profile corresponds to an outer diameter of the Gaussian profile at the first intermediate point. Furthermore, the ultrasonic horn includes a third hollow portion having a flared exponential profile that extends distally from the second intermediate point to the third intermediate point. There is also a fourth hollow portion having a generally inverse conical profile extending distally from the third intermediate point to the planar distal end of the elongated member. The fourth hollow portion forms a tip of the elongated member. The tip has an external surface, at least a portion of which may be configured as an abrasive surface.

A further aspect of the present invention is an ultrasonic horn configured for use with a surgical ultrasonic resonator. The ultrasonic horn includes an elongated member having a proximal end and a generally planar distal end. A first intermediate point is disposed between the proximal end and the distal end. A second intermediate point is disposed between the first intermediate point and the distal end. A third intermediate point disposed between the second intermediate point and the distal end. There is an internal channel disposed longitudinally through the elongated member. The internal channel may have a constant internal diameter throughout its length. The ultrasonic horn includes a first hollow portion having a Gaussian profile disposed within the elongated member. The first hollow portion extends from the proximal end of the elongated member to the first intermediate point. The ultrasonic horn further includes a second hollow portion having a substantially straight constant diameter profile extending distally from the first intermediate point to the second intermediate point. The outer diameter of the constant diameter profile is substantially equal to an outer diameter of the Gaussian profile at the first intermediate point. The ultrasonic horn also includes a third hollow portion having a flared exponential profile extending distally from the second intermediate point to the third intermediate point. Also included in the ultrasonic horn is a fourth hollow portion having a conical profile and the generally planar distal end, the fourth hollow portion forming a tip of the elongated member. The tip may have an abrasive mill-file external surface formed according to the conical profile.

Other features and advantages of the present invention will become more apparent from the following detailed description of the invention, when taken in conjunction with the accompanying exemplary drawings.

BRIEF DESCRIPTION OF THE DRAWINGS

Embodiments of the presently disclosed ultrasonic horn are described herein with reference to the drawings, wherein.

DETAILED DESCRIPTION OF THE PREFERRED EMBODIMENTS

Figure 1A:
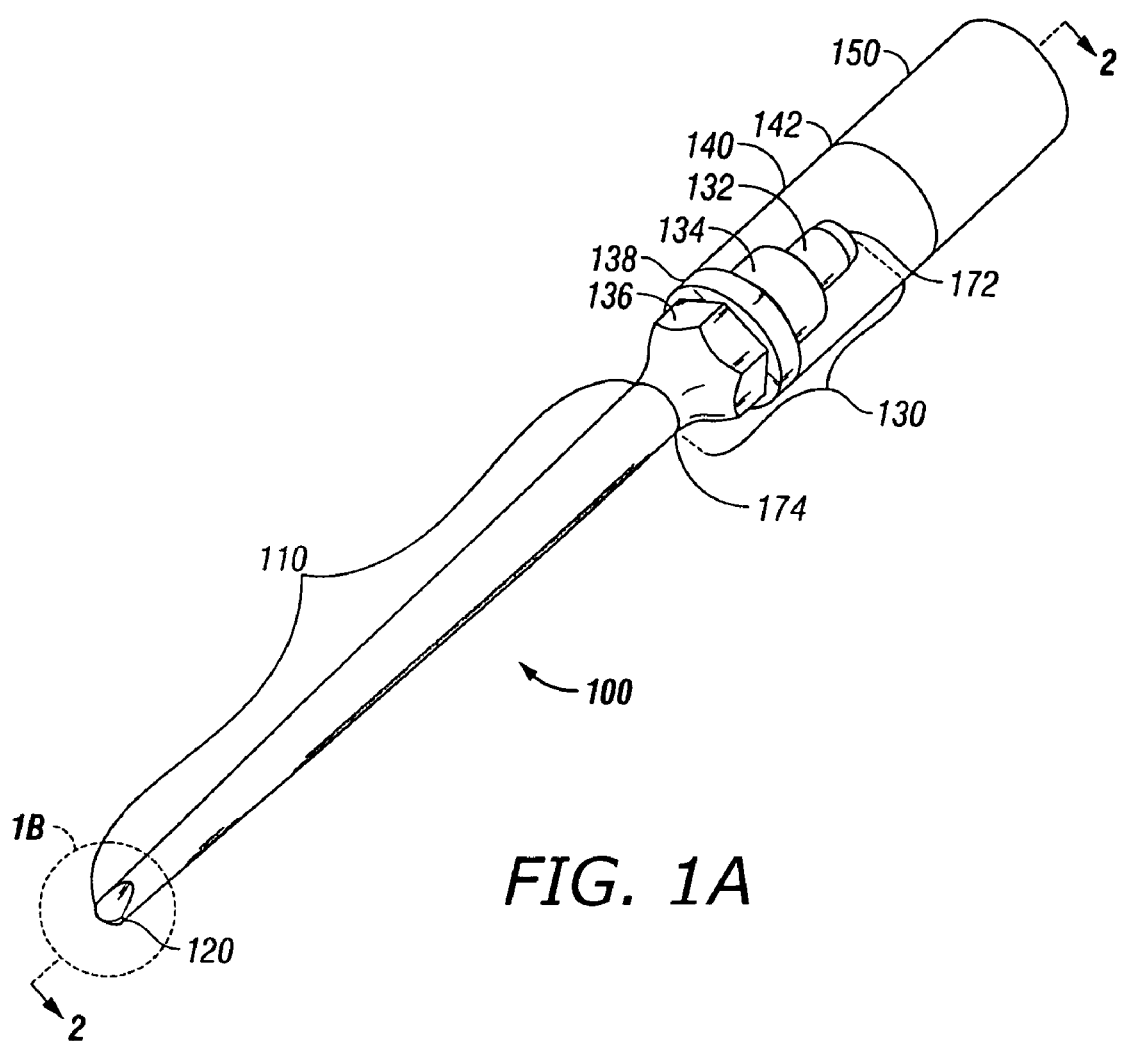
FIG. 1A is a perspective view of an ultrasonic horn in accordance with an embodiment of the present disclosure.

Embodiments of the presently disclosed ultrasonic horn will now be described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

An ultrasonic horn 100, in accordance with one embodiment of the present disclosure, is illustrated in FIG. 1A. Ultrasonic horn 100 is adapted for use in an ultrasonic surgical system having an ultrasonic handpiece. An example of such an ultrasonic surgical system is disclosed in U.S. Pat. No. 6,214,017 to Stoddard et al. currently owned by and assigned to Sherwood Services AG, the entire contents of which are incorporated herein by reference. Alternatively, ultrasonic horn 100 may be adapted for use with the ultrasonic surgical system disclosed in U.S. Pat. No. 4,063,557 to Wuchinich et al., the entire contents of which are incorporated herein by reference.

Figure 1B:
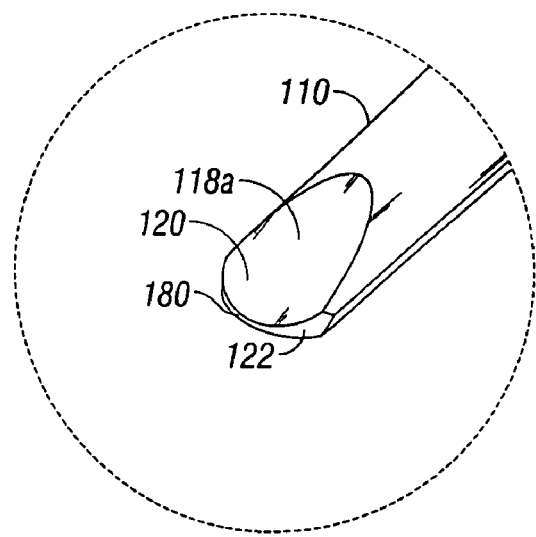
FIG. 1B is an enlarged view of a tip of the ultrasonic horn of FIG. 1A.
Figures 2, 8:
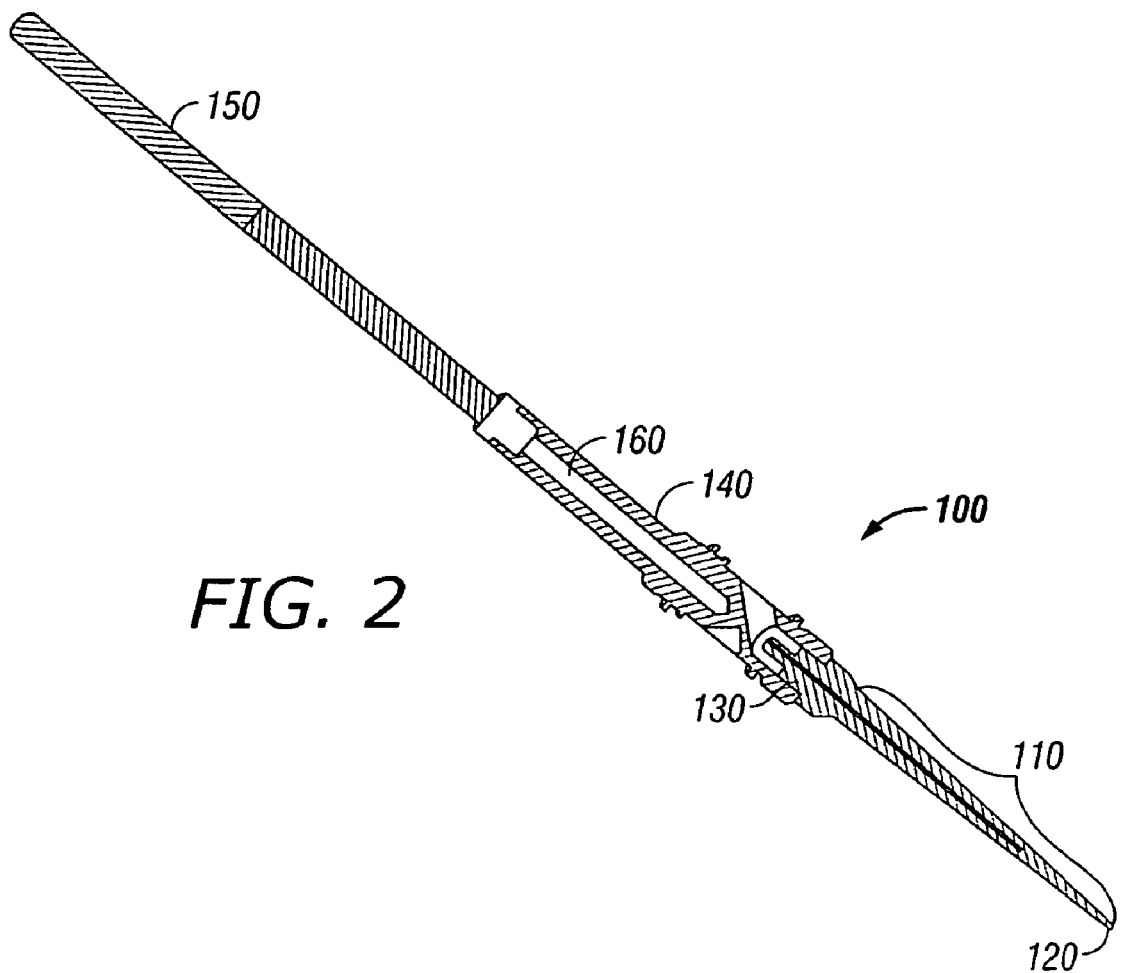
FIG. 2 is a longitudinal cross-sectional view of the ultrasonic horn of FIG. 1A together with a resonator for activating the ultrasonic horn.
FIG. 8 is a cross-sectional view of a portion of the ultrasonic horn according to FIG. 7 showing a Gaussian profile.

Referring to FIGS. 1A, 1B, and 2, in one embodiment of the present disclosure, ultrasonic horn 100 includes an adapter 130 having a first or proximal end 172 and a second or distal end 174. Adapter 130 includes, extending from proximal end 172, a shaft 132, a threaded member 134 and a flange 136 terminating at distal end 174. Flange 136 includes a leading edge 138. Proximal end 172 of adapter 130 is configured to connect ultrasonic horn 100 to an ultrasonic handpiece or resonator 150 via a connecting portion 140. Connecting portion 140 is capable of coupling ultrasonic horn 100 and connecting portion 140 to ultrasonic handpiece or resonator 150. As used herein, the term resonator is used to refer to what is often referred to in the literature as an ultrasonic handpiece. Those skilled in the art will recognize that threaded member 134 is identified herein in one embodiment as an externally threaded member for connection to an internally threaded connecting body and/or to an ultrasonic resonator (not shown) but that other connection types can be implemented to connect to the connecting body and/or ultrasonic resonator. Such connection types include but are not limited to welds, socket couplings, and compression couplings.

Ultrasonic horn 100 includes an elongated member 110 having a first or proximal end which coincides with distal end 174 of adapter 130. Elongated member 110 has a second or distal end 180, and distal end 174 of adapter 130 is joined, in one embodiment unitarily, to the coinciding proximal end of elongated member 110. Distal end 180 of elongated member 110 is configured as a tip lead 120. Tip lead 120 extends from a first or proximal end, as is discussed in more detail below.

Connecting portion 140 includes a first or proximal end 142 which is configured to connect to a resonator 150 at a distal end. Resonator 150 includes, in one embodiment, a magnetostrictive transducer, although other transducer types can be included such as a piezoelectric transducer. Resonator 150 is supplied power from a generator (not shown) such that resonator 150 operates at a desired frequency, e.g., in the range of about 23,000 Hz (23 kHz) to about 36,000 Hz (36 kHz). In one embodiment, ultrasonic horn 100 is made of titanium, although other materials such as stainless steel may be used.

As best seen in FIG. 2, which is a longitudinal cross-sectional view of the ultrasonic horn of FIG. 1A, an internal channel 160 is formed within elongated member 110 and extends into connecting body 140, where it terminates before resonator 150. As is known in the art, the channel terminates in the connecting body, and does not continue in the resonator. The resonator is typically a laminated core-stack of Permanickel. In most implementations, the central channel supports aspiration or suction of tissue. The channel also affords greater mechanical gain because the gain is dependent on the reduction in area ratio of the thin walls. The primary purpose of the channel is to support gain for bone tips with the chisel/awl distal ends. The internal channels of the bone abrading tips in the disclosure shown and described below would also aid in cooling, where irrigation liquid is suctioned via the internal diameter channel. Surgical procedures on bone typically employ an auxiliary suction tube to remove the larger volumes of irrigation liquid and bone debris.

Figure 3:
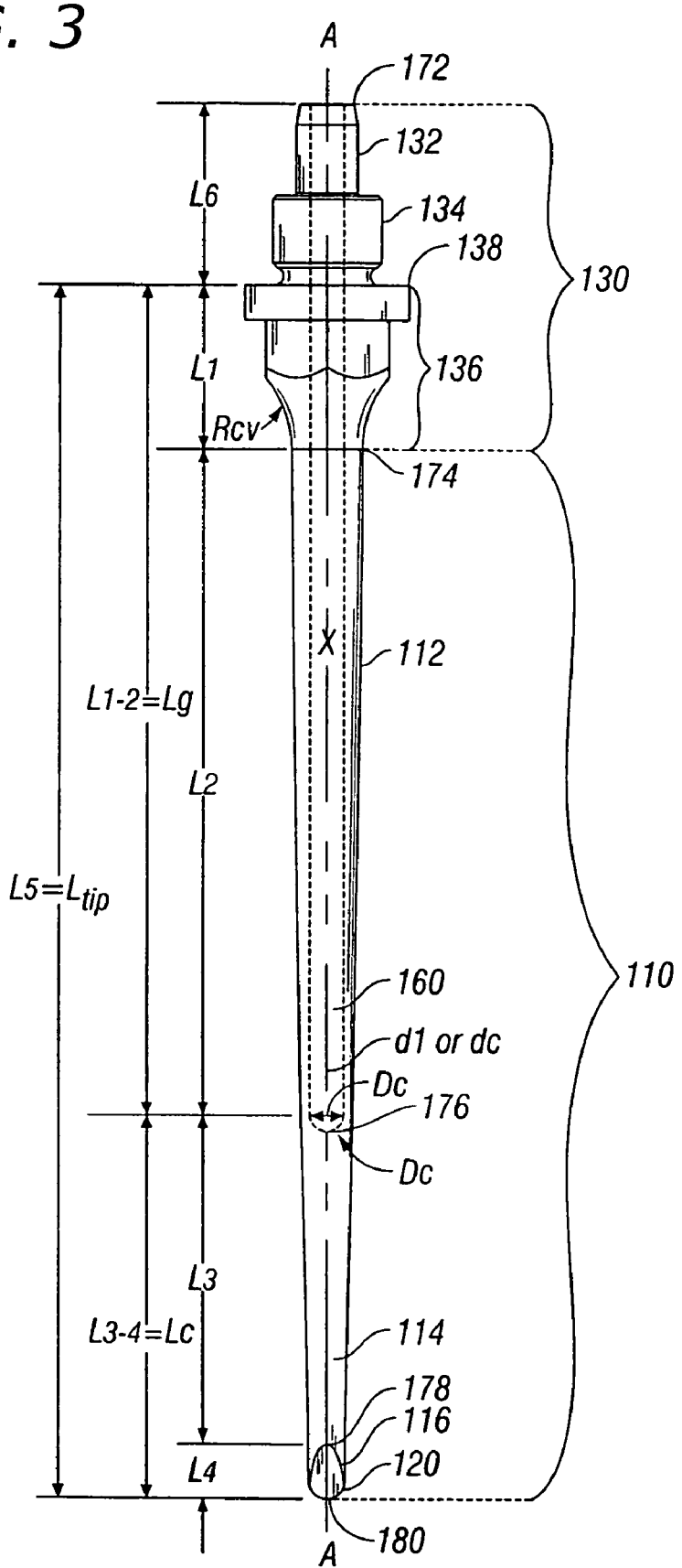
FIG. 3 is a top view of the ultrasonic horn of FIG. 1A with a channel shown in phantom.
Figure 4:
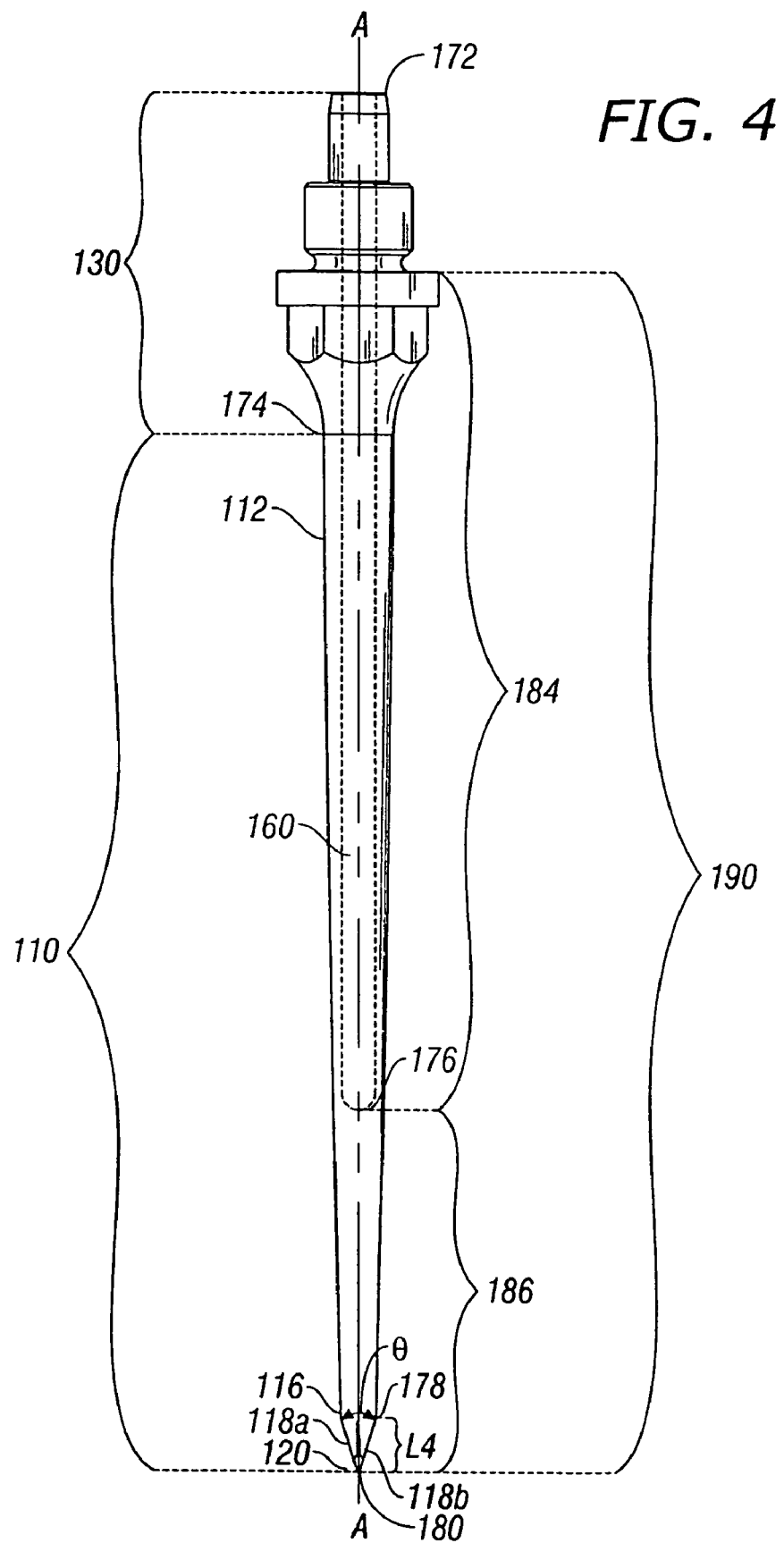
FIG. 4 is a side view of the ultrasonic horn of FIG. 1A.
Figure 5:
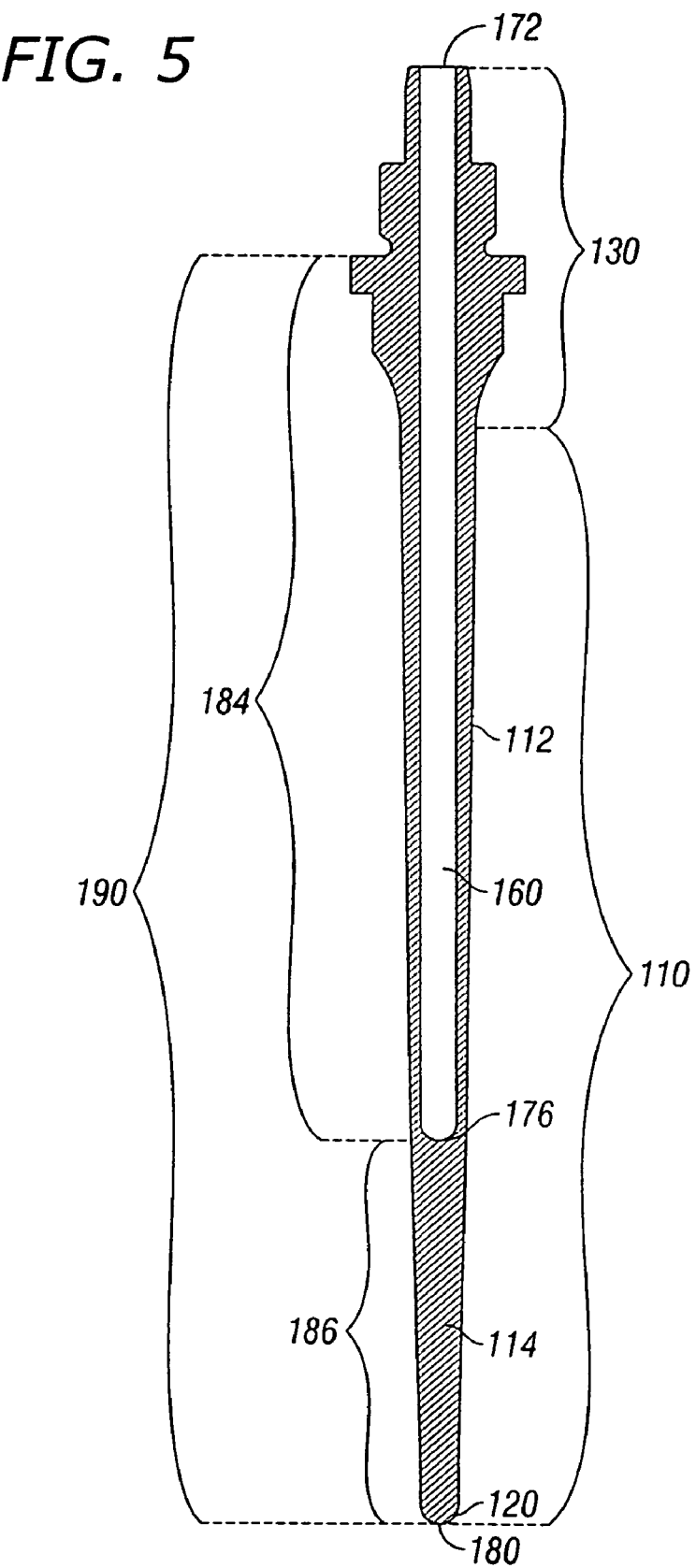
FIG. 5 is a cross-sectional view of the ultrasonic surgical horn of FIG. 3.
Figure 6:
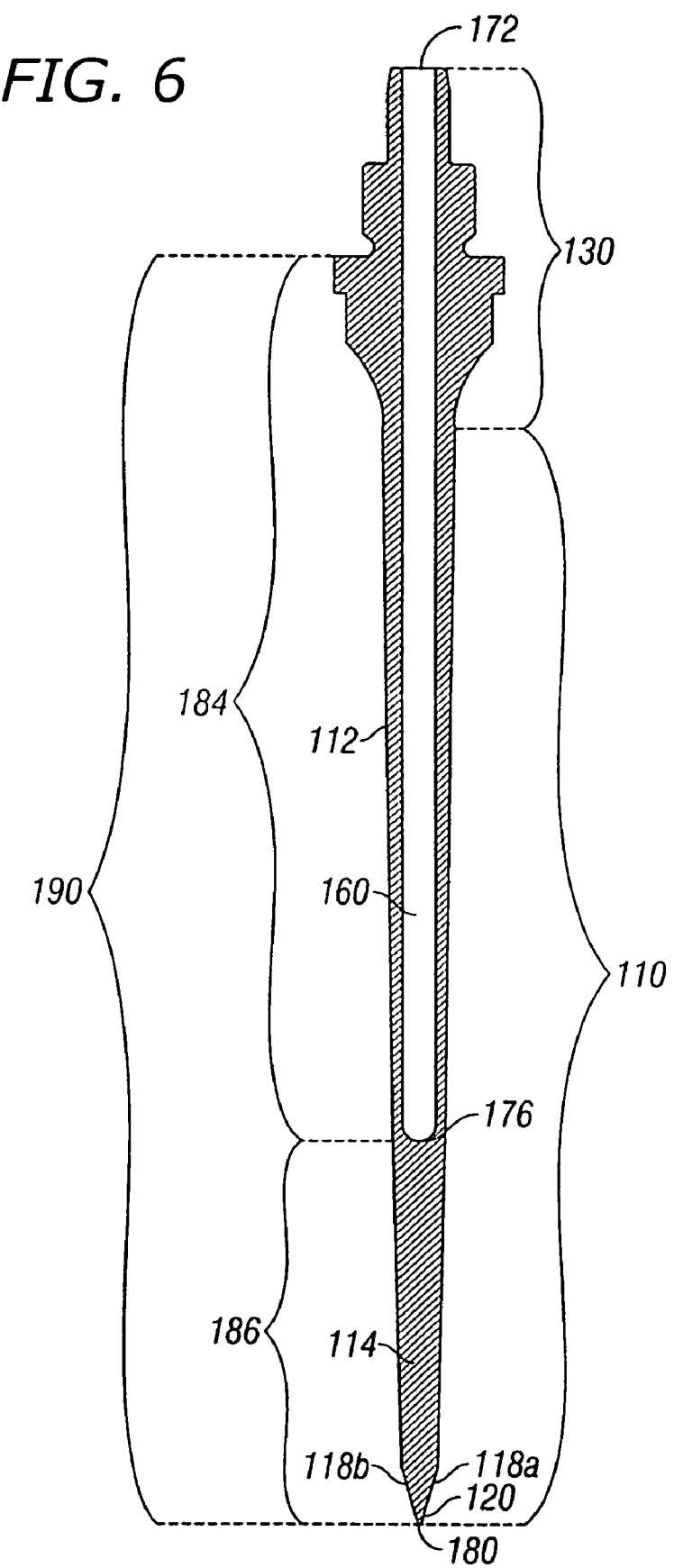
FIG. 6 is a cross-sectional view of the ultrasonic surgical horn of FIG. 4.

Referring to FIGS. 3-6, FIG. 3 is a top view of ultrasonic horn 100 of FIG. 1A with channel 160 shown in phantom formed within elongated member 110. FIG. 4 is a side view of ultrasonic horn 100 of FIG. 1A with channel 160 in phantom formed within elongated member 110. FIG. 5 is a cross-sectional view of ultrasonic surgical horn 100 of FIG. 3 showing channel 160 formed within elongated member 110. FIG. 6 is a cross-sectional view of ultrasonic surgical horn 100 of FIG. 4 again showing channel 160 formed within elongated member 110. Internal channel 160 is formed within adapter 130 and elongated member 110 of ultrasonic horn 100.

Elongated member 110 is tapered such that the cross-sectional area is a maximum at proximal end 174 interfacing with adapter 130 and is a minimum at proximal end 178 of tip lead 120. Channel 160 is a substantially constant diameter central hole of diameter $d_1$ formed within elongated member 110 to enable enhanced mechanical gain in horn 100. As will be explained in more detail below with respect to FIG. 8, an area function is defined as N where N=Sgo/Sc is the area ratio of the Gaussian portion, and it establishes gain as described in the remarks entered above. In the case of a horn with a channel, it is the area ratio of the cross-sectional area based on the outer diameter of the elongated member 110 near the leading edge 138 of flange 136 versus the cross-sectional area based on the outer diameter of the elongated member 110 at the distal end 176 of channel 160. The area ratio along the length L of the horn is decreasing towards tip lead 120 at the distal end of elongated member 110, and velocity and elongation of the titanium particles are increasing. The ultrasonic wave is supported by particle motion in the titanium. The particles are vibrating about their neutral position in a longitudinal or extensional wave. The particles do not move along the length of the horn, but only vibrate, just as a cork or bobber shows that a wave passes through water via the liquid. As the horn wall thickness decreases, more strain occurs in the metal as the particles move a greater distance about their neutral position. The displacement of the end of the horn is due to strain along the horn. All the particles supporting the wave are moving at the same resonant frequency. The greater the strain, the greater the velocity of the particles necessary to maintain the same frequency As illustrated in FIGS. 3-6, several dimensions are identified that form the basis for achieving a desired target frequency of about 23 kHz for ultrasonic horn 100. More particularly, L6 is the length of shaft 132 and threaded member 134 from proximal end 172 of adapter 130 to leading edge 138 of flange 136. L1 is the length of adapter 130 from leading edge 138 of flange 136 to distal end 174 thereof.

As will be explained in more detail below, L2 is the length of a hollow portion 112 of channel 160 formed in elongated member 110 whose outer radius R is formed according to a normal, also referred to as a Gaussian profile distribution. Length L2 extends from the second or distal end 174 of adapter 130, which coincides with the first or proximal end of elongated member 110, approximately to an intermediate point 176 coinciding with the distal end of channel or central hole 160 within elongated member 110. Therefore, the length defined by the sum of L1 and L2 defines the length Lg of the Gaussian profile distribution, or Lg=L1+L2. A portion 184 of the ultrasonic horn 100 is defined by the length Lg of the Gaussian profile distribution. The approximate length of channel 160 within elongated member 110 is length L2. Therefore, channel 160 extends a predetermined distance equal to sum of L6 and L1 and L2 from proximal end 172 of adapter 130 to intermediate point 176 within elongated member 110 between proximal and distal 174 and 180, respectively, of elongated member 110. In addition, channel 160 thereby has an open end at proximal end 172 of the adapter and a closed end at the intermediate point 176 within elongated member 110.

Dimension L3 is the length of a solid portion 114 of elongated member 110 whose radius R is formed according to an inverse exponential profile distribution. Length L3 of solid portion 114 of elongated member 110 extends from approximately second or distal end 176 of channel or central hole 160 to first or proximal end 178 of elongated member 110 at tip lead 120. Dimension L4 corresponds to the length of tip lead 120 and is the length of a solid portion 116 of elongated member 110 extending from first end 178 of elongated member 110 at tip lead 120 to distal end 180 of elongated member 110. Elongated member 110 is thereby a completely solid mass from intermediate point 176 to distal end 180. Therefore, tip lead 120 extends from first or proximal end 178 to second or distal end 180 of elongated member 110. Radius R, or more correctly, height Y, of tip lead 120 is formed according to a tangential or linear profile distribution. L5 is the total length of ultrasonic horn 100 extending from leading edge 138 of flange 136 to second or distal end 180 of elongated member 110 and is equal to the sum of L1, L2, L3 and L4. Length L5=L1+L2+L3+L4 is referred to herein, in accordance with the terminology conventional in the art, as the length of the tip, $L_{tip}$, of ultrasonic horn 100. That is, tip 190 is defined as the portion of ultrasonic horn 100 extending distally from leading edge 138 of flange 136 to distal end 180. Therefore, $L_{tip}$=L5. When ultrasonic horn 100 is connected to connecting portion 140, channel 160 extends through connecting portion 140 and terminates before resonator 150. A portion 186 of ultrasonic horn 100 is defined by sum $L_c$ of lengths L3+L4. Portion 186 extends distally from intermediate point 176 to distal end 180.

As best illustrated in FIG. 1B, distal end 180 of tip lead 120 has a semi-circular planar surface configuration 122, such that distal end 180 of ultrasonic horn 100 is in the form of a chisel and an awl. As discussed below, very tip 180 of ultrasonic horn 100 is blunt or dull. The boring of holes with horn 100 is better facilitated with slightly semi-circular manual motion; however plunge cuts in bone and wood have been accomplished with just longitudinal motion of horn 100. The combination of the chisel and awl distal end 180 of horn 100 supports defined cutting or abrasion of sections, planes, notches, grooves, and holes in bone.

Figure 7:
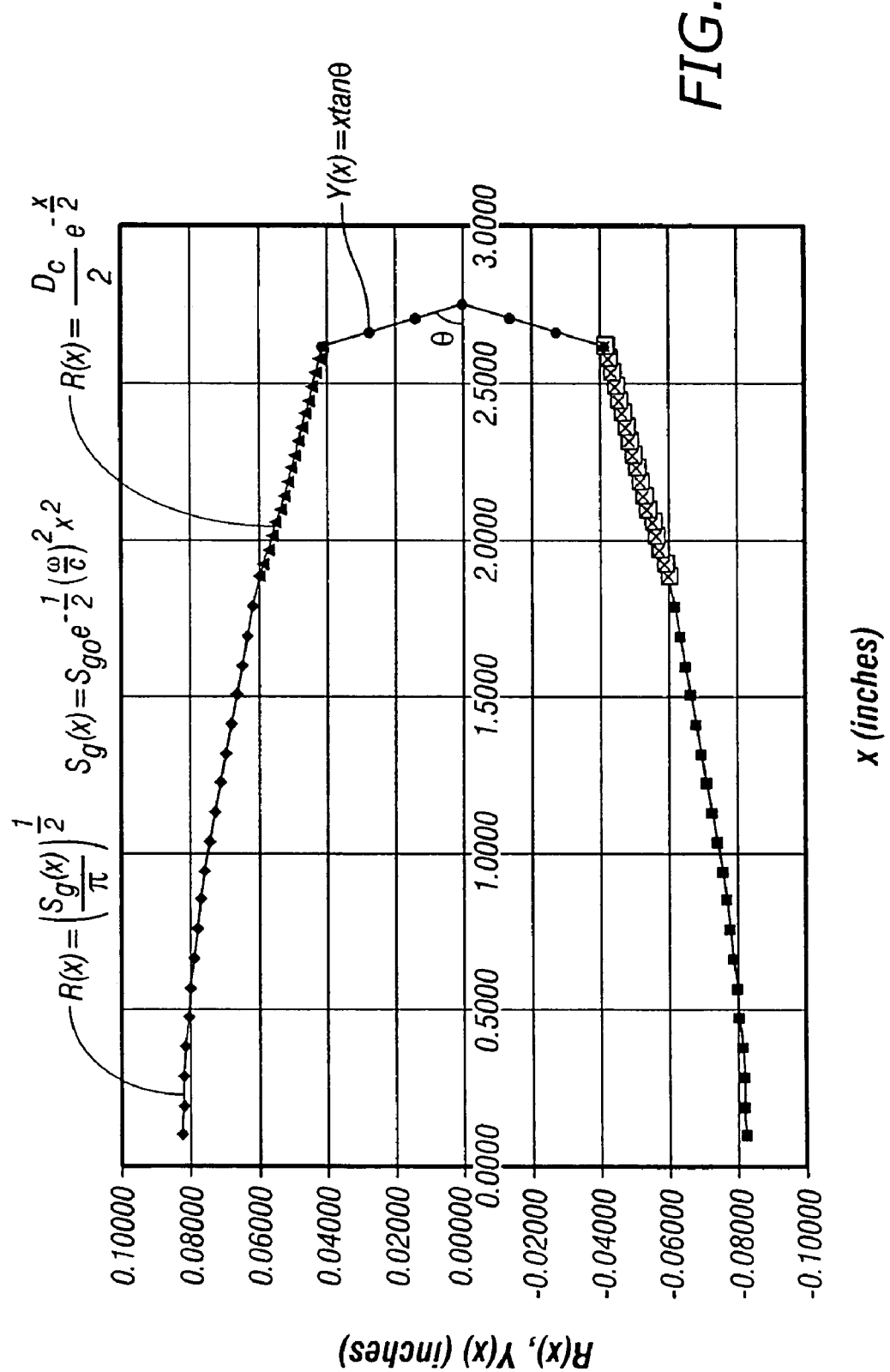
FIG. 7 is a graph of the ultrasonic horn radius versus horn length for a target frequency of 23 kHz.

Channel or central hole 160 extends from proximal end 172 of adapter 130 to approximately distal end 176 of channel 160, which coincides with proximal end of solid portion 114 of elongated member 110. In one embodiment of the present disclosure, as illustrated in FIGS. 7 and 8, the outer radius R(x) of elongated member 110 along hollow portion 112 is formed according to a Gaussian distribution, as given by the following Equations (1), (2), (3), (4), (5), (6), (7) and (8).

$$S_g(x) = S_g o e^{-1/2(\omega_i/Cg)2 \times 2} \tag{1}$$

$$\omega_i = \{C_g/L_{tip}\} \{\arctan(1/[21n(N)]^{1/2}) + [21n(N)]^{1/2}\} \tag{2}$$

$$f_i = \omega_i/2\pi \tag{3}$$

$$N = S_g o / S_c \tag{4}$$

$$R(x) = \{S_g(x)/\pi\}^{1/2} \tag{5}$$

$$S_c = \pi \{D_c/2\}^2 \tag{6}$$

$$S_g o = \pi \{D_g o/2\}^2 \tag{7}$$

$$C_g = [E_g/\rho]^{1/2} \tag{8}$$

where:

x is the distance along the length of the central longitudinal axis A of elongated member 110, with x=0 coinciding with the leading edge 138 of flange 136;

$C_g$ is the speed of sound in the metal, in inches/sec, $E_g$ is the elastic modulus (or Young's modulus) in lbf/inch$^2$, and ρ is the density of the metal in lbm-sec$^2$/inch$^4$. For this application, the metal is titanium, so that $E_g$ is about 16,500,000 lbf/inch$^2$ and ρ is about 0.0004147 lbm-sec$^2$/inch$^4$ Therefore, $C_g$ equals about 199,470 inches per sec.

$D_c$ is the outer diameter {2×|R(x)|} of elongated member 110 at distal end 176 of channel 160, in inches;

$D_{g^o}$ is the outer diameter {2×|R(x)|} of elongated member 110 near leading edge 138 of flange 136. The major diameter of the calculated Gaussian portion 184 lies under the radius of curvature, $R_{cv}$ of the flange 136, as shown in FIG. 3.

Figure 9:
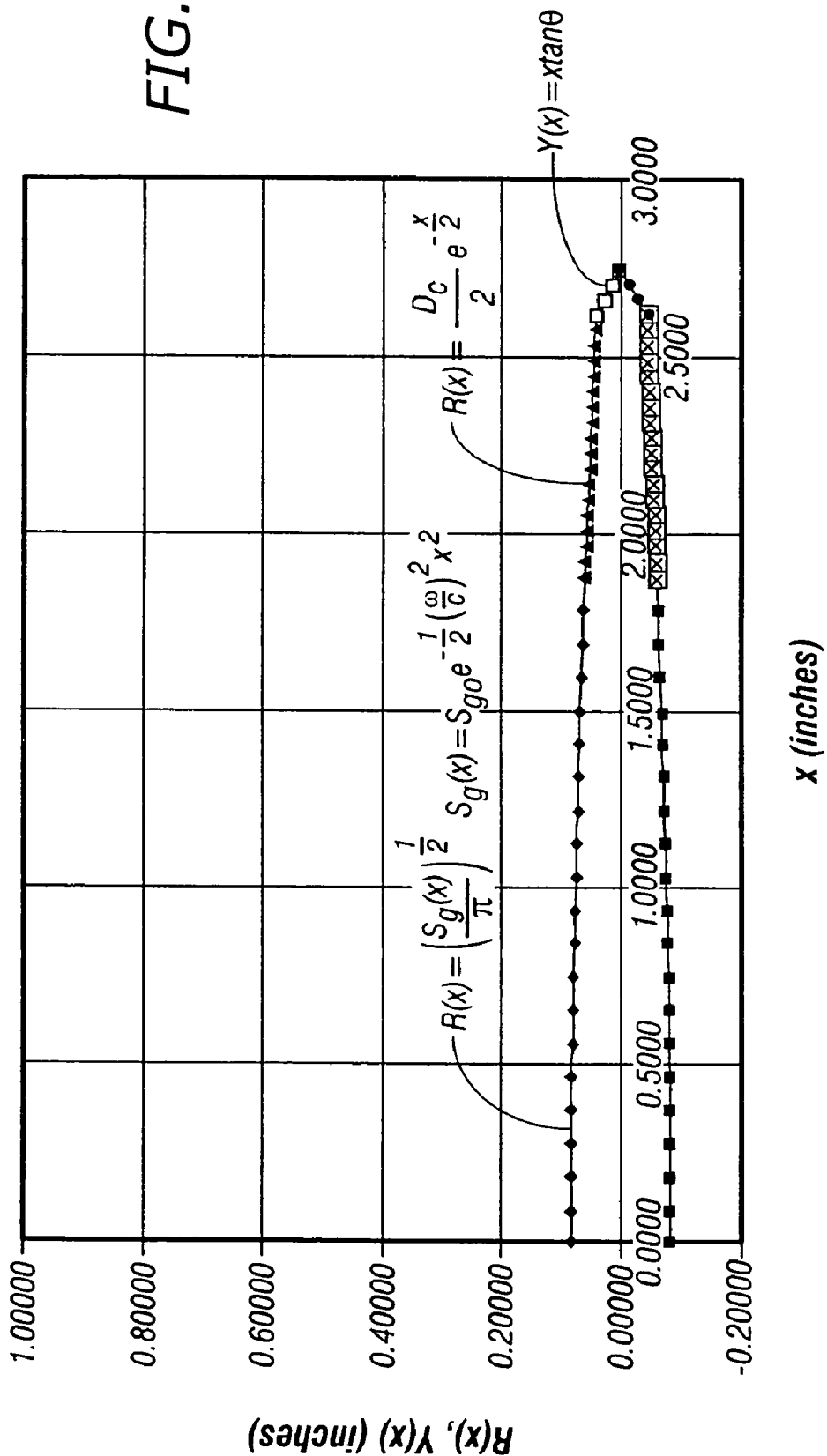
FIG. 9 is another graph of the ultrasonic horn radius versus horn length as illustrated in FIG. 7.
Figure 10:
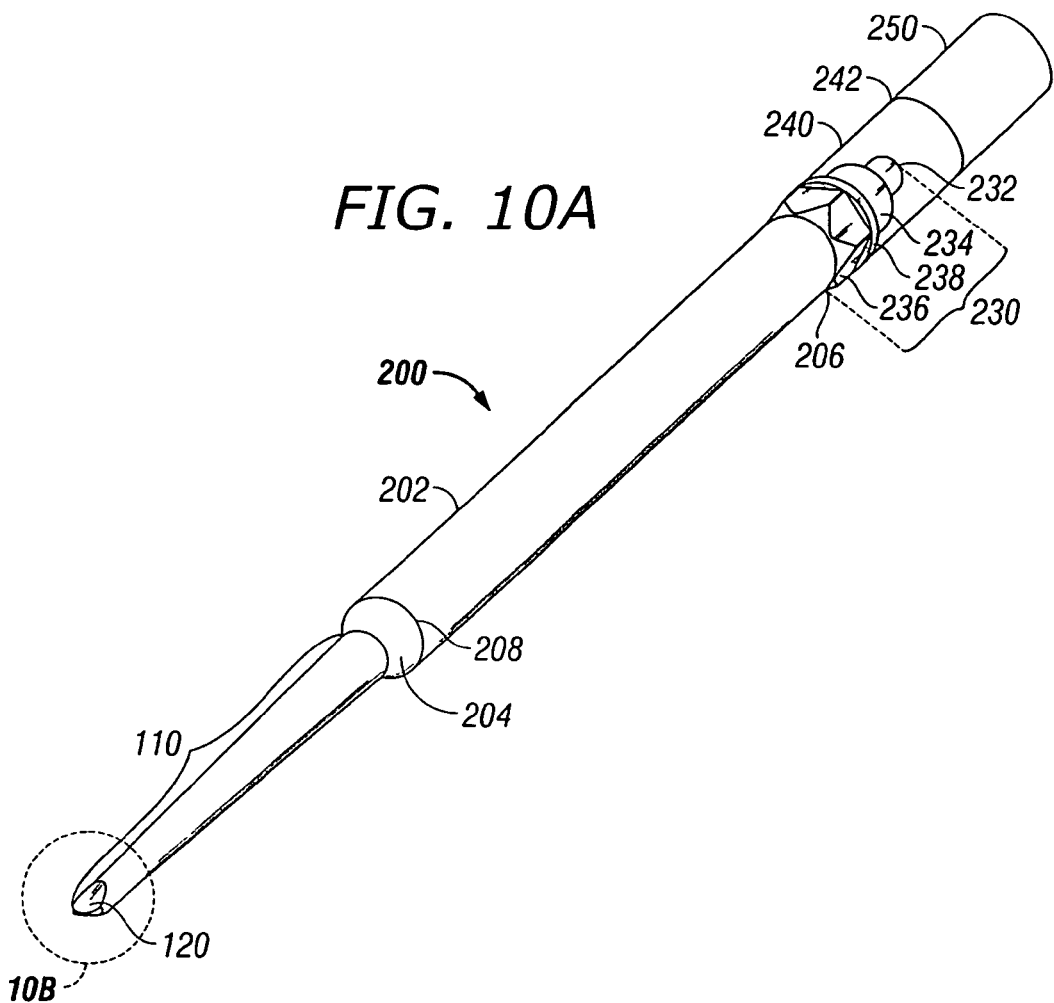
FIG. 10A is a perspective view of an ultrasonic horn in accordance with another embodiment of the present disclosure.
FIG. 10B is an enlarged view of a tip of the ultrasonic horn of FIG. 10A.

$S_c$ is the total cross-sectional area of elongated member 110 at distal end 176 of channel 160, in square inches (see FIG. 9);

$S_{g^o}$ is the total cross-sectional area of elongated member 110 along hollow portion 112 which varies as a function of x, in square inches (see FIG. 9);

N is the ratio of $S_{g^o}/S_c$, a dimensionless number;

$f_i$ is the designed resonant frequency of horn 100 which consists of the Gaussian portion represented by the length Lg=L1+L2 plus the remaining length $L_c$=L3+L4 through to distal end 180 of tip 190, and this resonant frequency is consistent with the combination of resonator 150, connecting body 140, and ultrasonic horn 100, in Hz or cycles/sec.

$\omega_i$ is the angular frequency of resonator 150, connecting body 140, and ultrasonic horn 100, in rad/sec, at resonant frequency $f_i$;

$C_g$ is the acoustic velocity, in in/sec; and $L_{tip}$ is length $L_5$ of tip 190, in inches.

As noted previously, $L_{tip}$, is composed of length $L_g$ of the Gaussian portion 184 plus the length of the remaining horn from distal end 176 of channel 160 to distal end 180 of the ultrasonic horn 100.

The designed angular frequency of the horn, $\omega_i$ in radians/sec, is determined by equation (2). The N value is the area ratio of Gaussian. $L_{tip}$, is composed of length $L_g$ of Gaussian portion 184 plus length $L_c$ of portion 186 of ultrasonic horn 100 defined by sum $L_c$ of lengths L3+L4. Portion 186 extends distally from intermediate point 176 to distal end 180.

Gaussian portion 184 contributes the $[2\ln(N)]^{1/2}$ portion of the equation, and the remaining length $L_c$ represented by portion 186 is approximated by the arcTan of the inverse of $[2\ln(N)]^{1/2}$. It should be noted that the angular frequency $\omega_i$ is controlled by area ratio N, as given by equations (4), (6) and (7), and the length of tip $L_{tip}$ in the divisor, and the speed of sound in titanium $C_g$ is a material property.

The wavelength λ is defined as $C_g/f_i$ and $L_{tip}$=λ/4. Length of resonator 150 is about λ/2, the length of connecting body 140 is about λ/4, and length $L_{tip}$ of horn 100 is about λ/4, and these summing to one full wavelength. These are not ideal dimensions due to complex geometries, and because resonance modes at frequencies other than at 23 kHz exist.

It should be noted that the dimensions do not yield a unique solution because the frequency $f_i$ is dependent on the diameters $D_{g^o}$ and $D_c$ of Gaussian portion 184 and length $L_{tip}$. A shorter or longer length $L_{tip}$ could be selected, and diameters $D_{g^o}$ and $D_c$ adjusted to again attain required frequency $f_i$. These distance and diameter parameters can be adjusted without fundamentally deviating from the Gaussian-decaying exponential-tangent function profile of a chisel awl distal end.

$L_c$ parameter is the length ($L_3$ and $L_4$) of horn 100 remaining after Gaussian portion 184. $L_g$ parameter is the length of Gaussian portion 184. $L_g$ is the dimension of the length from the end of Gaussian portion 184 or its small diameter Dc to large diameter $D_{g^o}$ of Gaussian portion 184. The larger diameters of Gaussian portion 184 actually lie under structure, such as the shaft 132, threaded member 134, and flange 136. It is not practical to mathematically model this complex structure. Physical dimension of $L_g$ is the distance from the beginning of the major diameter of the flange, i.e., leading edge 138 of flange 136, which mates with connecting body 140 and extends distally to intermediate point 176.

To provide tip lead 120 of elongated member 110 with a shape approximating a point of a chisel and awl at distal end 180, solid portion 114 of elongated member 110 is formed with a profile having an outer radius R(x) according to an inverse exponential function as given by the following equation:

$$R(x)=\{D_c/2\}\{e^{-(1/2)x}\} \quad (9)$$

where again $D_c$ is outer diameter {2×|R(x)|} of elongated member 110 at distal end 176 of channel 160, which coincides with proximal end of solid portion 114, in inches. The exponential decay parameter ½ is uniquely selected to precisely transition from the Gaussian distribution at distal end 176 of channel 160.

As an example, in one embodiment of horn 100, function $e^{-(1/2)x}$ can be used. To visualize the profiles in view of the comparatively narrow aspect ratio, (R(x)/x), of actual horn 110, y axis indicating R(x) is magnified in FIG. 7. Central hole 160 is not shown on the graph in FIG. 7. The area function N of the Gaussian distribution of Equation (1) influences resonant frequency $f_i$ and the mechanical gain. Total length L5 of ultrasonic horn 100 is set at λ/4 according to acoustic wavelength λ at resonant frequency $f_i$. As indicated by Stoddard et al., in U.S. Pat. No. 6,214,017 B1, in one embodiment, the lengths of resonator stack 150, connecting portion 140 and ultrasonic horn 100 are λ/2, λ/4, and λ/4, respectively. Therefore, length of resonator 150 plus the length of connecting body 140 plus the length of ultrasonic horn 100 equals λ. The mechanical gain is defined herein as the ratio of the output stroke of the ultrasonic horn at distal end 180 of tip lead 120 to the input stroke at the proximal end of resonator 150. Mechanical gain occurs anywhere there is a change in cross-sectional area of the assembly of resonator 150, connecting body 140 and ultrasonic horn 100. The positions where there is a change in cross-sectional area are for example distal end 174 of adapter 130, distal end 176 of channel 160, and distal end 178 of solid portion 114 of elongated member 110 which interfaces with proximal end of tip lead 120. At resonant frequency, those positions become the locations of nodes and antinodes of acoustic wavelength λ. In particular, since an antinode is a point of maximum displacement, tip lead 120 is therefore near an antinode. Since a node is a point of minimum displacement, proximal end 172 of adapter 130 is near a node. Therefore, proximal end 172 of adapter 130 intersects a node of a generated ultrasonic wave and tip lead 120 at second end 180 of elongated member 110 intersects an anti-node of the generated ultrasonic wave. The absolute positions of the nodes and antinodes are not exact because the geometry is quite complex, i.e., the geometry does not consist simply of bars, rods, Gaussian, exponential, etc. Actual finite element analysis modeling, using programs such as PRO/Mechanica (by PTC of Needham, Mass., USA), of the entire geometry complements the simple mathematical model shown in FIG. 7. The simple mathematical model does illustrate the need for proper selection of the horn geometry. Again, the inverse exponential distribution profile of Equation (9) is selected for the outer diameter of solid portion 114 because its decay parameter can be readily varied to better transition to the Gaussian distribution of Equation (1) for hollow portion 112, and the exponential decay provides a smooth and gradual yet rapid transition in outer diameter $D_c$ conducive to propagation of ultrasound with minimal errant reflection and standing waves.

The inverse exponential distribution profile, i.e., Equation (9), of solid portion 114 of horn 110 next interfaces at first or proximal end 178 of tip lead 120 at a chisel angle θ uniquely selected because it supports a termination of total length L4 of tip lead 120. Total length L4 resulting from selected chisel angle θ is a parameter beneficial to establishing resonant frequency, and promotes a reasonable transition to the inverse exponential profile R(x) of Equation (9). Ultrasonic horn 100 in one embodiment is formed of titanium 6A14V although other materials such as stainless steel can be used. Horn 100 resonates with a length near but not exactly a quarter wavelength λ/4 (or multiples thereof) of the speed of sound in titanium. In fact, unless transducer 150, connecting body 140, and horn 110 resonate, the stroke amplitude and propagation of ultrasound is minimal. Chisel angle θ is the angle between central longitudinal axis A of elongated member 110 and chisel interface or opposing outside surfaces 118a and 118b, and is best considered as a tangent function that is projected back from the required termination of length of horn 100. Vertical dimension Y(x) of tip lead 120 is therefore a function of chisel angle θ, as given by the following equation:

$$Y(x) = x \tan \theta \qquad (10)$$

Vertical dimension Y(x) can also be considered to be the distance between the central longitudinal axis A and the respective opposing surfaces 118a and 118b. Chisel angle θ also presents interface surfaces 118a and 118b to the ultrasound so that forward propagation occurs rather than errant reflection or mode conversion which could occur at greater angles. Chisel angle θ also functions well in chiseling bone, where greater angles can promote burrowing and greater resistance, and lesser angles cause slippage. In one embodiment of the present disclosure, θ is about 35°, although other values of θ can be used.

It should be noted that while the vertical dimension of tip lead 120 is given by chisel angle θ as described above for Equation (10) as best illustrated in FIG. 4 and FIG. 6, horizontal dimension of tip lead 120 continues to be given by the inverse exponential profile distribution $R(x) = \{D_c/2\}\{e^{-(1/2)x}\}$ given by Equation (9).

FIG. 9 illustrates the horn profile in one embodiment using solid model views of the actual profile. The horn profile is shown still somewhat magnified but the transition of the inverse exponential profile to Gaussian and to the chisel angle are visualized closer to the actual shape. It should be noted that although tip lead 120 appears to come to a sharp point in FIGS. 7 and 9, in actuality, tip lead 120 is, in one embodiment, flat or chisel/awl shaped as best shown in FIG. 1B.

In one embodiment of the present disclosure, FIGS. 10A and 10B through FIG. 14 illustrate an ultrasonic horn which is designed for a different resonant frequency such as 36 kHz. More particularly, ultrasonic horn 200 is identical to ultrasonic horn 100 of FIGS. 1 through 9 except for an extension member 202 which extends overall length of horn 200. In view of the similarity between horns 100 and 200, like parts are similarly numbered and only those parts which are unique to ultrasonic horn 200 are numbered differently.

Figure 11:
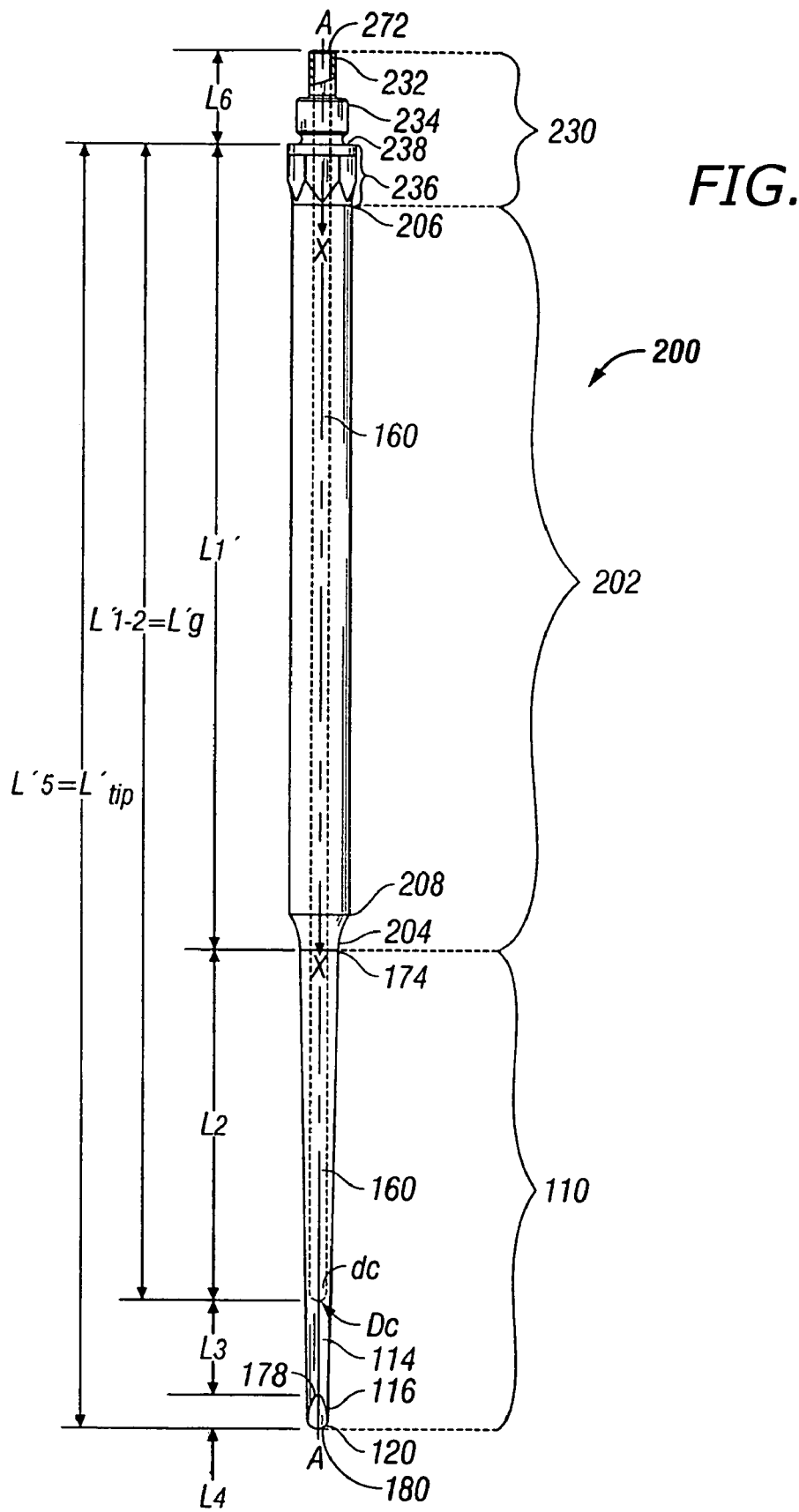
FIG. 11 is a top view of the ultrasonic horn of FIG. 10A with a channel shown in phantom.
Figure 12:
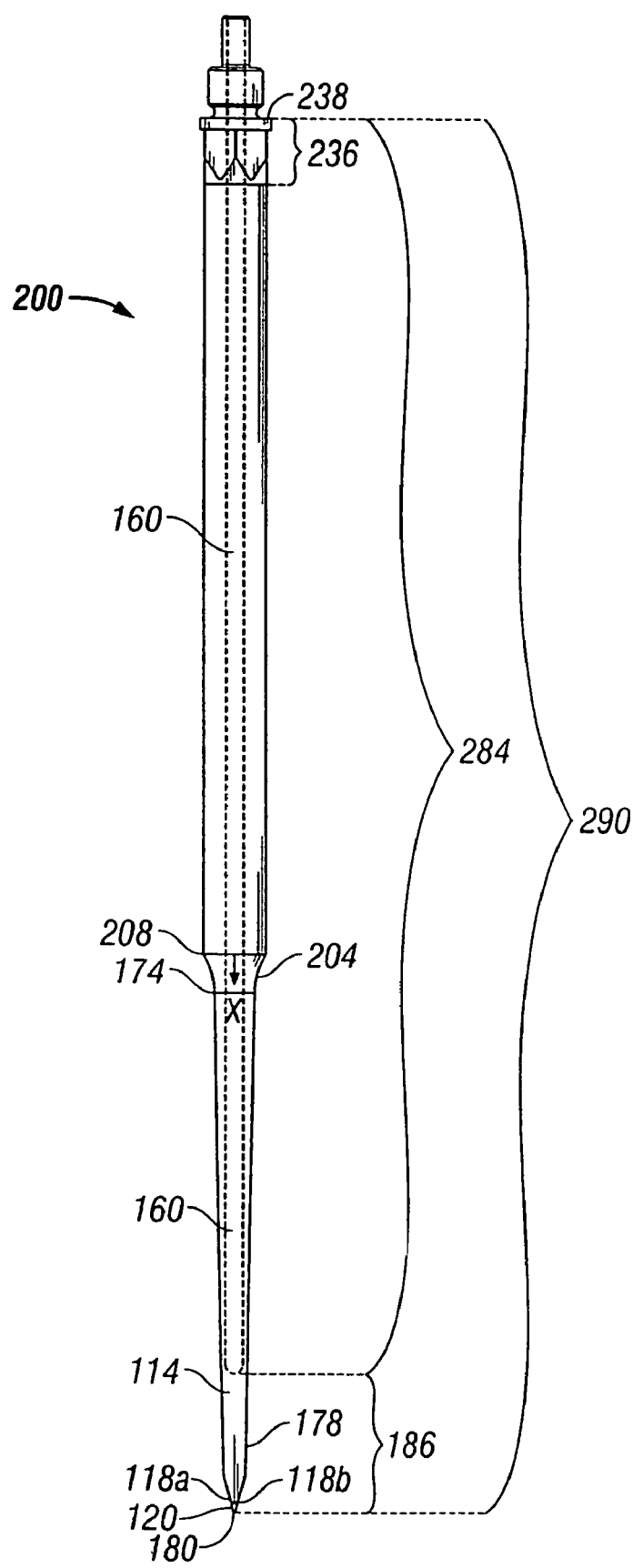
FIG. 12 is a side view of the ultrasonic horn of FIG. 10A.
Figure 13:
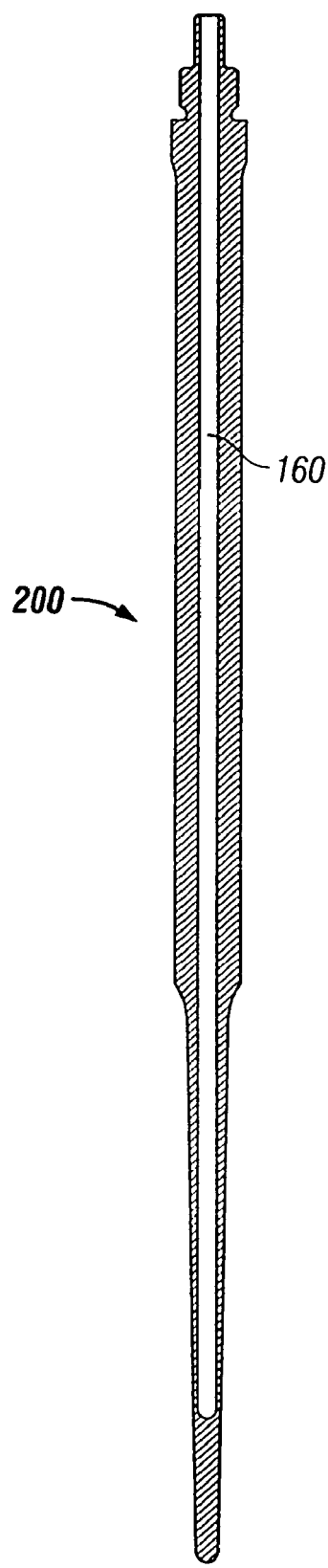
FIG. 13 is a cross-sectional view of the ultrasonic surgical horn of FIG. 11.
Figure 14:
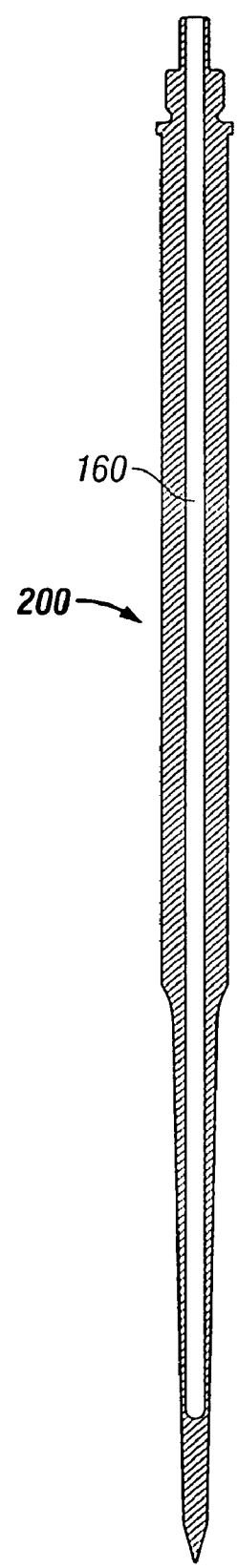
FIG. 14 is a cross-sectional view of the ultrasonic surgical horn of FIG. 12.

As best illustrated in FIGS. 11 and 12, extension member 202 has a proximal end 206 and a distal end 208. An adapter 230 has a proximal end 272 and a distal end coinciding with proximal end 206 of extension member 202. Adapter 230 includes, extending distally from proximal end 272, a fillet 232, a nut 234 and a flange 236 terminating at proximal end 206 of extension member 202. Length L6 is the length of fillet 232 and nut 234 from proximal end 272 of adapter 230 to leading edge 238 of flange 236. A flared member 204 is disposed at proximal end 174 of elongated member 110 and at distal end 208 of extension member 202. Adapter 230 and flared member 204 are, in one embodiment, unitarily connected to extension member 202.

It should be noted that the extension member, 202, is shown as a straight circular cylinder or tube. However, in commercially available embodiments, such as the CUSA EXcel™ 36 kHz Model Curved Extended Micro Tip, C4611 (See the 2005 CUSA EXcel™ Ultrasonic Surgical Aspirator Product Catalog by Tyco Healthcare LP; www.radionics.com/products/cusa/cusa-catalog.pdf), this extension member can be curved. An embodiment of the ultrasonic horn 200 disclosed herein has been tested and can be readily manufactured with a curved extension member of about 13° or less. The curved extender affords improved line-of-sight to the distal end by removing the connecting body and resonator further from the field of view.

Constant diameter channel 160 extends through adapter 230, extension member 202 and flared member 204. The outer diameter of extension member 202 is substantially constant and is greater than outer diameter $D_{g°}$ of elongated member 110 at proximal end 174. Therefore, flared member 204 forms a transition member between the outer diameter of extension member 202 and outer diameter $D_{g°}$ of elongated member 110 at proximal end 174. Dimension L1' is the length along central longitudinal axis A extending distally from leading edge 238 of adapter 230, extension member 202 and flared member 204, to distal end 174 of flared member 204.

As a result, length Lg' of a Gaussian profile portion 284 of ultrasonic horn 200 is defined by sum $L_{1'-2}$ of lengths L1' and L2, or Lg'=L1'+L2. L5' is the length of ultrasonic horn 200 extending distally from leading edge 238 of flange 236 to distal end 180 and is equal to the sum of L1', L2, L3 and L4. Therefore, L5' equals length $L'_{tip}$ of ultrasonic horn 200 and L5'=$L'_{tip}$. The approximate total length of channel 160 is the sum of L6', L1' and L2 or L6' and Lg'. Tip 290 is defined as the portion of ultrasonic horn 200 extending distally from leading edge 238 of flange 236 to distal end 180.

Proximal end 272 of adapter 230 is configured to connect to a connecting portion 240 which is disposed in proximity to proximal end 272 of adapter 230. A proximal end 242 of connecting portion 240 is configured to connect to a distal end of a resonator 250. Again, as is the case with resonator 150, resonator 250 includes, in one embodiment, a magnetostrictive transducer, although other transducer types can be included such as a piezoelectric transducer. Resonator 250 is supplied power from a generator (not shown) such that resonator 250 operates at a desired resonant frequency, such as in the range of 36,000 Hz (36 kHz). Lengths L1', $L_{1'-2'}$, and L5' of ultrasonic horn 200 are determined in the same manner as determined for ultrasonic horn 100, taking into consideration in this case connecting body 240 and resonator 250 which are designed for a resonant frequency of about 36 kHz. As is the case of ultrasonic horn 100, tip lead 120 at distal end 180 is of a flat or chisel/awl shape as best shown in FIG. 10B.

EXAMPLE

Figure 15:
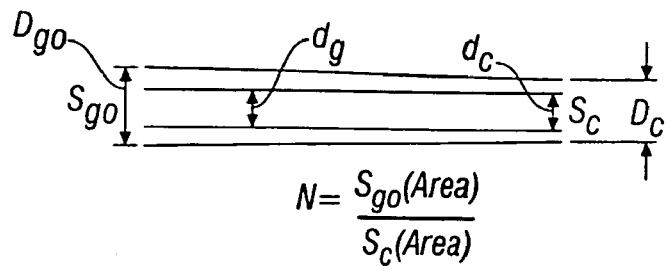
FIG. 15 illustrates the cross-sectional view of a portion of the ultrasonic horn of FIG. 8 showing a Gaussian profile together with a table illustrating sample modeling data and results from several ultrasonic horns that were fabricated according to an embodiment of the present disclosure.

In one embodiment of horn 100, as indicated in FIG. 15, a 23 kHz resonant frequency titanium tip lead 120 of the profile discussed was developed to match the design frequency $f_i$ of the existing CUSA™ transducer. FIG. 15 illustrates the benefits of being able to transfer models to automated contouring machine practices, wherein the results of modeling of the area function of the Gaussian and associated outside diameters, D, and internal hole diameters, d, are provided. In particular, the following diameters are shown in FIG. 15 and in the associated table of data: (a) $D_{g^o}$ is the outer diameter of elongated member 110 along hollow portion 112, which varies as a function of x, in inches; (b) dg is inner diameter of hollow portion 112 of elongated member 110 and is substantially constant.

A particular benefit of the mathematical approach to the profile, which includes the wall defined by the Gaussian and channel, the decaying exponential solid, and tangent function of the chisel was that the resonant frequency $f_i$ predicted was achieved in the first actual devices. Solid modeling and finite element analysis (FEA) better captured ancillary geometry, such as flanges, cylinders to be threaded, and side drilled holes, that were too complex to be mathematically modeled. The modal analysis of the solid models generally predicted a resonant mode with a repeatable shift in frequency, i.e., the predicted resonant frequency was about 4% greater than measured on actual devices. The solid modeling and FEA greatly facilitated evaluation of stresses, node locations, and prediction of amplitude of the stroke of the horn. The majority of the horn profile was also readily accomplished in contour turning operations, with only chisel/awl tip 180 of horn 100 requiring additional machining.

The first row of data (1) indicated a predicted frequency $f_i$ of 23,065 Hz for the new horn 100. As an illustration, a second row of data (2) revealed that even a 0.001 inch deviation in one profile diameter, i.e., $D_c$ from 0.120 to 0.121 in., shifts the horn from design resonance $f_i$ by about 150 Hz, i.e., $f_i$ shifts from 23,065 Hz to 22,908 Hz, where stroke amplitude and propagation of ultrasound are minimal, resulting in an adverse condition shifting the horn characteristics out of resonance conditions. The third row of data (3) in FIG. 15 shows results of the first five horns characterized that were fabricated to the model, and these were remarkably on the resonant frequency target $f_i$ without a Gaussian profile adjustment. The data in the third row (3) were acquired with a power meter at a 40% amplitude setting of the CUSA™. Stroke amplitude was measured optically. The horns addressed herein have symmetric stroke, where the distal end vibrates positively and negatively from its neutral or datum position. Stroke amplitude is defined as the peak excursion of the distal end of the horn. Horn displacement is generally defined as the peak-to-peak amplitude, and for symmetric motion, the horn displacement is twice the stroke amplitude. As can be seen, the manufacturing practice afforded with the profile has the required precision for production.

Figure 16A:
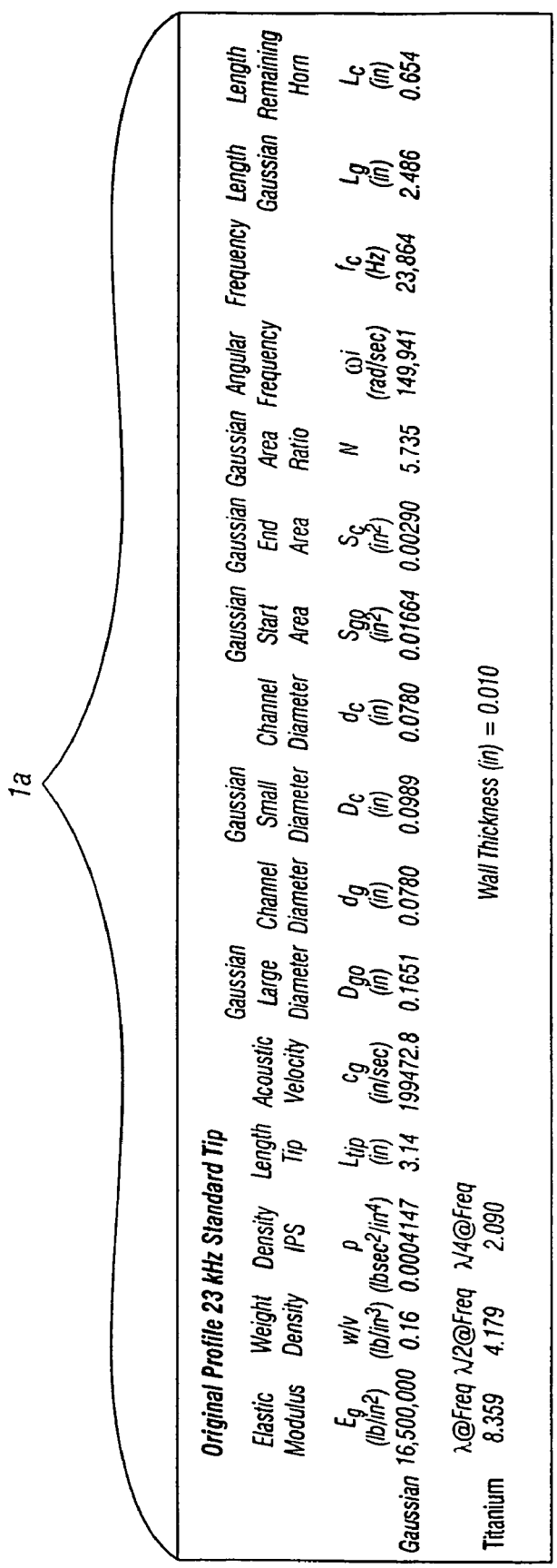
FIG. 16 is a table of experimental data comparing parameters of an ultrasonic horn according to the present disclosure to parameters of an ultrasonic horn of the prior art.

FIG. 16 is a table of experimental data comparing parameters of an ultrasonic horn according to the present disclosure to parameters of an ultrasonic horn of the prior art. More particularly, blocks 1a and 1b indicate parameters and data pertaining to an ultrasonic horn of the prior art with a standard tip, in particular, the CUSA EXcel™ 23 kHz Model C4601S (See the 2005 CUSA EXcel™ Ultrasonic Surgical Aspirator Product Catalog by Tyco Healthcare LP; www.radionics.com/products/cusa/cusa-catalog.pdf). Blocks 2a and 2b indicate parameters and data which pertain to an ultrasonic horn of the present disclosure such as ultrasonic horn 100 having a nominal resonant frequency of 23 kHz as previously described with respect to FIGS. 1A, 1B through FIG. 9.

It should be noted that the value of $D_c$ in row 1a is only 0.09888 in. versus $D_c$ of 0.120 in. in row 1 of FIG. 15. With respect to the horn configuration corresponding to the data of FIG. 15, the diameter $D_c$ was increased to achieve a larger wall thickness for the Bone Tip, such that it would have greater structural rigidity to lateral loads that could result from pushing on the chisel. The minimum wall thickness was increased from about 0.010 in to greater than about 0.020 in.

The specific parameters indicated in FIG. 16 are defined as follows:

$E_g$ is the Elastic Modulus (sometimes called Young's Modulus) of the titanium material used to fabricate the horns;

w/v is the weight density or weight per unit volume;

$\rho$ is the density in IPS (Inch Pound System) or $\rho=(w/V)(1/g)$, adopting a gravitational acceleration of 9.8 m/s² at sea level;

$L_{tip}$ is the length of the Gaussian, $L_g$, plus the length of the remainder of the horn, $L_c$;

$C_g$ is the acoustic velocity of the titanium metal;

$D_{go}$ is the large diameter of the Gaussian portion;

$d_g$ is the channel internal diameter;

$D_c$ is the small diameter of the Gaussian portion;

$d_c$ is the channel internal diameter, and is equal to $d_g$ in the case of a constant diameter hole;

$S_{go}$ is the cross-sectional area of the wall of the Gaussian large diameter minus the cross-sectional area of the channel;

$S_c$ is the cross-sectional area of the wall of the Gaussian small diameter minus the cross-sectional area of the channel;

N is the Gaussian ratio of $S_{go}/S_c$;

$\omega_i$ is the designed angular frequency in radians/second of the Gaussian portion;

$f_i$ is the frequency in Hz, or $\omega_i/2\pi$;

$L_g$ is the length of the Gaussian portion or the distance from the large diameter of the Gaussian portion to the end of the Gaussian portion at its small diameter end. For all of the ultrasonic horns of the present disclosure, this length corresponds to the distance from the leading edge, such as leading edge 138 of the flange 136, to the end of the Gaussian portion at its small diameter end; and $L_c$ is the distance from the end of the Gaussian to distal end of the horn.

The data designated as block 2a correspond to the First Pass Gaussian for Solid Distal End data.

The data designated as block 2b are of particular interest as they determine the characteristics for the New Profile. The first column, index, is an index to generate evenly spaced x values. The next column, xg, is the x distance from a datum of zero at the first large diameter of the Gaussian, which corresponds to leading edge 138 of flange 136 on adapter 130 that mates with connecting body 140. This is described earlier in the remarks. The profile area is calculated for plotting purposes in the next column, and each successive value is smaller from the large diameter of the Gaussian to the small diameter of the Gaussian. The $D_g(x)$ column is the calculated diameter at each x location, and the positive and negative values of the radii are calculated in the next columns, primarily for plotting purposes. The New Profile xg, distances end at index 20 with a distance of 1.8802 inch. The exponential begins using the xtip index at 1.8802. There is one point of overlap in the plots. The Diameter $DcNew1e^{(-0.5x)}$ is the next column, which starts calculation of the adjacent exponential decay diameter. The positive and negative radii are calculated in the next columns for plotting purposes. The positive and negative tangent values are calculated for the chisel end 180 of the tip lead 120 in the subsequent columns. The spreadsheet enables viewing the continuity and blend of the profiles in very simple plots. The approach has evolved where the blends are now determined automatically on the spreadsheet.

It is of interest to note that the frequency of the actual devices operated at 40% amplitude was 23,050 Hz, but operating the ultrasonic horn assemblies of the present disclosure at 100% amplitude results in a reduction in frequency, where stable operation approaches the 23,000 Hz. The ultrasonic horn assemblies of the present disclosure reach a thermal equilibrium within two minutes. The higher amplitude quiescent point and resulting increased temperature reduces frequency. Measurements are taken at both 40% and 100% amplitude, but because the voltage waveforms become distorted at 100% amplitude, due to limitations of the power supply, comparative data on the horns are best viewed at a lower amplitude of operation.

Figure 17:
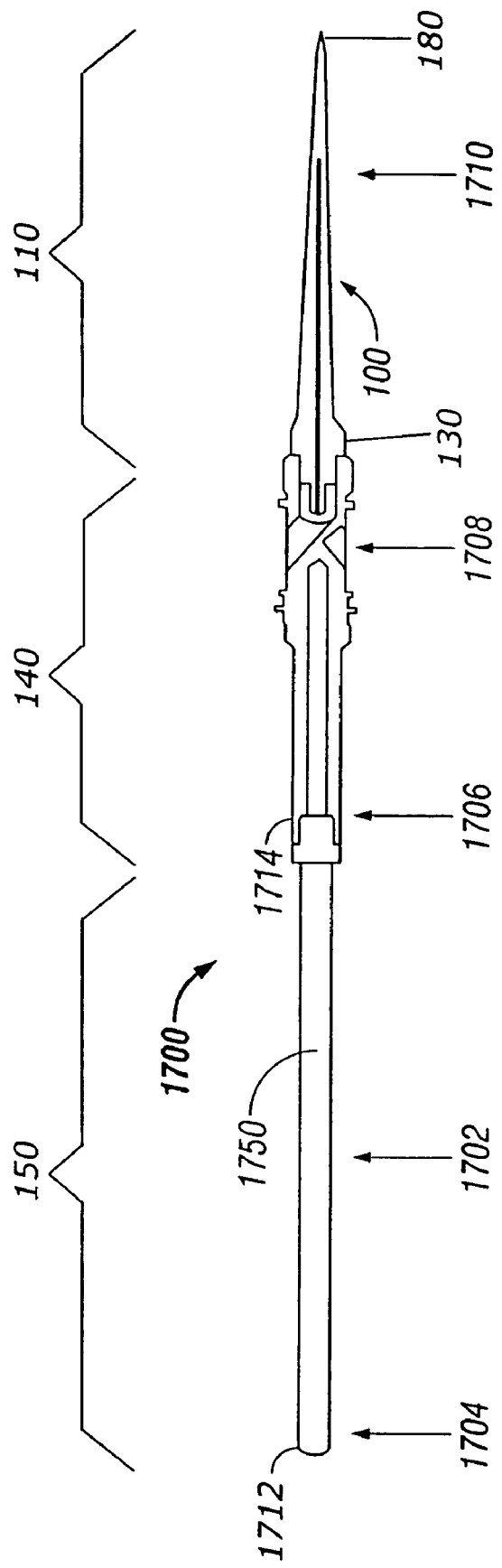
FIG. 17 is a cross-sectional view of the ultrasonic horn of FIGS. 1A, 1B through FIG. 6 showing node and antinode locations corresponding to the experimental data of FIG. 16.

FIG. 17 illustrates ultrasonic horn 100 having a nominal resonant frequency of 23 kHz in an ultrasonic horn assembly 1700 which incorporates connecting body 140 and ultrasonic resonator 150. Resonator 150 has a core stack 1750. Based on the data of blocks 2a and 2b of FIG. 16, ultrasonic horn assembly 1700 has a node 1702 at about the center of core-stack 1750 of resonator 150, where displacement is zero. Core-stack 1750 has somewhat symmetric antinodes 1704 and 1706 near a proximal end 1712 and distal end 1714, where displacement is about maximum. Given node 1702 at the center of core-stack 1750, next node would be expected with about a λ/2, spacing. It should be noted that the acoustic velocities of the constituent elements of core stack 1750 and connecting body 140 are different, and the geometry of connecting body 140 is quite complex. Next node 1708 occurs nearer to the interface between connecting body 140 and proximal end 172 (FIG. 1A) of ultrasonic horn adapter 130. Next antinode 1710 is located in the vicinity of distal end 180 of tip 190 (FIG. 5) of ultrasonic horn 100, such that all the strain in the horn is utilized in maximizing horn displacement.

It should be noted that the definition of nodes, their locations, and types are not as simple as often exclaimed or shown in the prior art. One of the issues complicating the definition and location of nodes and antinodes is that more than one mode (resonant frequency) exists for an ultrasonic horn assembly such as ultrasonic horn assembly 1700. The 23 kHz ultrasonic horn assembly for example has four substantial modes over the range of 10,000 Hz to 50,000 Hz. The generator creates a condition where the 23 kHz mode is dominant by employing a self-sustaining bandwidth limited oscillator. Without an active filter in the amplifier, the ultrasonic horn assembly could resonate at the incorrect frequency. The additional modes are overtones or undertones, and not harmonics. Even with a simple geometry, the modes are not integral multiples of frequency and the nodes are not located at exact fractional wavelengths. Each mode may contribute one or more nodes and antinodes depending on the frequency and geometry. A further complication is that the nodes may have different characteristics. For example, some nodes may have a displacement of zero but first and second derivatives of zero or other than zero. The geometry is very complex, and not simply a rod or bar, exponential, or Gaussian, which can be exactly represented mathematically. The acoustic velocities of the constituent materials of the core-stack 1750, connecting body 140, and tip 190 (FIG. 5) are different, and it may be intuitive that this may impact simple fractional wavelength spacing. The determination of allowable resonant frequencies and node locations is not simple, but if one can write equations for each of the constituent elements, and solve the roots of the overall equation (mathematically or graphically), the modes and approximate location of nodes can be determined, within the extent of the accuracy of the geometrical representation. Alternatively, the previously mentioned PRO/Mechanica or a similar FEA package can be used to perform modal analysis, and the relative nodes of zero displacement can be monitored in simulations. It is this simulation that is exhibited in FIG. 17.

Figure 18:
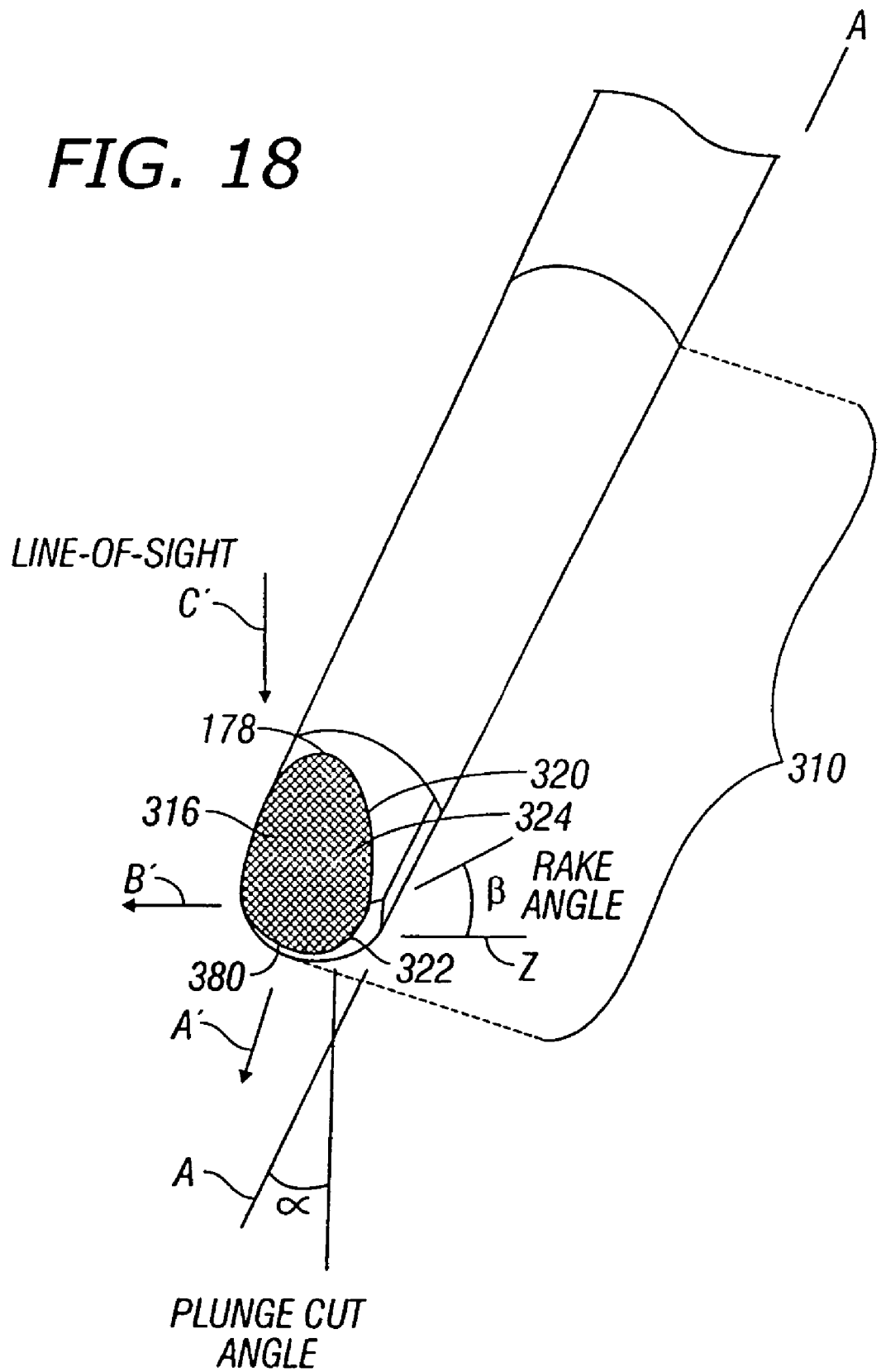
FIG. 18 is a partial perspective view of an ultrasonic horn in accordance with yet another embodiment of the present disclosure.
Figure 19:
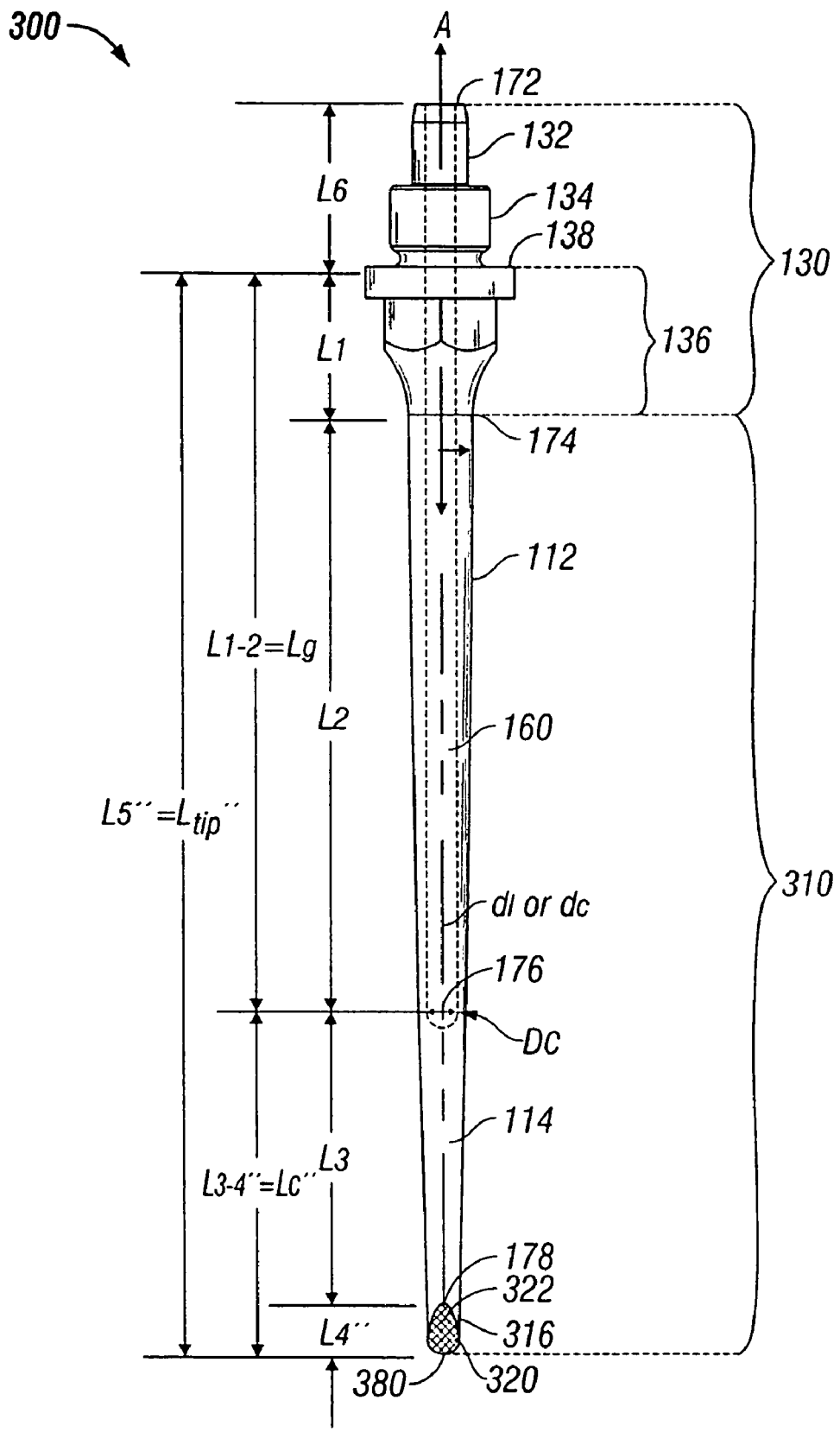
FIG. 19 is a cross-sectional view of the ultrasonic horn of FIG. 17 together with a resonator for activating the ultrasonic horn.
Figure 20:
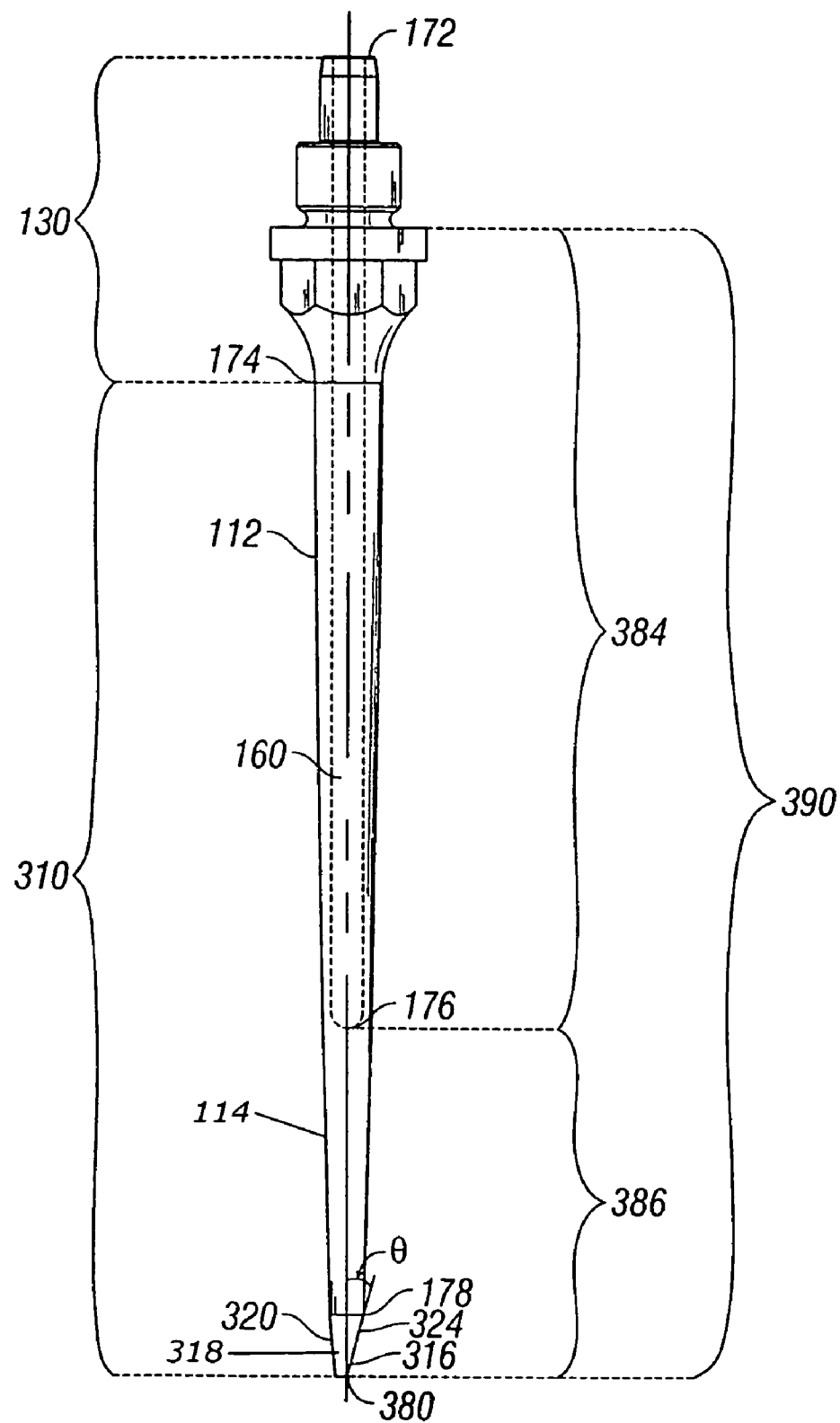
FIG. 20 is a top view of the ultrasonic horn of FIG. 17 with a channel shown in phantom.

In one embodiment of the present disclosure, FIGS. 18-20 illustrate an ultrasonic horn 300 having a tip lead 320 of elongated member 310 at a distal end 380. Ultrasonic horn 300 is otherwise identical to ultrasonic horns 100 and 200 previously described except that tip lead 320 includes a first surface 324 which is substantially flat or planar while a second or opposing surface 318 substantially follows the contour of solid portion 114 of elongated member 310 whose radius R is formed according to an inverse exponential profile distribution.

More particularly, dimension L3 is the length of solid portion 114 of elongated member 310 whose radius R is formed according to an inverse exponential profile distribution. Length L3 of solid portion 114 of elongated member 310 extends from approximately second or distal end 176 of channel or central hole 160 to first or proximal end 178 of elongated member 310 at tip lead 320. Dimension L4" corresponds to the length of chisel and awl tip lead 320 and is the length of a solid portion 316 of elongated member 310 extending from first end 178 of elongated member 310 at tip lead 320 to second end 380 of elongated member 310 at tip lead 310. Elongated member 310 is thereby a completely solid mass from intermediate point 176 to second end 380. Therefore, tip lead 320 extends from first or proximal end 178 to second or distal end 380 of elongated member 310. Radius R", or more correctly, height Y", of tip lead 320 forms surface 324 according to a unilateral tangential or linear profile distribution such that $Y''=x \tan \theta''$. That is, height Y" is proportional to the tangent of angle θ. L5" is the total length of ultrasonic horn 100 extending from first or proximal end 172 of adapter 130 to second or distal end 380 of elongated member 310 and is equal to the sum of L1, L2, L3 and L4". When ultrasonic horn 300 is connected to connecting portion 140, channel 160 extends through connecting portion 140 and ends before the resonator 150 (FIG. 1A). Tip 390 is defined as the portion of ultrasonic horn 300 extending distally from leading edge 138 of flange 136 to distal end 180.

As best shown in FIG. 18, substantially flat surface 324 is formed at an angle α with respect to the centerline A-A to enable a plunge cut direction A'. The plunge cut angle α enables a line-of-sight C' by the user directly to the targeted object. In addition, the substantially flat surface 324 is formed at a rake angle β with respect to lateral axis Z. Rake angle β provides clearance to access underlying tissue. Substantially flat surface 324 is formed of an abrasive mill-file structure so that surface 324 supports lateral abrasion, as indicated by arrow B'. However, in other embodiments, surface 324 may have alternative abrading surfaces well known in the art, for example a diamond coated surface.

Distal end 380 of tip lead 320 has a semi-circular planar surface configuration 322, such that distal end 380 of ultrasonic horn 300 is in the form of a chisel and an awl. As discussed previously, tip 380 of ultrasonic horn 300 is blunt or dull. The existing blunt edge is about 0.0125 mm (0.005 inches) wide. The boring of holes with ultrasonic horn 300 is better facilitated with slightly semi-circular manual motion; however plunge cuts in bone and wood have been accomplished with just longitudinal motion. As discussed before with respect to ultrasonic horns 100 and 200, the combination of the chisel and awl distal end 380 of horn 300 supports defined cutting or abrasion of sections, planes, notches, grooves, and holes in bone. In particular, chisel and awl distal end 380 of ultrasonic horn 300 in combination with the abrasive mill-file structure of surface 324 is particularly useful for orthopedic surgery and neurosurgery.

Figure 21:
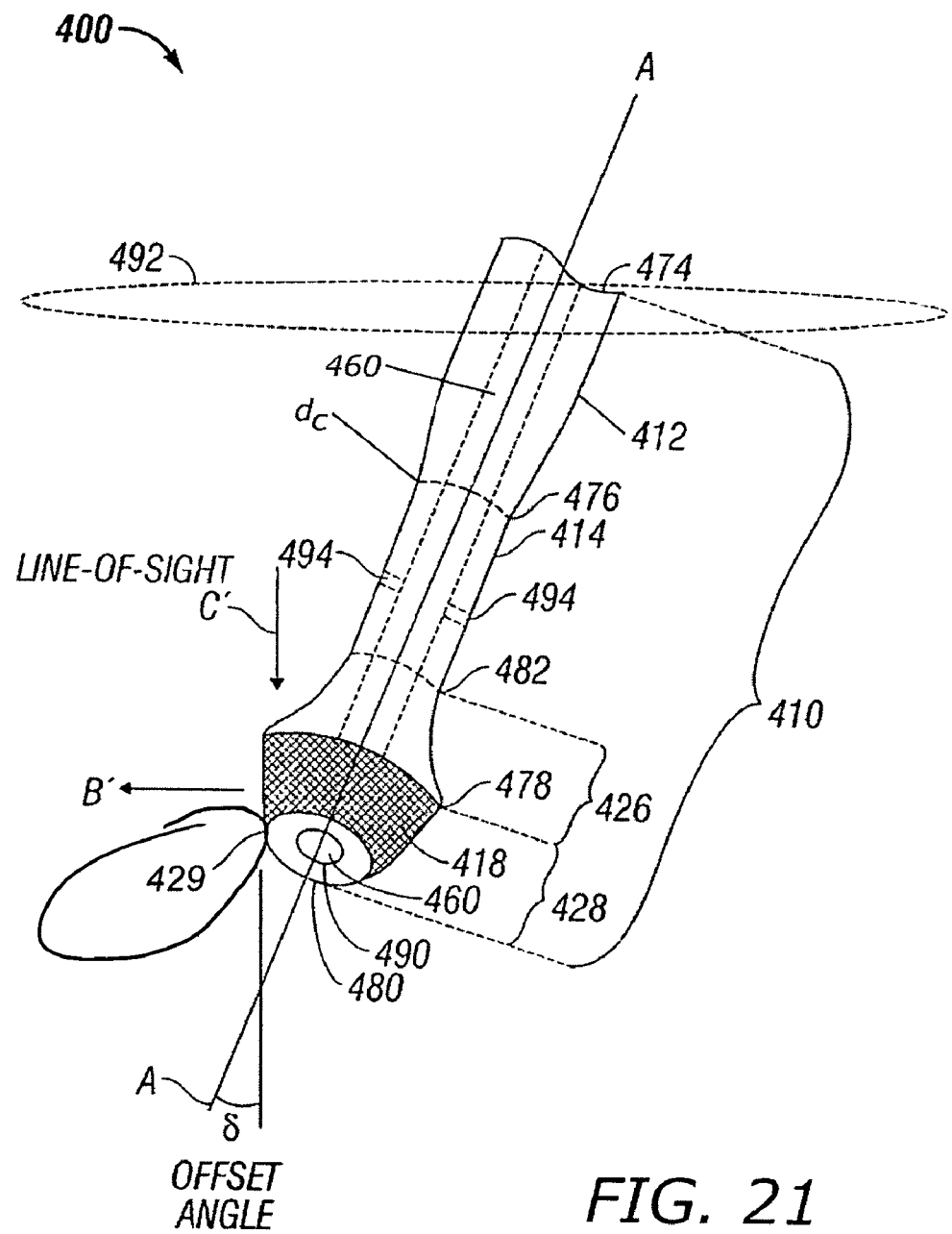
FIG. 21 is a partial perspective view of an ultrasonic horn in accordance with still another embodiment of the present disclosure.

In one embodiment of the present disclosure, FIG. 21 illustrates an ultrasonic horn 400 having a tip lead 428 of elongated member 410 at a second or distal end 480. Ultrasonic horn 400 is otherwise identical to ultrasonic horns 100, 200 and 300 previously described. More particularly, elongated member 410 extends from a first or proximal end 474 and includes a first hollow portion 412 extending distally to a first intermediate point 476 distal to a user between which first hollow portion 412 of elongated member 410 has a Gaussian profile. From first intermediate point 476, elongated member 410 includes a second hollow portion 414 extending distally to a second intermediate point 482 distal of first intermediate point 476 between which second hollow portion 414 of elongated member 410 has a straight or constant diameter profile. Constant diameter profile corresponds to small diameter $d_c$ of the Gaussian profile at first intermediate point 476. From second intermediate point 482, elongated member 410 includes a third hollow portion 426 extending distally to a third intermediate point 478 distal of second intermediate point 482 between which third hollow portion 426 of elongated member 410 has a flared exponential profile. From third intermediate point 478, elongated member 410 includes a fourth hollow portion 428 extending distally to a generally planar distal end 480 of elongated member 410 between which fourth hollow portion 428 of elongated member 410 has an inverse conical profile. Fourth hollow portion 428 having an inverse conical profile forms a tip of elongated member 410, with tip 429 extending from third intermediate point 478 to distal end 480 of elongated member 410. Tip 429 includes an abraded outer surface 418 formed according to the inverse conical profile. A substantially constant diameter channel 460 is formed within elongated member 410 by the hollow portions. Channel 460 extends from proximal end 474 through first hollow portion 412 having a Gaussian profile, through second hollow portion 414 having a straight or constant diameter profile of the small diameter of Gaussian portion 412, through third hollow portion 426 having a flared exponential profile, and through fourth hollow portion or tip 429 to distal end 480. Channel 460 has an aperture 490 at distal end 480.

Although not shown specifically in FIG. 21, ultrasonic horn 410 is also configured with an adapter such as adapter 130 in FIGS. 1A and 2-6, and may similarly be connected to a connecting body 140 and a resonator 150, as shown therein. When ultrasonic horn 400 is connected to connecting portion 140, channel 460 extends through connecting portion 140 ending before resonator 150.

Conical surface 418 is formed at an offset angle δ with respect to centerline A-A to enable a line-of-sight C' by the user directly to the targeted object. In addition, inverse conical surface 418 is formed of an abrasive mill-file structure so that surface 418 supports lateral abrasion, as indicated by arrow B'. It should be noted that the mill-file structure can be machined over the full 360° of the distal end, or limited to suit particular surgical requirements, e.g., in one embodiment, the abrasive structure is machined over less than 120°.

Figure 22:
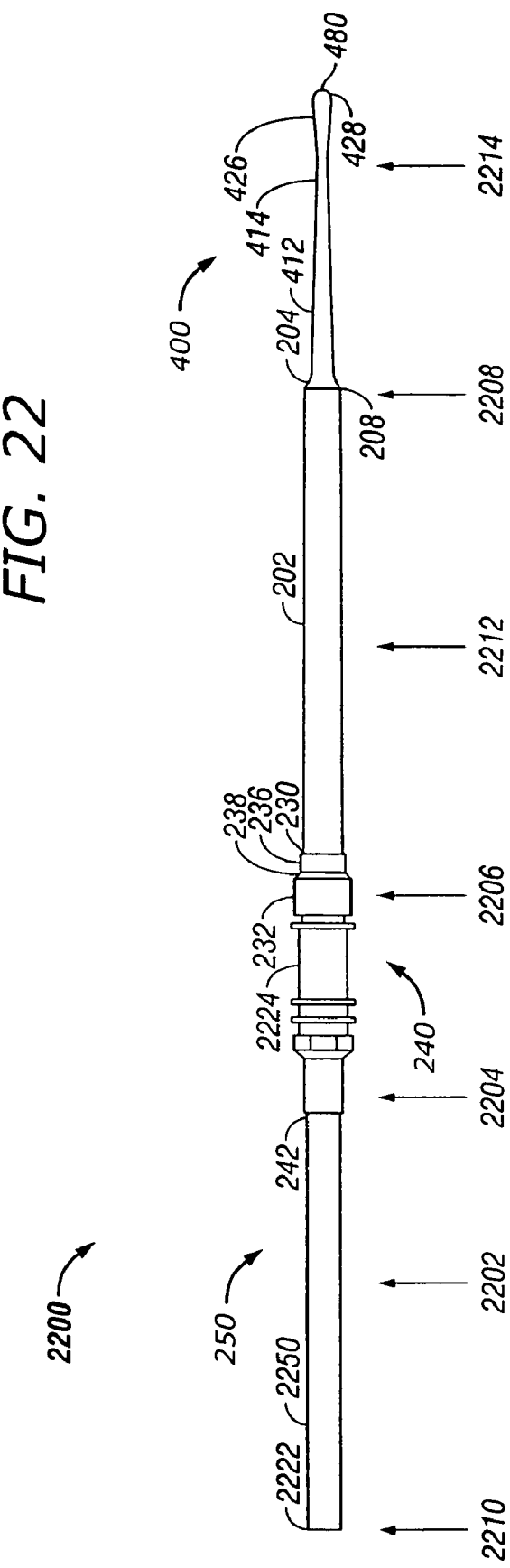
FIG. 22 is a profile view of the ultrasonic horn of FIG. 21 further having an extension member and showing node and antinode locations resulting from an experimental analysis analogous to that which resulted in the experimental data of FIG. 16.

Therefore, as compared to ultrasonic horns 100, 200 and 300, ultrasonic horn 400 differs in that channel 460 extends entirely through elongated member 410, whereas channel 160 extends only to intermediate point 176 (See FIGS. 3-6) where a transition occurs between the Gaussian profile of hollow portion 112 and the inverse exponential profile of solid portion 114. In addition, elongated member 410 includes a straight or constant diameter section portion 414, flared exponential portion 426 and inverse conical portion 428 as compared to opposing surfaces 118a and 118b of tip lead 120. In one embodiment, the major diameter of the inverse conical fourth portion 428 at the third intermediate point 478 is less than about 3 mm and inverse conical surface 418 is formed at an offset angle δ of about 10°. Other diameters and offset angles may be used. Through the modeling, simulation, and initial manufacturing phase, the major diameter of less than 3 mm and offset angle δ of less than 10° has been maintained. The offset angle δ may be increased to provide alternative line of sight options for other procedures. An opening 492 in a patient's body through which ultrasonic horn 400 is used generally has to be larger for greater offset angles. FIG. 22 illustrates ultrasonic horn 400 of FIG. 21 further including extension member 202 and having a nominal resonant frequency of 36 kHz in an ultrasonic horn assembly 2200 and which incorporates connecting body 240 and ultrasonic resonator 250. As previously described herein, the extension member 202 can be a straight circular cylinder or tube or be curved to 13° or less.

FIG. 22 further illustrates node and antinode locations resulting from an experimental analysis analogous to that which resulted in the experimental data of FIG. 16. More particularly, resonator 250 encloses a core stack 2250. Resonator 250 has a proximal end 2222 and a distal end 2224. Ultrasonic horn assembly 2200 has a node 2202 just distal of the center of core-stack 2250 of resonator 250, where displacement is zero. Node 2202 is not exactly on center because it is influenced by more than the simple geometry of core-stack 2250. Core-stack 2250 contributes to an antinode 2204 within proximal end 242 of connecting body 240, where displacement is about maximum. Next node 2206 is at flange 236 of adapter 230 and just beyond threads of leading edge 238 of flange 236 mating adapter 230 to connecting body 240. Again, it should be noted that the acoustic velocities of the constituent elements are different, and the geometry of connecting body 240 is quite complex. Next node 2208 occurs proximal of and in the vicinity of distal end 208 of extension member 202. Distal end 208 coincides with the proximal end of flared transition member 204. An antinode 2210 occurs at proximal end 2222 of ultrasonic resonator 250. Another antinode 2212 occurs in extension member 202 about midway between nodes 2206 and 2208. At the straight or constant diameter portion 414 in proximity to distal end 480 of ultrasonic horn 400 is yet another antinode 2214, such that all the strain in horn assembly 2200 is utilized in maximizing horn displacement.

In one embodiment, FIG. 21 illustrates pre-aspiration apertures or holes 494 formed through the walls on opposing sides of straight or constant diameter second portion 414. Pre-aspiration apertures 494 of elongated tip portion 410 may be employed in conjunction with channel 460, which, as previously noted, extends from proximal end 474 through first hollow portion 412 having a Gaussian profile, through second hollow portion 414 having a straight or constant diameter profile of the small diameter of Gaussian portion 412, through third hollow portion 426 having a flared exponential profile, and through fourth hollow portion or tip 428 to distal end 480. An example is the CUSA EXcel™ 36 kHz Model Curved Extended Micro Tip, C4611 (See the 2005 CUSA EXcel™ Ultrasonic Surgical Aspirator Product Catalog by Tyco Healthcare LP; www.radionics.com/products/cusa/cusa-catalog.pdf). The pre-aspiration holes 494 can be optionally used to suction a portion of the irrigation liquid employed through the channel to aid in cooling the tip. The pre-aspiration holes 494 can also reduce misting caused by cavitation at the distal end of tip, thereby improving viewing via endoscopes or microscopes.

In terms of applications, ultrasonic horn 400 and ultrasonic horn assembly 2200 are particularly useful for cranial-based surgery, where opening 492 is larger than when performing transsphenoidal or endoscopic-nasal approaches.

Figure 23:
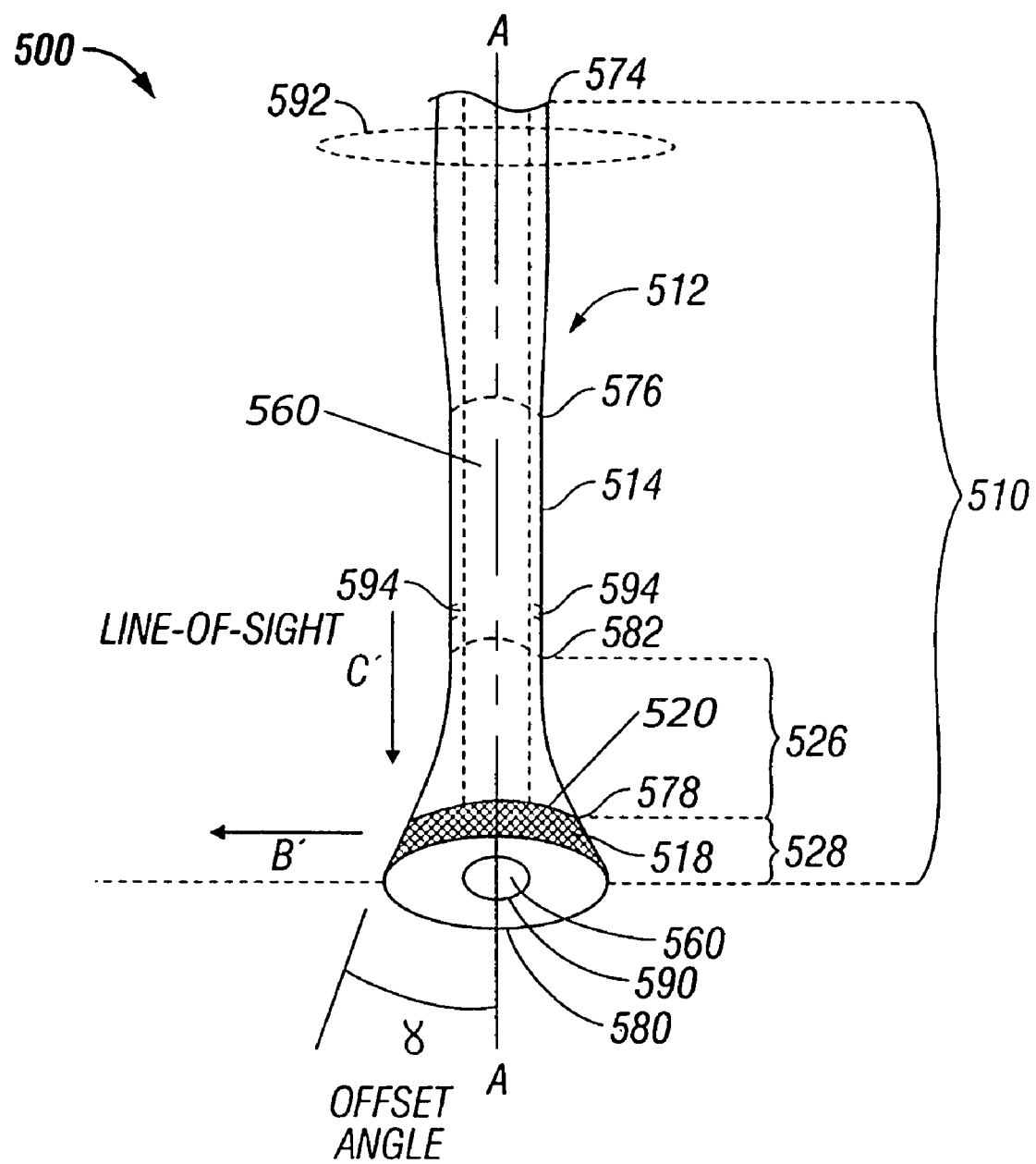
FIG. 23 is a partial perspective view of an ultrasonic horn in accordance with still yet another embodiment of the present disclosure.
Figure 24:
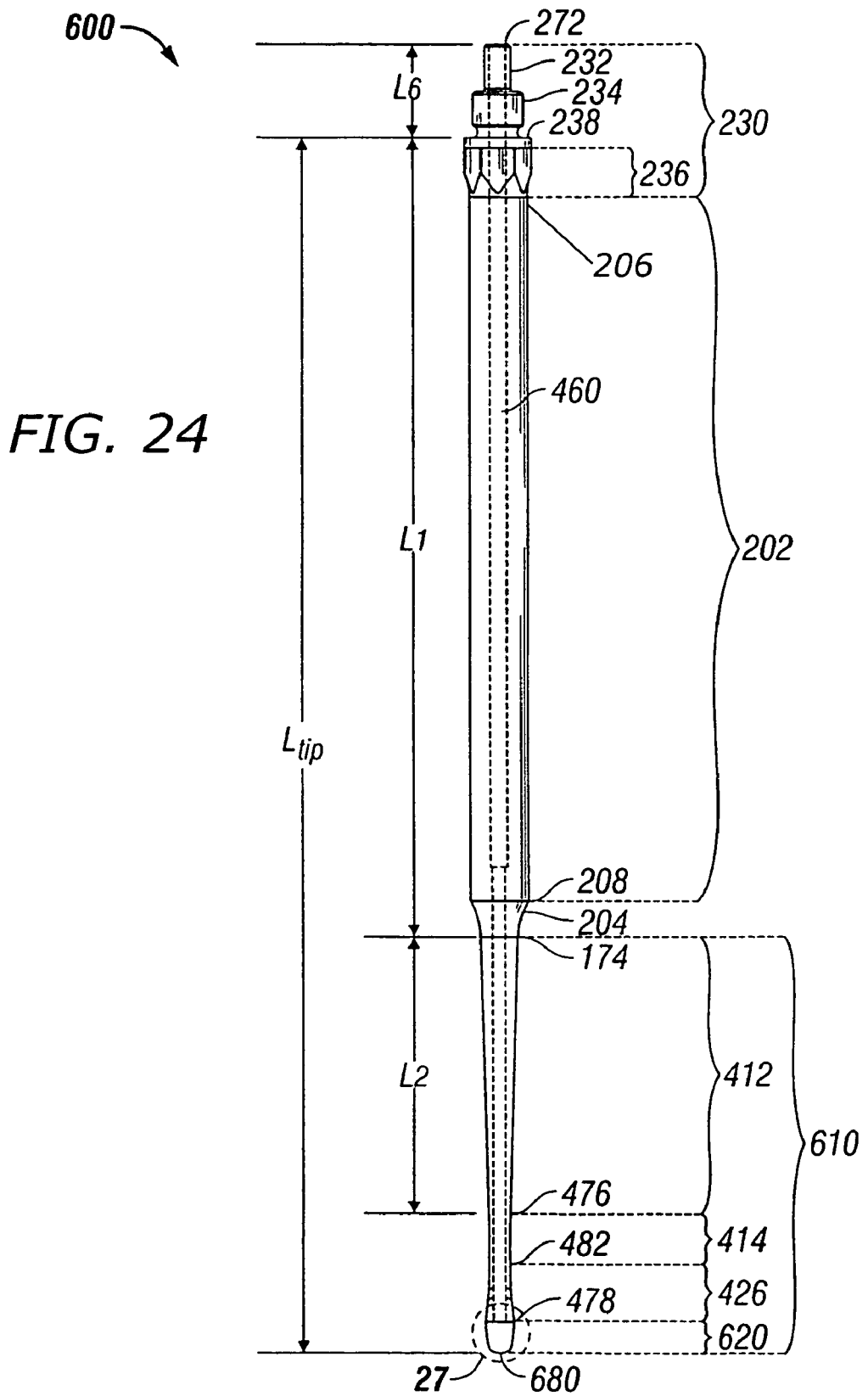
FIG. 24 is a bottom view of an ultrasonic horn in accordance with yet another embodiment of the present disclosure.
Figure 25:
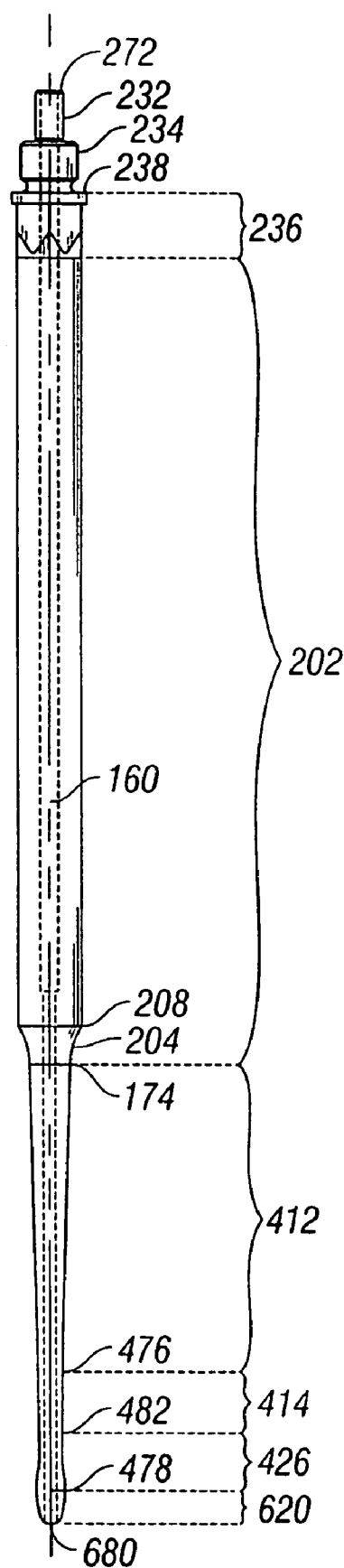
FIG. 25 is a side view of the ultrasonic horn of FIG. 24.

In one embodiment of the present disclosure, FIG. 23 illustrates an ultrasonic horn 500 having a tip 520 of elongated member 510 at a second or distal end 580. Ultrasonic horn 500 is otherwise identical to ultrasonic horn 400 previously described. More particularly, elongated member 510 extends from a first or proximal end 574 and includes a first hollow portion 512 extending distally to a first intermediate point 576 distal to a user between which first hollow portion 512 of elongated member 510 has a Gaussian profile. From first intermediate point 576, elongated member 510 includes a second hollow portion 514 extending distally to a second intermediate point 582 distal of first intermediate point 576 between which second hollow portion 514 of elongated member 510 has a straight profile of the small diameter of the Gaussian. From second intermediate point 582, elongated member 510 includes a third hollow portion 526 extending distally to a third intermediate point 578 distal of second intermediate point 582 between which third hollow portion 526 of elongated member 510 has a flared exponential profile. From third intermediate point 578, elongated member 510 includes a fourth hollow portion 528 extending distally to a generally planar second or distal end 580 of elongated member 510 between which fourth hollow portion 528 has a conical profile. Fourth hollow portion 528 having a conical profile forms a tip of elongated member 510, with tip 528 extending from third intermediate point 578 to distal end 580 of elongated member 510. Tip 528 includes an abraded outer surface 518 formed according to the conical profile. A substantially constant diameter channel 560 is uniformly formed within elongated member 510 by the four hollow portions 512, 514, 526 and 528. Channel 560 extends from proximal end 574 through hollow portion 512 having a Gaussian profile, through the hollow portion 514 having a straight or constant diameter profile of the small diameter of Gaussian portion 512, through hollow portion 526 having a flared exponential profile, and through tip 528 to distal end 580. Channel 560 has an aperture 590 at distal end 580.

Although not shown specifically in FIG. 23, ultrasonic horn 510 is also configured with an adapter such as adapter 130 in FIGS. 1A and 2-6, and may similarly be connected to a connecting body 140 and a resonator 150, as shown therein. When ultrasonic horn 500 is connected to connecting portion 140, channel 560 extends through connecting portion 140 and ends before resonator 150.

Conical surface 518 is formed at an angle γ with respect to centerline A-A to enable a line-of-sight C' by the user directly to the targeted object. In addition, conical surface 518 is formed of an abrasive mill-file structure so that surface 518 supports lateral abrasion, as indicated by arrow B'. When the abrasive surface 518 is brought normal to the bone, the proximal end 574 rotates out of the line of sight. In at least one other embodiment, one of many abrasive surfaces known in the art may be substituted for the mill-file structure. One example of another abrasive surface is a diamond coated surface.

Therefore, as compared to ultrasonic horns 100, 200 and 300, ultrasonic horn 500 also differs in that channel 560 extends entirely through elongated member 510, whereas channel 160 extends only to intermediate point 176 (See FIGS. 3-6) where a transition occurs between the Gaussian profile of hollow portion 112 and the inverse exponential profile of solid portion 114. In addition, elongated member 510 includes a straight section 514, having a straight or constant diameter profile. Constant diameter profile corresponds to small diameter $d_c$ of the Gaussian profile at first intermediate point 576. Elongated member 510 also includes flared exponential portion 526 and conical portion 530 as compared to opposing surfaces 118a and 118b of tip lead 120.

In one embodiment, the major diameter of conical fourth portion 528 at third intermediate point 578 is less than about 4 mm-and conical surface 518 is formed at an offset angle γ of about 10°. Other diameters and offset angles may be used. It is envisioned that the offset angle γ may include values as large as 45°. In terms of applications, ultrasonic horn 500 is particularly useful for transsphenoidal or endoscopic-nasal approaches. In comparing an opening 592 required for access with the lateral abrasion surface normal to a bone for horn 500 embodied in FIG. 23 to required opening 492 for horn 400 in FIG. 21, it is clear that the innovation of horn 400 in FIG. 21 enables passage and operation through a small opening, such as employed in approaching tumors for removal through the nose. In particular, an endoscope employed in the same nostril or inserted into a second nostril, and located just in back of the flared exponential, would provide the line-of-sight necessary. Additionally, these transsphenoidal and endoscopic nasal approaches often require further opening of bony cavities, such as in the sphenoid sinus. It has been observed that when the openings are extended with a manual tool such as a Kerrison or manual cutting device, the bone fractures in an unpredictable way, often leading to excessive bleeding. The horn in FIG. 23, would readily facilitate operation via a passage of less than about 4 mm, support line-of-sight viewing of the area under operation with an adjacent endoscope, and provide controlled abrasion for marginally opening bony cavities.

In one embodiment, FIG. 23 illustrates pre-aspiration apertures or holes 594 formed through the walls on opposing sides of straight or constant diameter second portion 514. Pre-aspiration apertures 594 of elongated tip portion 510 may be employed in conjunction with channel 560, which, as previously noted, extends from proximal end 574 through first hollow portion 512 having a Gaussian profile, through second hollow portion 514 having a straight or constant diameter profile of the small diameter of Gaussian portion 512, through third hollow portion 526 having a flared exponential profile, and through fourth hollow portion or tip 528 to distal end 580. Again, an example is the CUSA EXcel™ 36 kHz Model Curved Extended Micro Tip, C4611 (See the 2005 CUSA EXcel™ Ultrasonic Surgical Aspirator Product Catalog by Tyco Healthcare LP; www.radionics.com/products/cusa/cusa-catalog.pdf). The pre-aspiration holes 594 can be optionally used to suction a portion of the irrigation liquid employed through the channel to aid in cooling the tip. The pre-aspiration holes 594 can also reduce misting caused by cavitation at the distal end of tip, thereby improving viewing via endoscopes or microscopes.

In another embodiment of the present disclosure, as seen in FIGS. 24 to 27, another ultrasonic horn 600 is provided. In at least one embodiment, ultrasonic horn 600 is particularly suited for a resonant frequency of about 23 kHz. In at least one other embodiment, ultrasonic horn 600 is particularly suited for a different resonant frequency (i.e., about 36 kHz). Ultrasonic horn 600 is similar to ultrasonic horns 200 and 400 as described previously with respect to FIGS. 11, 12 and 21, and thus will only be described in detail herein to the extent necessary to identify differences in construction and operation. Similar to ultrasonic horns 200 and 400, ultrasonic horn 600 includes an adapter 230 having a proximal end 272 and a distal end which coincides with proximal end 206 of extension member 202. Again, extension member 202 has a proximal end 206 and a distal end 208. Adapter 230 includes, extending distally from proximal end 272, a fillet 232, a nut 234 and a flange 236 terminating at proximal end 206 of extension member 202. Length L6 is the length of fillet 232 and nut 234 from proximal end 272 of adapter 230 to leading edge 238 of flange 236. A flared member 204 is disposed at proximal end 174 of elongated member 610 and at distal end 208 of extension member 202. Adapter 230 and flared member 204 are, in one embodiment, unitarily connected to extension member 202.

As noted previously, extension member 202 is shown as a straight circular cylinder or tube. However, in commercially available embodiments, such as the CUSA EXcel™ 36 kHz Model Curved Extended Micro Tip, C4611 (See the 2005 CUSA EXcel™ Ultrasonic Surgical Aspirator Product Catalog by Tyco Healthcare LP; www.radionics.com/products/cusa/cusa-catalog.pdf), this extension member can be curved. Constant diameter channel 460 extends through adapter 230, extension member 202 and flared member 204. Outer diameter of extension member 202 is substantially constant and is greater than outer diameter $D_{g^o}$ of elongated member 610 at proximal end 174. Therefore, flared member 204 forms a transition member between outer diameter of extension member 202 and outer diameter $D_{g^o}$ of elongated member 610 at proximal end 174. Dimension L1' is the length along central longitudinal axis A extending distally from leading edge 238 of adapter 230, extension member 202 and flared member 204, to distal end 174 of flared member 204.

Ultrasonic horn 600 further includes an elongated member 610 extending from distal end 174 of flared member 204 to second or distal end 680 of tip lead 620. Elongated member 610 extends from distal end 174 of flared member 204 to tip lead 620 at second or distal end 680. Elongated member 610 includes first hollow portion 412 extending distally to first intermediate point 476. First hollow portion 412 has a Gaussian profile. From first intermediate point 476, elongated member 610 includes second hollow portion 414 extending distally to second intermediate point 482. Second hollow portion 414 has a straight or constant diameter profile. The constant diameter profile corresponds to small diameter d, of the Gaussian profile at first intermediate point 476. From second intermediate point 482, elongated member 610 includes a third hollow portion 426 extending distally to third intermediate point 478. Third hollow portion 426 has a flared exponential profile.

Figure 27:
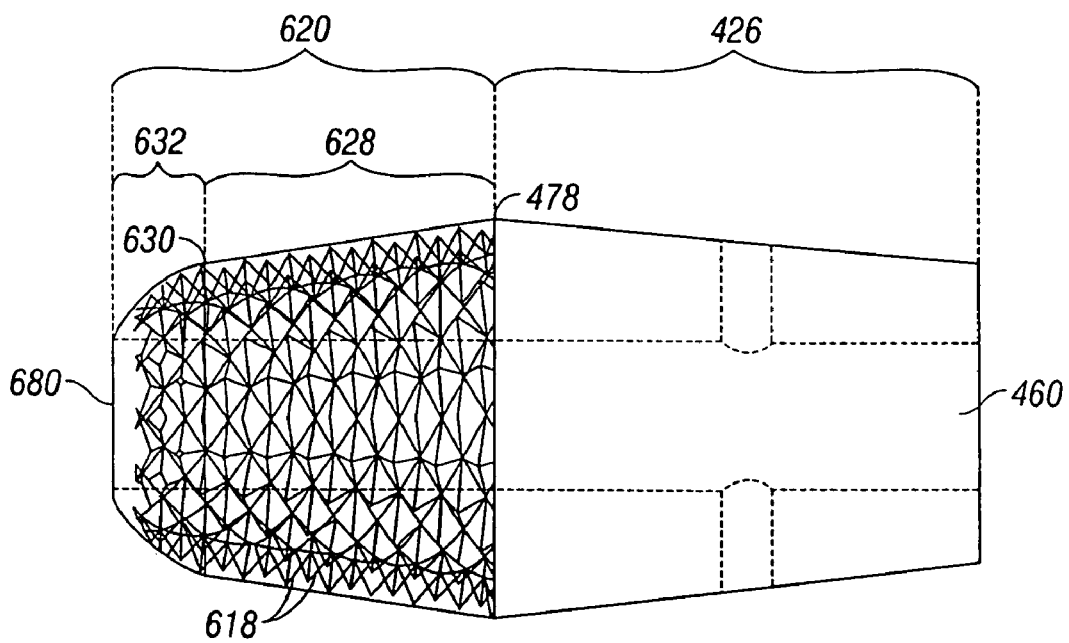
FIG. 27 is an enlarged view of the indicated area of detail of the ultrasonic horn of FIG. 24.

As seen in FIG. 27, the tip lead 620 extends from third intermediate point 478 through a fourth hollow portion 628 (see FIG. 27) extending distally to a fourth intermediate point 630. Tip lead 620 further includes a fifth hollow portion 632 extending distally from fourth intermediate point 630 to distal end 680. In at least one embodiment, distal end 680 is planar in configuration. Channel 460 extends entirely through elongated member 610 to distal end 680 and defines an aperture 490 at the distal end 680. In at least one embodiment, the channel 460 has substantially the same diameter within the extension member 202 and the elongated member 610. In at least one other embodiment, the channel 460 within the extension member 202 has a different sized diameter than the channel 460 within the elongated member. The fourth hollow portion 628 has an inverse conical profile while fifth hollow portion 632 has an inverse curvilinear or tapering profile.

As seen in FIGS. 24-27, both the fourth portion 628 and the fifth portion 632 include an abraded region 618 formed in or on an outer surface thereof. In at least one embodiment, the abrasive surface/adraded region is formed according to the respective profiles of the fourth and fifth portions 628 and 632. In particular, the abraded surface or region 618 is formed on the fourth portion 628 and conforms to the inverse conical profile thereof and is formed on the fifth portion 632 and conforms to the inverse curvilinear or tapering profile thereof. In one embodiment, the abraded region or surface 618 is formed of an abrasive mill-file structure so that region or surface 618 is capable of lateral and/or longitudinal abrasion. In at least one other embodiment, the abraded region or surface 618 may be formed of other abrasive surfaces well known in the art.

As previously described with respect to FIGS. 10A to 12, proximal end 272 of adapter 230 is configured to connect to a connecting portion 240 which is disposed in proximity to proximal end 272 of adapter 230. A proximal end 242 of connecting portion 240 is configured to connect to a distal end of a resonator 250. Again, as is the case with resonator 150, resonator 250 includes, in one embodiment, a magnetostrictive transducer, although other transducer types can be included such as a piezoelectric transducer. Resonator 250 is supplied power from a generator (not shown) such that resonator 250 operates at a desired resonant frequency, such as in the range of 36,000 Hz (36 kHz). Those skilled in the art will recognize that the lengths of ultrasonic horn 600 are determined in the same manner as determined for ultrasonic horns 100 and 200, taking into consideration connecting body 240 and resonator 250 which are designed for a resonant frequency of about 36 kHz. In other embodiments, the lengths of ultrasonic horn 600 may be varied whereby the ultrasonic horn is designed to operate at other resonant frequencies.

Figure 26:
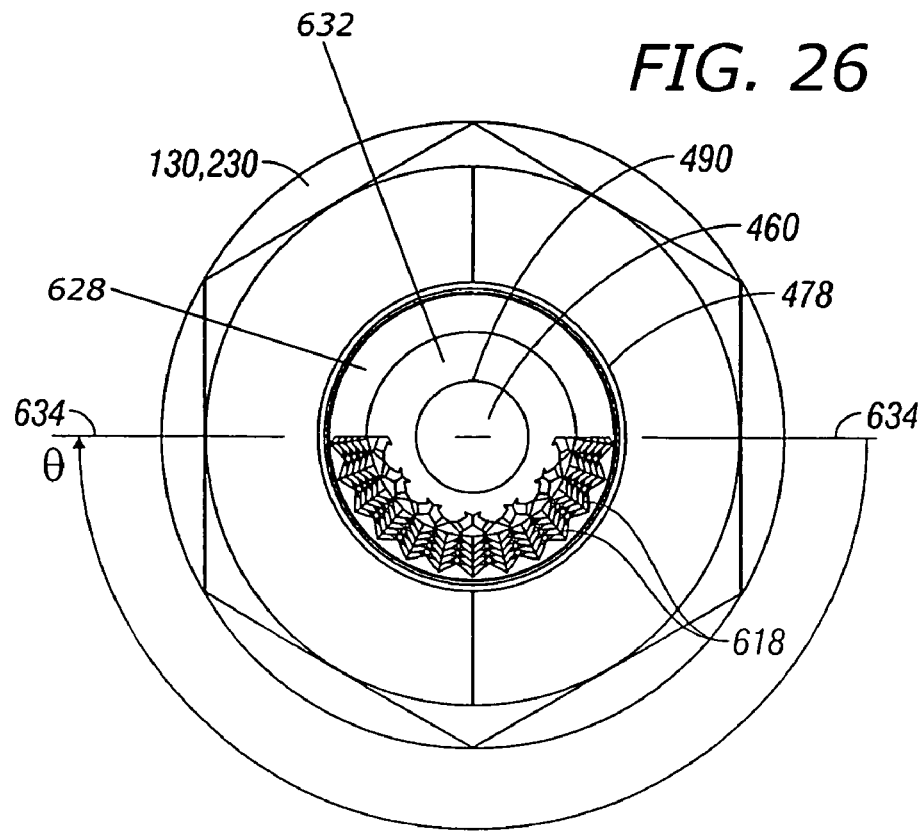
FIG. 26 is a distal end view of the ultrasonic horn of FIGS. 24 and 25.

As best illustrated in FIGS. 26 and 27, the abraded region or surface 618 extends circumferentially or radially around the fourth and fifth portions 628 and 632 to form an arc represented by angle θ which is approximately limited by border lines 634. In one embodiment, as seen in FIG. 26, the angle θ is about 180 degrees.

Figure 28:
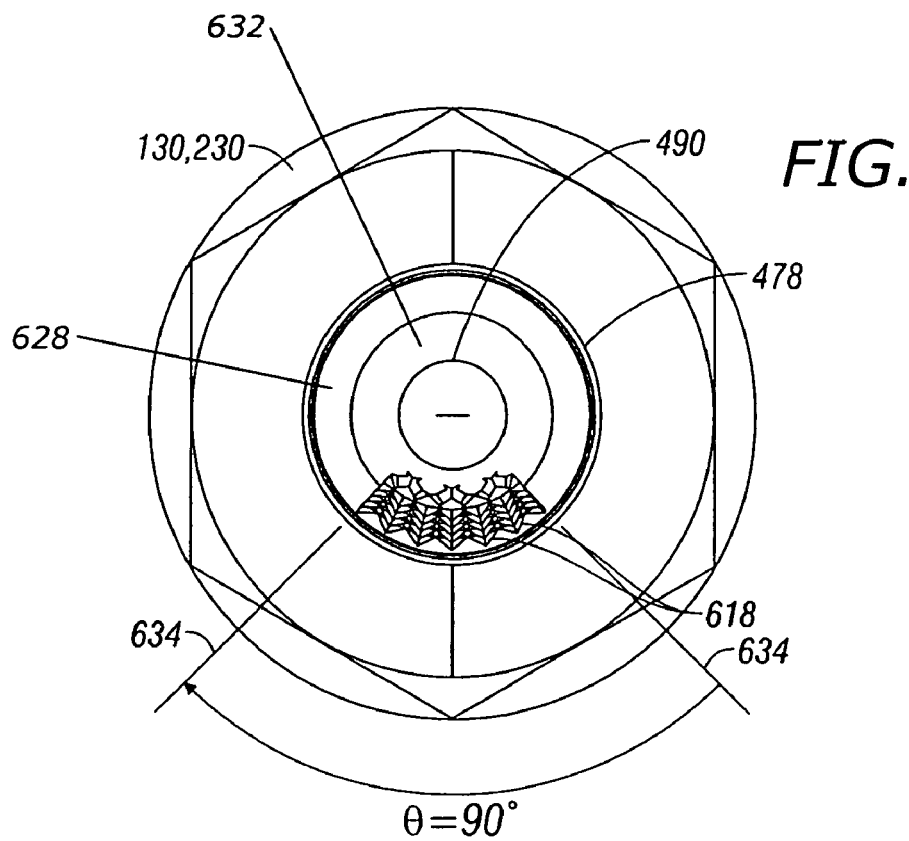
FIG. 28 is a distal end view of a variation of the embodiment of the ultrasonic horn of FIGS. 24-27.

In yet another embodiment, as seen in FIG. 28, the abraded region or surface 618 extends circumferentially around the fourth and fifth portions 628 and 632 to form an arc limited by border lines 634 such that the angle θ is about 90 degrees.

Figure 29:
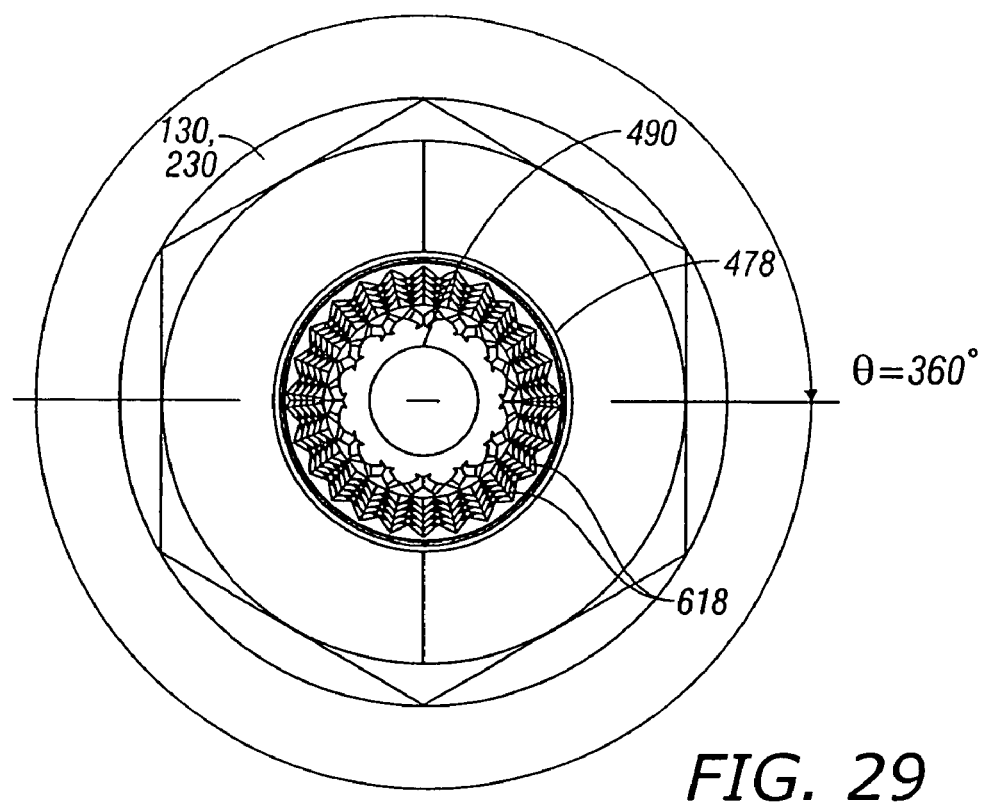
FIG. 29 is a distal end view of another variation of the embodiment of the ultrasonic horn of FIGS. 24-27.

In still another embodiment, as seen in FIG. 29, the abraded surface 618 extends circumferentially around the fourth and fifth portions 628 and 632 to form an arc substantially entirely around the circumference such that the angle θ is about 360 degrees. Those skilled in the art will recognize that various values for the angle θ may be provided according to the intended function of the ultrasonic horn 600. The embodiments are not limited in this context.

Figure 30:
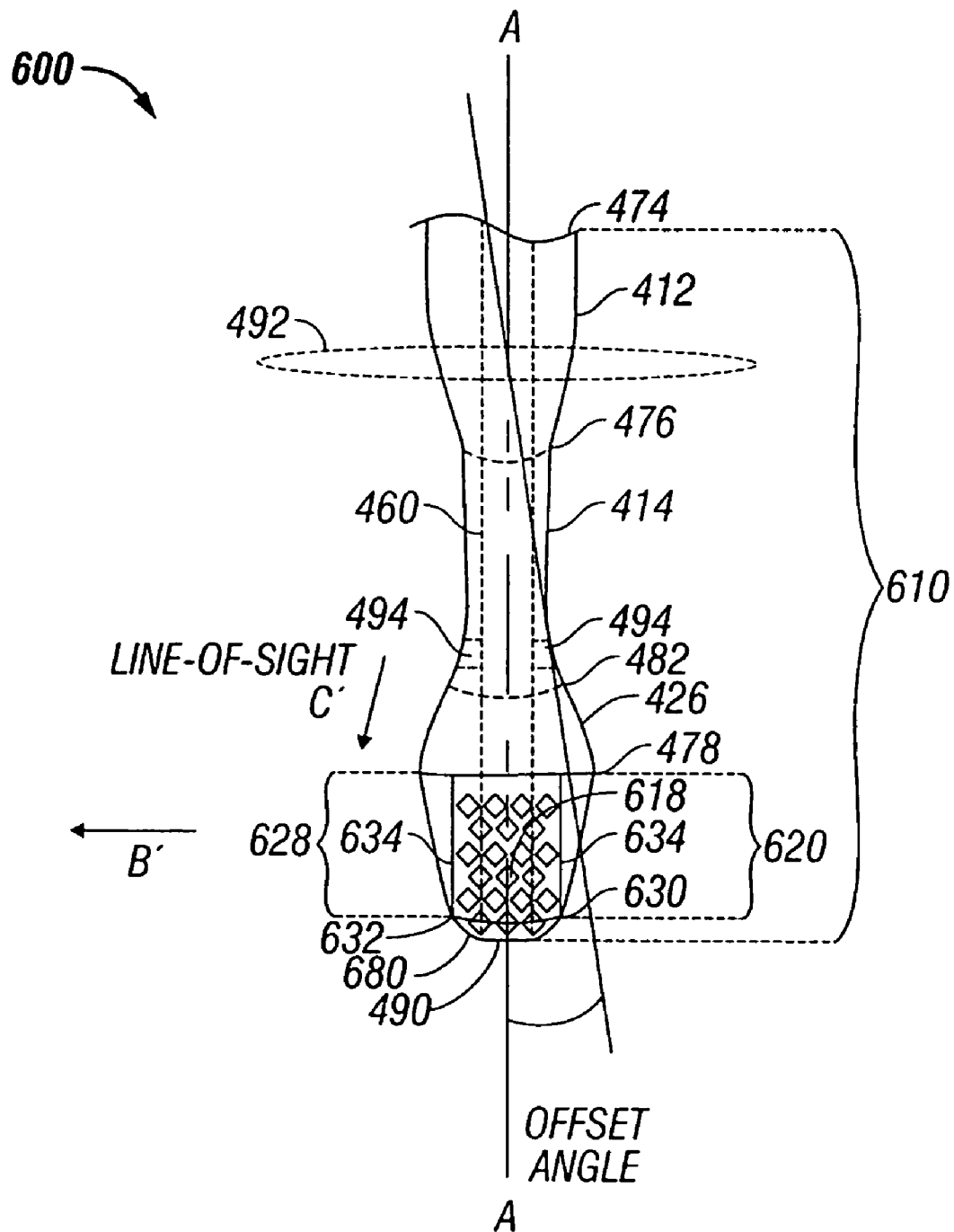
FIG. 30 is a partial perspective view of the ultrasonic horn of FIG. 28.

FIG. 30 shows the ultrasonic horn 600 of FIG. 28 wherein the angle θ is about 90 degrees. The abraded region 618 supports lateral abrasion, as indicated by arrow B', as well as longitudinal abrasion. More particularly, abraded region 618 is formed at offset angle δ with respect to centerline A-A to enable a line-of-sight C' by the user directly to the targeted object. In addition, since abraded surface 618 is formed of an abrasive mill-file structure, surface 618 supports lateral abrasion, as indicated by arrow B'.

Figure 31:
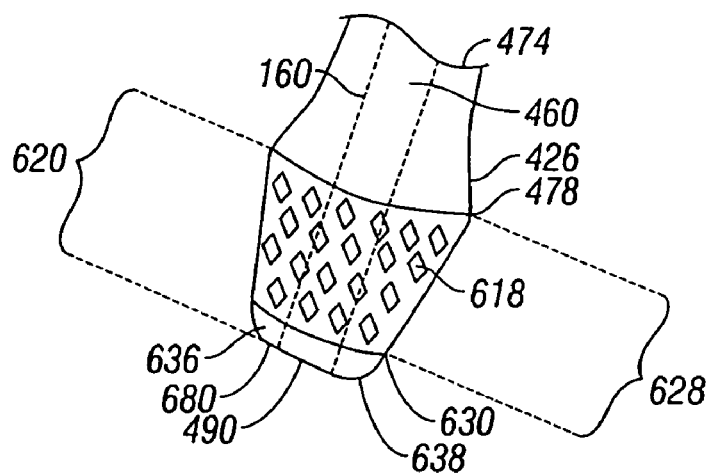
FIG. 31 is a partial perspective view of an ultrasonic horn in accordance with still another embodiment of the present disclosure.

In one embodiment, as seen in FIG. 31, an ultrasonic horn 700 similar to ultrasonic horn 600 (FIGS. 24-30) is provided. Unlike the fifth hollow portion 632 (see FIG. 27) of ultrasonic horn 600 which includes a portion of the abraded region 618, the fifth hollow portion 636 of ultrasonic horn 700 includes an inverse curvilinear or tapering profile having a substantially smooth surface 638. In at least one embodiment, while the abraded surface 618 extends circumferentially around the fourth portion 628 to form an arc substantially entirely around the circumference such that the angle θ is about 360 degrees, the fifth hollow portion 632 (see FIG. 27) of ultrasonic horn 600 which includes the abraded surface 618 is replaced by a fifth hollow portion 636 having an inverse curvilinear or tapering profile but which is characterized by a substantially smooth surface 638. The fifth hollow portion 636 extends distally from fourth intermediate point 630 to the distal end 680.

Figure 32:
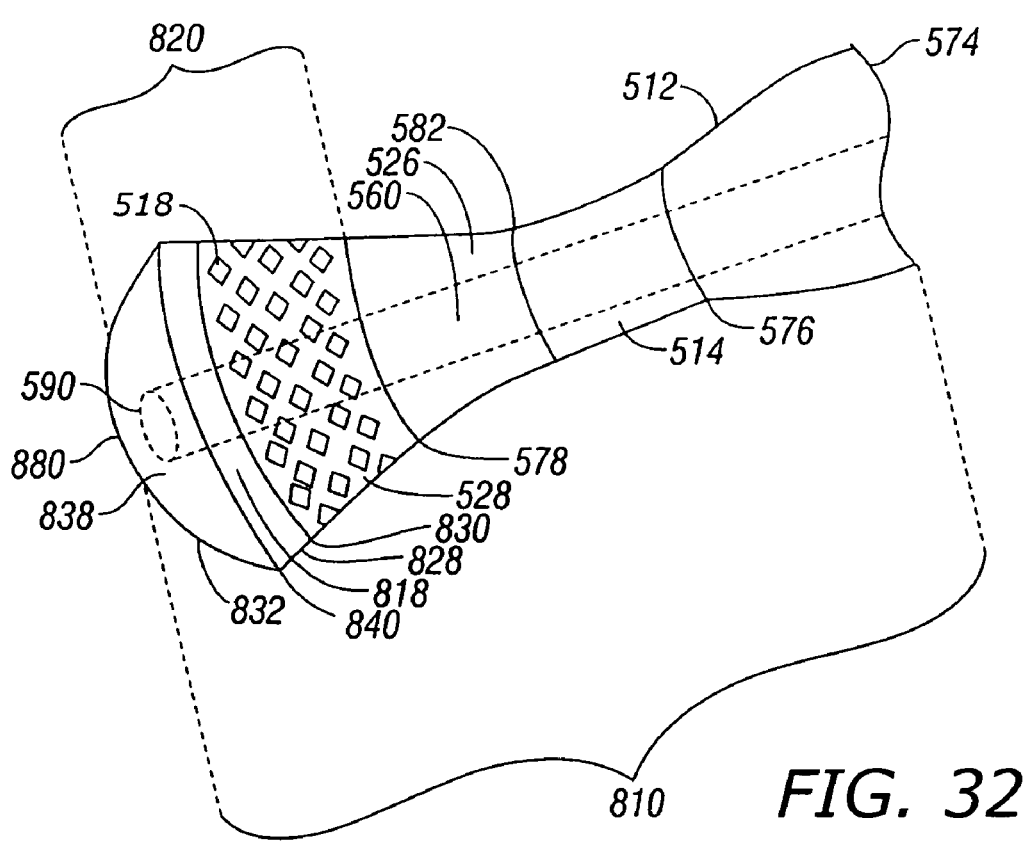
FIG. 32 is a partial perspective view of an ultrasonic horn in accordance with yet another embodiment of the present disclosure.

Referring now to FIG. 32, in another embodiment an ultrasonic horn 800 similar to ultrasonic horns 100, 200 and 500 (FIG. 23) is provided. Ultrasonic horn 800 has a tip lead 820 terminating at second or distal end 880. Ultrasonic horn 800 includes an elongated member 810 which extends from first or proximal end 574 and includes first hollow portion 512 extending distally to first intermediate point 576. The first hollow portion 512 has a Gaussian profile. From first intermediate point 576, elongated member 810 includes a second hollow portion 514 extending distally to a second intermediate point 582. Second hollow portion 514 has a straight profile of the small diameter of the Gaussian. Similarly to ultrasonic horn 500, from second intermediate point 582, elongated member 810 includes third hollow portion 526 which extends distally to third intermediate point 578. Third hollow portion 526 has a flared exponential profile.

Ultrasonic horn 800 further includes a tip lead 820, extending distally from third intermediate point 578, and terminating at second or distal end 880. Elongated member 810 includes a fourth hollow portion 528 extending distally to a fourth intermediate point 830. Fourth hollow portion 528 has a conical profile. The fourth hollow portion 528 has an abraded region 518 formed in an outer surface thereof. In at least one embodiment, the abraded region 518 is a mill-file outer surface. In other embodiments, the abraded region 518 may be other abrasive structures well known in the art.

In one embodiment, abraded region 518 extends substantially entirely around the circumference of the fourth hollow portion 528. In one embodiment, it is envisioned that the abraded region or surface 518 of fourth hollow portion 528 may have a mill-file structure. A fifth hollow portion 828 extends distally from fourth intermediate point 830 to a fifth intermediate point 840. The fifth hollow portion 828 has a conical profile and has a substantially smooth outer surface 818. Ultrasonic horn 800 further includes a sixth hollow portion 832 which extends distally from fifth intermediate point 840 to distal end 880. The sixth hollow portion 832 has an inverse curvilinear or tapering profile and a substantially smooth outer surface 838.

Figure 33:
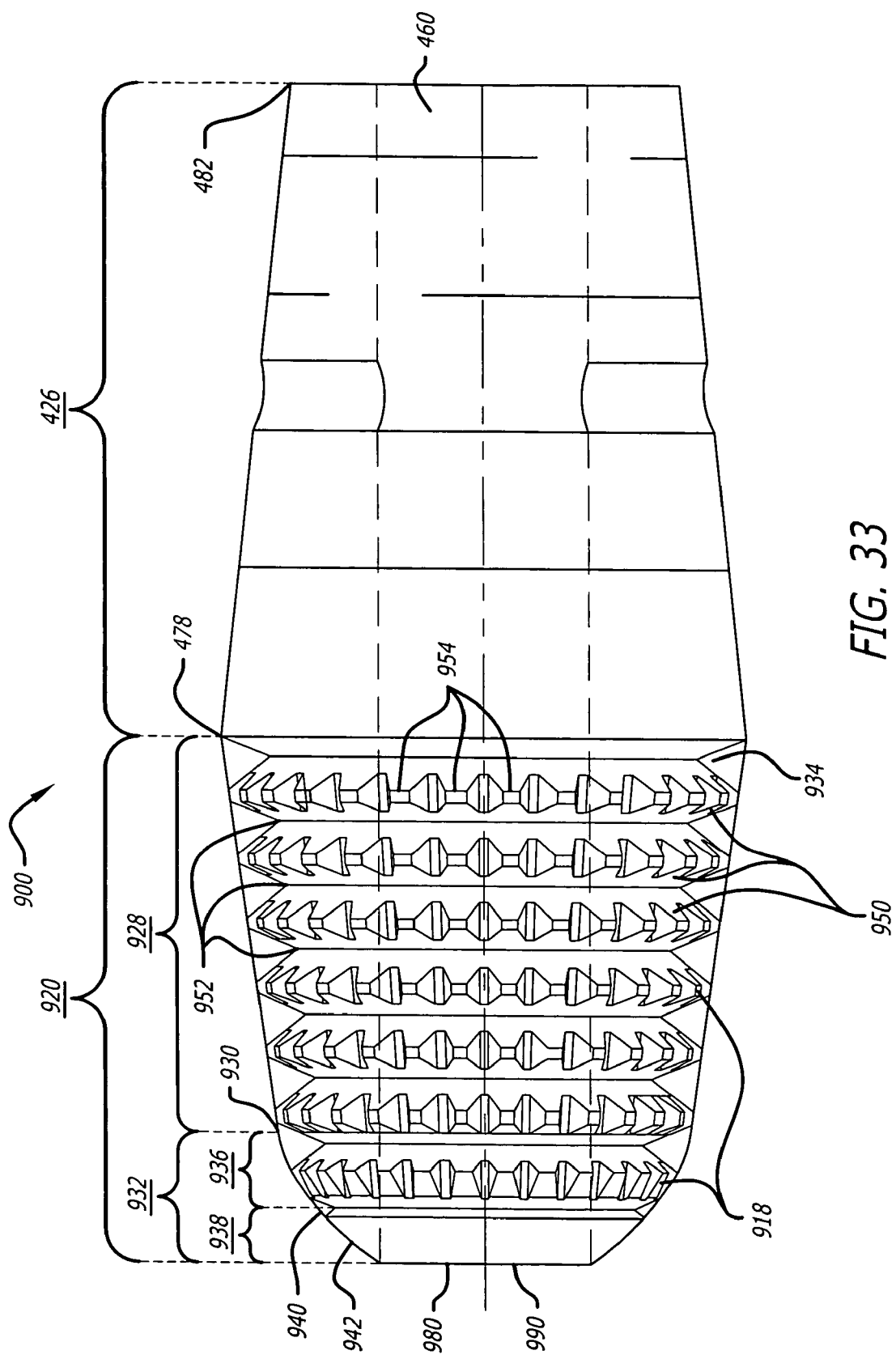
FIG. 33 is an enlarged view of the area of detail of the ultrasonic horn of FIG. 24 illustrating a variation thereto.
Figure 34:
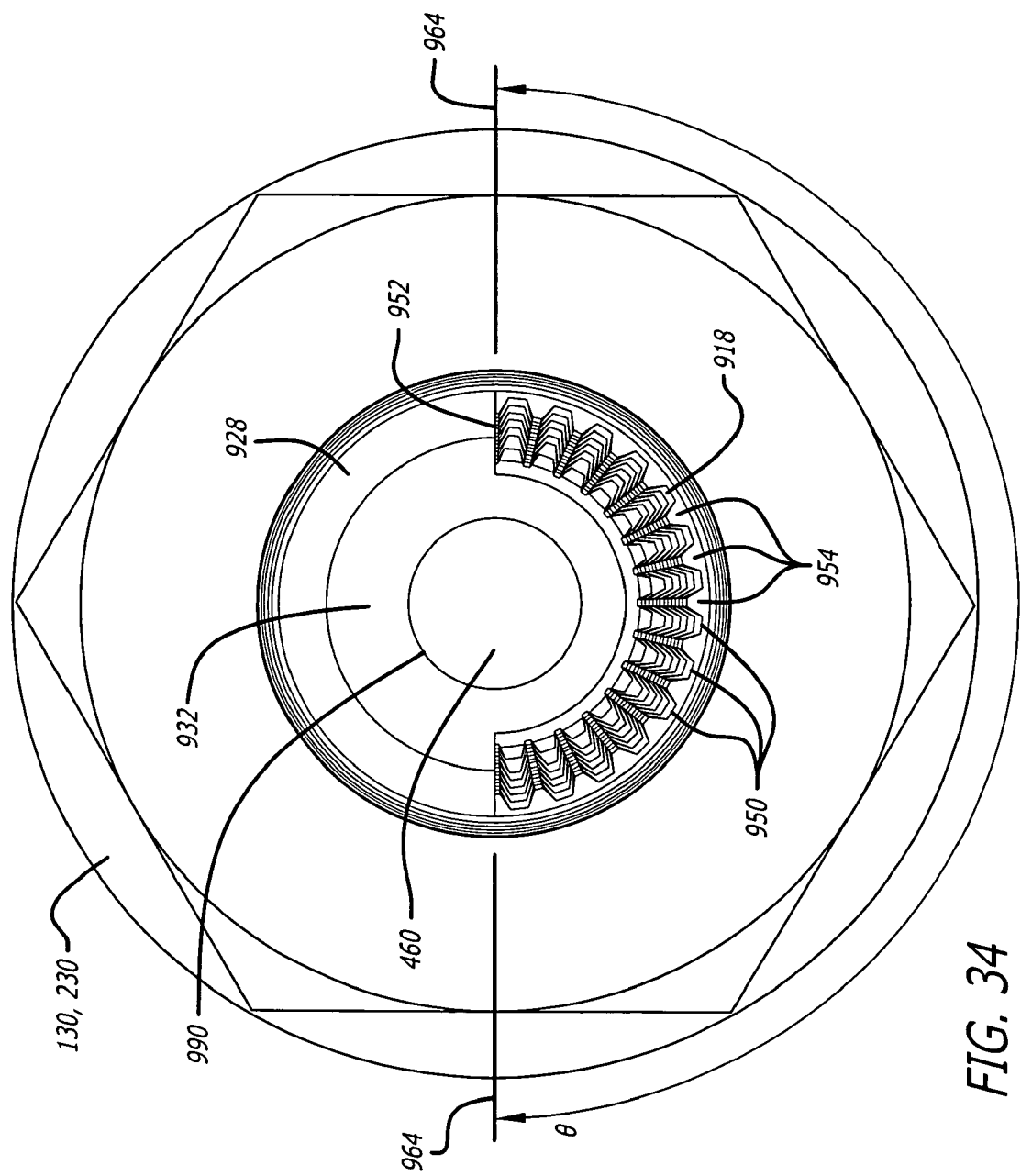
FIG. 34 is a distal view of the ultrasonic horn of FIG. 33.

Turning now to FIGS. 33 and 34, an alternate embodiment of the ultrasonic horn 600 is shown and described and is generally designated as 900. In one embodiment, ultrasonic horn 900 is also particularly suited for operation and/or use at a resonant frequency of, for example, 36 kHz. In other embodiments, ultrasonic horn 900 may be configured for use at other resonant frequencies. Ultrasonic horn 900 is similar to ultrasonic horn 600 and thus will only be described herein to the extent necessary to identify differences in construction and operation.

Ultrasonic horn 900 includes a tip lead 920 including a fourth hollow portion 928 which extends from third intermediate point 478 through to a fourth intermediate point 930. Ultrasonic horn 900 further includes a fifth hollow portion 932 extending distally from fourth intermediate point 930 through to distal end 980. Channel 460 extends entirely through third hollow portion 426 and tip lead 920 to distal end 980 where channel 460 defines an aperture 990. The fourth hollow portion 928 has an inverse conical profile while fifth hollow portion 932 has an inverse curvilinear or tapering profile.

As seen in FIG. 33, both the fourth portion 928 and the fifth portion 932 include an abraded region 918 formed in or on an outer surface thereof and which conforms to the respective profiles of the fourth and fifth portions 928 and 932. In particular, the abraded region 918 conforms to the inverse conical profile of the fourth portion 928 and conforms to the inverse curvilinear or tapering profile of the fifth portion 932.

In an embodiment, the abraded region 918 is formed only on a proximal part 936 of the fifth portion 923. The proximal part 936 extends from fourth intermediate point 930 to a fifth intermediate point 940. A distal part 938 of fifth portion 932 extends from fifth intermediate point 940 to distal end 980. In an embodiment, the distal part 938 includes a substantially smooth outer surface 942.

As seen in FIGS. 33 and 34, the abraded region 918 of ultrasonic horn 900 is formed form an array of pyramidal or pyramid-shaped protrusions 950 which are aligned both transversely and linearly with respect to the longitudinal centerline of the ultrasonic horn 900. Protrusions 950 are defined by a plurality of transverse grooves 952 and longitudinal grooves 954 formed in the surface of tip lead 920. It is envisioned that the transverse grooves 952 are orthogonally oriented with respect to the longitudinal grooves 954.

In an embodiment, the depth of the transverse grooves 952 may exceed the depth of the longitudinal grooves 954. The protrusions 950 may be truncated so as to define flattened tips or surfaces.

As best illustrated in FIG. 34, the abraded region 918 may extend circumferentially or radially around the fourth and fifth portions 928 and 932 to form an arc represented by angle θ which is approximately limited by border lines 964. As seen in FIG. 34, the angle θ is about 180 degrees. However, the angle θ may be set at other values such as 90 degrees and 360 degrees, as shown in FIGS. 28 and 29, respectively. In at least one embodiment, the angle θ is between zero degrees and 360 degrees.

The pyramid-shaped protrusions 950 are therefore configured to support lateral and/or longitudinal abrasion.

Therefore, it can be appreciated that numerous embodiments of the ultrasonic horns according to the present disclosure are possible according to the intended function desired.

The 23 kHz devices manufactured readily removed bone at even low (40%) amplitude settings of the CUSA™ with little physical force by the surgeon, better relying on the fragmentation of the material with concentrated ultrasound and resultant mechanical forces. With the new horn, cutting and abrasion of bone was effective going with or across the apparent grain of bone, and on edge of sectioned bone. Irrigation liquid (e.g. saline) is continuously provided via a polymer flue surrounding the horn, as is done with the ultrasonic aspiration horns. With optional settings of the CUSA™, the concentrated ultrasound is also observed to promote cavitation in the liquid at the relatively blunt or dull surface of the cutting end of the chisel, thereby better supporting material removal without a sharpened end like a wood plane or scalpel. A sharpened end could chip, and also be a hazard to tissue even when not ultrasonically excited, such as in transiting a nasal cavity. Along with amplitude control, the selectivity feature of the commercially available CUSAM, which limits reserve power, can be utilized to remove very fine layers of bone with the chisel, more like monolayers or planes. The low-quiescent power of the new horn afforded by the profile is as low as the commercially available ultrasonic aspiration horns that do not have solid distal ends. The low quiescent power of the new horn, as shown in initial data to be less than 20 Watts, affords adjustment of reserve power from a few Watts to as great as 80 Watts. Bulk removal of bone is readily accomplished with well defined cutting or abrasion of sections, planes, notches, grooves, and holes in bone. A wide range of cutting or abrasion capability is available based on settings of amplitude and reserve power.

The device described is just one embodiment of the use of the inverse exponential profile with the Gaussian and solid distal end geometry. Of course, straight extenders of multiple quarter wavelengths between the threaded end and Gaussian are often employed to make the horns longer. These can be readily employed with the present invention, for example, as discussed previously with respect to the embodiment of the present disclosure of ultrasonic horn 200 and the corresponding FIGS. 10A, 10B through 14. Therefore, if extension 202 is of a length such as λ/2, the resonant frequency of ultrasonic assembly of resonator 250, connecting body 240 and ultrasonic horn 200 is not substantially changed or affected by the presence of extension 202. Again, it should be noted that the extension member, 202, is shown as a straight circular cylinder or tube. However, in commercially available embodiments, such as the CUSA EXcel™ 36 kHz Model Curved Extended Micro Tip, C4611 (See the 2005 CUSA EXcel™ Ultrasonic Surgical Aspirator Product Catalog by Tyco Healthcare LP; www.radionics.com/products/cusa/cusa-catalog.pdf), this extension member 202 can be curved. Embodiments of the present invention, for example ultrasonic horn 500 disclosed herein, can be readily manufactured with curved extension members of about 13° or less. The curved extender affords improve line-of-sight to the distal end by removing the connecting body and resonator further from the field of view. It should also be noted that the horn design is not unique to magnetostrictive transducers; therefore, piezoelectric devices could be used. It should be apparent that alternative solid distal end geometries, such as more blunt ends with abrasive surfaces or flared horns, etc, could be similarly constructed.

It can be seen therefore that the embodiments of the present disclosure provide an Ampulla (Gaussian) to inverse exponential to chisel/awl distal end profile which affords mechanical gain and propagation of ultrasound with minimal errant reflection and standing waves that could limit transmitted sound and reduce horn stroke amplitude. Quiescent power is similar to ultrasonic aspiration horns that do not have solid distal ends, and reserve power is far greater than is needed to readily cut or abrade bone. Along with amplitude control and the selectivity feature of the commercially available CUSA™, which limits reserve power, the ultrasonic horn of the present disclosure can be utilized to remove very fine layers of bone with the chisel, in monolayers or planes.

The ultrasonic horn with the combined chisel and awl distal end of the present disclosure used in conjunction with the CUSA™ control system, provides the fine control typically exhibited by ultrasonic abrasive devices with file-like structures, while better supporting defined cutting or abrasion of sections, planes, notches, grooves, and holes in bone. Furthermore, the new horn profile affords superior bulk removal of bone, whereas bulk removal of bone is a limitation of existing ultrasonic devices.

As compared to ultrasonic surgical instruments with file-like abrasive structures, at least one embodiment of the present invention is blunt or dull on its very end and more cone-like with a monotonically increasing diameter, thereby improving safety in insertion, and requiring minimal space. In addition, as compared to such surgical instruments, at least one embodiment of the present invention can be optionally operated such that the concentrated ultrasound afforded with the chisel/awl distal end results in cavitation, the latter aiding in cutting and abrading bone. The high mechanical forces known to accompany cavitation afford work beyond simple friction and abrasion via file-like structures.

As previously discussed, the inverse exponential profile of at least one embodiment of the present disclosure with the decay parameter selected to uniquely match the Gaussian profile provides an improved horn for propagation of high amplitude ultrasound, as previously discussed. In at least one embodiment of the present invention, the profile beyond the Gaussian profile segment is greatly simplified as compared to ultrasonic horns having a tip with a multifaceted profile. The majority of the profile of the present invention can be manufactured employing automatic contour turning operations, as previously discussed. The chisel angle of at least one embodiment of the present invention is more conducive to forward propagation of ultrasound being 350, versus 45° for horns having a multifaceted tip. As a result, the ultrasonic horn of the present invention is capable of being manufactured with a simple turning operation, which is not the case with horns having a tip with a multifaceted profile.

In view of existing manually spring-activated surgical instruments used in opening or extending bony cavities such as the sinus bone cavity to access tumors in the brain, e.g., a manual device with a sharp or serrated edge that crimps bone or tenacious tissue when hand actuated, such as a Kerrison™ bone punch, the ultrasonic horns of the present invention afford improved control. With such mechanical spring-activated instruments, bone is crimped, cut, and removed. It has been observed that unpredictable fracturing may occur with crimping, which can result in severe bleeding. An alternative to the Kerrison T bone punch is specifically sought for delicately extending the openings in bony cavities. It is envisioned that the controlled extension afforded with cutting and abrasion with the embodiments of the present invention overcome these potential problems Furthermore, it has been observed that existing motorized high speed (e.g. 40,000 to 60,000 RPM) drills with diamond impregnated or fluted ball cutting ends presently used in surgical approaches may create some hazards including winding of tissue in proximity to the drill shaft and rotating ball end, whipping of critical anatomy with partially wound-up tissue, and "walking" of the ball in an uncontrolled fashion on irregular and sometimes cylindrical or wedge shaped bone surfaces. Although not all the bone removal tasks performed with these motorized drills can be envisioned for the new horn, bulk removal of bone is readily accomplished with well defined cutting or abrasion of sections, planes, notches, grooves, and holes in bone, and this capability would be better suited in some surgical sites near critical anatomy.

The ultrasonic horns of the present invention can be combined with irrigation and aspiration systems such as is disclosed in, for example, FIG. 3 of U.S. Pat. No. 6,214,017 B1 to Stoddard et al., which as noted is incorporated by reference herein in its entirety. Irrigation in the flue aids in cooling the material of the horn which is in flexure. Pre-aspiration holes may be added. The cooling capability can be enhanced by suctioning some portion of the irrigation liquid through the internal hole of the horn via pre-aspiration.

While the above embodiments of the ultrasonic horns may be described as operating at a specific target frequency, it should be understood that any of the embodiments of the ultrasonic horns of the present invention described herein may be configured to operate at a target frequency of either about 36 kHz or about 23 kHz. Furthermore, the embodiments of the ultrasonic horns of the present invention described herein may be configured to operate at other advantageous target frequencies.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

We claim:

1. An ultrasonic horn configured for use with a surgical ultrasonic handpiece having a resonator, the ultrasonic horn configured to receive ultrasonic energy and conduct the received ultrasonic energy along its length, the ultrasonic horn comprising:

an elongated member having a longitudinal centerline, a proximal end, a distal end, a first intermediate point disposed between the proximal end of the elongated member and the distal end of the elongated member, a second intermediate point disposed between the first intermediate point and the distal end of the elongated member; a third intermediate point disposed between the second intermediate point and the distal end of the elongated member, and a fourth intermediate point disposed between the third intermediate point and the distal end of the elongated member, wherein the elongated member is formed of a rigid ultrasonic energy conductive material selected such that the elongated member conducts ultrasonic energy from its proximal end to its distal end;

the elongated member having a first hollow portion having a Gaussian profile extending from the proximal end of the elongated member to the first intermediate point of the elongated member, the first hollow portion being centered along the longitudinal centerline and forming a first internal channel that has a proximal opening at the proximal end of the elongated member;

the elongated member having a second hollow portion having a straight profile extending from the first intermediate point to the second intermediate point, the second hollow portion adjoining the first hollow portion and being centered along the longitudinal centerline and forming a second internal channel that is in fluid communication with the first internal channel and thereby also being in fluid communication with the proximal end of the elongated member;

the elongated member having a third hollow portion having a flared exponential profile extending from the second intermediate point to the third intermediate point, the third hollow portion adjoining the second hollow portion and being centered along the longitudinal centerline and forming a third internal channel that is in fluid communication with the second internal channel and thereby also being in fluid communication with the proximal end of the elongated member;

the elongated member having a fourth hollow portion having an inverse conical profile extending from the third intermediate point to the fourth intermediate point, the fourth hollow portion adjoining the third hollow portion and being centered along the longitudinal centerline and forming a fourth internal channel that is in fluid communication with the third internal channel and thereby also being in fluid communication with the proximal end of the elongated member;

the elongated member having a fifth hollow portion having a tapering profile extending from the fourth intermediate point to the distal end of the elongated member, the fifth hollow portion adjoining the fourth hollow portion and being centered along the longitudinal centerline and forming a fifth internal channel that is in fluid communication with the fourth internal channel and thereby also being in fluid communication with the proximal end of the elongated member;

whereby each of the first, second, third, fourth, and fifth portions by virtue of being hollow form an outer wall in the elongated member, the outer wall conducting ultrasonic energy;

a tip lead disposed at the distal end of the elongated member formed of material of the distal end of the elongated member thereby being an integral part thereof, the tip lead including the fourth hollow portion and the fifth hollow portion, the tip lead also comprising a generally planar distal end, and an exterior surface, wherein at least a portion of the exterior surface includes an abrasive structure;

an extension member being formed of a rigid ultrasonic energy conductive material and connected to the proximal end of the elongated member by a flared member, the extension member having a proximal end and a longitudinal centerline that is an extension of the elongated member centerline;

an adapter being formed of a rigid ultrasonic energy conductive material and disposed on the proximal end of the extension member and having a proximal end configured to couple with a resonator, and having a longitudinal centerline that is an extension of and parallel with the elongated member centerline; and a continuous internal channel longitudinally disposed within all of the elongated member, the flared member, the extension member, and the adapter, wherein the internal longitudinal channel comprises the first, second, third, fourth, and fifth internal channels and is configured to form a hollow length extending from the proximal end of the adapter to the generally planar distal end of the elongated member.

2. The ultrasonic horn of claim 1, wherein the abrasive structure is a mill-file structure.

3. The ultrasonic horn of claim 1, wherein the abrasive structure is configured for lateral abrasion and longitudinal abrasion.

4. The ultrasonic horn of claim 1, wherein the ultrasonic horn is configured to operate at a target frequency of about 36 kHz.

5. The ultrasonic horn of claim 1, wherein the ultrasonic horn is configured to operate at a target frequency of about 23 kHz.

6. The ultrasonic horn of claim 1, wherein the internal channel has a constant diameter extending through the elongated member, the flared member, the extension member, and the adapter.

7. The ultrasonic horn of claim 1, wherein the internal channel has a first diameter extending through the elongated member, and a different second diameter extending through the extension member.

8. The ultrasonic horn of claim 1, wherein the adapter includes:
a distal end configured to connect with the extension member;
a fillet extending from the proximal end of the adapter;
a nut disposed between the proximal end and the distal end; and
a flange disposed on the distal end of the adapter having a leading edge configured for connecting with the extension member.

9. The ultrasonic horn of claim 1, wherein the outer diameter of the extension member is constant.

10. The ultrasonic horn of claim 1, wherein the adapter and the flared member are unitarily connected to the extension member.

11. The ultrasonic horn of claim 1, wherein an outer surface of the fourth hollow portion includes the abrasive structure and an outer surface of the fifth hollow portion has a substantially smooth surface.

12. The ultrasonic horn of claim 1, wherein at least a portion of an outer surface of the fourth hollow portion and at least a portion of an outer surface of the fifth hollow portion include the abrasive structure, the abrasive structure conforming to the profiles of the fourth hollow portion and the fifth hollow portion.

13. The ultrasonic horn of claim 12, wherein a proximal portion of the outer surface of the fifth hollow portion includes the abrasive structure.

14. The ultrasonic horn of claim 12, wherein a proximal portion of the outer surface of the fifth hollow portion includes the abrasive structure and a distal portion of the outer surface of the fifth hollow portion is substantially smooth.

15. The ultrasonic horn of claim 1, wherein the abrasive structure includes an array of pyramid shaped protrusions aligned both transversely and linearly with respect to the longitudinal centerline of the elongated member.

16. The ultrasonic horn of claim 15, wherein the abrasive structure further includes a plurality of transverse grooves and longitudinal grooves.

17. The ultrasonic horn of claim 16, wherein the transverse grooves are deeper than the longitudinal grooves.

18. The ultrasonic horn of claim 15, wherein the pyramid shaped protrusions have flattened exterior facing surfaces.

19. The ultrasonic horn of claim 1, further including pre-aspiration apertures formed through the elongated member at a location that is proximal to the tip lead and extending from the internal channel through the wall to an external surface of the elongated member.

20. The ultrasonic horn of claim 1, wherein the elongated member including the tip lead, the extension member, and the adapter are formed from a single piece of ultrasonic conducting material.

21. The ultrasonic horn of claim 1, wherein the extension member is curved, whereby greater visibility of the distal end results.

22. The ultrasonic horn of claim 1, wherein the internal channel has a closed end at a location proximal to the tip lead.

23. An ultrasonic horn configured for use with a surgical ultrasonic resonator, the ultrasonic horn configured to receive ultrasonic energy and conduct the received ultrasonic energy along its length, the ultrasonic horn comprising:
an elongated member having a longitudinal centerline, a proximal end, a planar distal end, a first intermediate point disposed between the proximal end and the distal end, a second intermediate point disposed between the first intermediate point and the distal end, a third intermediate point disposed between the second intermediate point and the distal end, a fourth intermediate point disposed between the third intermediate point and the distal end, and a fifth intermediate point disposed between the fourth intermediate point and the distal end, wherein the elongated member is formed of a rigid ultrasonic energy conductive material selected such that the elongated member conducts ultrasonic energy from its proximal end to its planar distal end;
an internal channel longitudinally disposed through the elongated member and centered on the longitudinal centerline thereby forming an outer wall of the elongated member, the outer wall configured to conduct ultrasonic energy;
the elongated member having a first hollow portion having a Gaussian profile, the first hollow portion extending from the proximal end of the elongated member to the first intermediate point, the first hollow portion being centered along the longitudinal centerline forming a part of the internal channel;
the elongated member having a second hollow portion having a substantially straight constant diameter profile extending distally from the first intermediate point to the second intermediate point, the constant diameter profile corresponding to a diameter of the first hollow portion at the first intermediate point, the second hollow portion adjoining the first hollow portion and being centered along the longitudinal centerline forming a part of the internal channel;
the elongated member having a third hollow portion having a flared exponential profile extending distally from the second intermediate point to the third intermediate point, the third hollow portion adjoining the second hollow portion and being centered along the longitudinal centerline forming a part of the internal channel; and
the elongated member having a fourth hollow portion having a generally conical profile and an abraded outer surface extending distally from the third intermediate point to the fourth intermediate point, the fourth hollow portion adjoining the third hollow portion and being centered along the longitudinal centerline forming a part of the internal channel;
the elongated member having a fifth hollow portion having a generally conical profile and a substantially smooth outer surface extending distally from the fourth intermediate point to the fifth intermediate point, the fifth hollow portion adjoining the fourth hollow portion and being centered along the longitudinal centerline forming a part of the internal channel; and
the elongated member having a sixth hollow portion having a tapering profile and a substantially smooth outer surface extending distally from the fifth intermediate point to the distal end, the sixth hollow portion adjoining the fifth hollow portion and being centered along the longitudinal centerline forming a part of the internal channel;
wherein the elongated member is formed of a single piece of rigid ultrasonic conducting material with the distal end also formed thereof, and wherein the planar distal end having an exterior surface, at least a portion of which includes an abrasive structure.

24. The ultrasonic horn of claim 23, wherein the internal channel has a closed end at a location proximal to the planar distal end.

25. An ultrasonic horn configured for use with a surgical ultrasonic handpiece having a resonator, the ultrasonic horn configured to receive ultrasonic energy and conduct the received ultrasonic energy along its length, the ultrasonic horn comprising:
an elongated member having a longitudinal centerline, a proximal end, and a distal end, wherein the elongated member is formed of a single piece of rigid ultrasonic energy conductive material selected such that the elongated member conducts ultrasonic energy from its proximal end to its distal end;
the elongated member having a first hollow portion extending from the proximal end having a Gaussian profile, the first hollow portion being centered along the longitudinal centerline;
the elongated member having a second hollow portion having a straight profile, the second hollow portion being centered along the longitudinal centerline;

the elongated member having a third hollow portion comprising the distal end of the elongated member, the third hollow portion including a tip lead formed as part of the distal end and configured with an external abrasive structure devoid of sharp surfaces for removing bone, the third hollow portion being centered along the longitudinal centerline; and a continuous internal channel longitudinally disposed in the first hollow portion, the second hollow portion, and the third hollow portion, thereby forming an outer ultrasonic conducting wall of the elongated member, the outer wall conducting ultrasonic energy to the distal tip lead.

26. The ultrasonic horn of claim 25, wherein the abrasive structure includes an array of pyramid shaped protrusions aligned both transversely and linearly with respect to the longitudinal centerline of the elongated member, and a plurality of transverse grooves and longitudinal grooves with the protrusions being dull so that there are no sharp points.

27. The ultrasonic horn of claim 25, further including an extension member rigidly connected with the proximal end of the elongated member, the extension member being formed of rigid ultrasonic conducting material.

28. The ultrasonic horn of claim 27, wherein the extension member is curved, whereby greater visibility of the distal end results.

29. The ultrasonic horn of claim 25, further including an adapter connected with the elongated member, wherein the adapter is configured for connecting the elongated member with a resonator.

30. The ultrasonic horn of claim 25, further including pre-aspiration apertures formed through the elongated member at a location proximal to the tip lead and extending from the internal channel through the wall to an external surface of the elongated member.

31. An ultrasonic horn configured for use with a surgical ultrasonic resonator, the ultrasonic horn configured to receive ultrasonic energy and conduct the received ultrasonic energy along its length, the ultrasonic horn comprising:

an elongated member having a longitudinal centerline, a proximal end, a planar distal end, a first intermediate point disposed between the proximal end and the distal end, a second intermediate point disposed between the first intermediate point and the distal end, a third intermediate point disposed between the second intermediate point and the distal end, the elongated member being formed of a rigid ultrasonic conducting material;

an internal channel longitudinally disposed through the elongated member;

the elongated member having a first hollow portion having a Gaussian profile, the first hollow portion extending from the proximal end of the elongated member to the first intermediate point, the first hollow portion being centered along the longitudinal centerline with its hollow portion forming a part of the internal channel;

the elongated member having a second hollow portion having a substantially straight constant diameter profile extending distally from the first intermediate point to the second intermediate point, the constant diameter profile corresponding to a diameter of the Gaussian profile at the first intermediate point, the second hollow portion being centered along the longitudinal centerline with its hollow portion forming a part of the internal channel;

the elongated member having a third hollow portion having a flared exponential profile extending distally from the second intermediate point to the third intermediate point, the third hollow portion being centered along the longitudinal centerline with its hollow portion forming a part of the internal channel; and the elongated member having a fourth hollow portion having a generally inverse conical profile extending distally from the third intermediate point to the planar distal end of the elongated member, the fourth hollow portion including the planar distal end on which is integrally formed a tip lead of the elongated member, the tip lead having an external surface at least a portion of which is configured as an abrasive surface configured to abrade bone.

32. The ultrasonic horn of claim 31, further including an adapter having the internal channel disposed therethrough, wherein the adapter is configured distally for connection with the proximal end of the elongated member and the adapter is configured proximally for connection with a ultrasonic resonator.

33. The ultrasonic horn of claim 31, wherein the external surface of the tip lead includes an abrasive mill-file configuration covering the full external surface of the tip of the elongated member.

34. The ultrasonic horn of claim 31, wherein the external surface of the tip includes an abrasive mill-file structure covering only a portion of the external surface of the tip of the elongated member.

35. The ultrasonic horn of claim 31, further including a rigid extension member, wherein the ultrasonic horn is configured to operate at a target frequency of about 36 kHz.

36. The ultrasonic horn of claim 31, further including pre-aspiration apertures formed through the elongated member at a location proximal to the tip lead and extending from the internal channel to an external surface of the elongated member.

37. The ultrasonic horn of claim 31, wherein the ultrasonic horn is configured to operate at a target frequency of about 36 kHz.

38. The ultrasonic horn of claim 31, wherein the ultrasonic horn is configured to operate at a target frequency of about 23 kHz.

39. The ultrasonic horn of claim 31, wherein the elongated member including the tip lead is formed from a single piece of ultrasonic conducting material.

40. The ultrasonic horn of claim 39, wherein the internal channel has a closed end at a location proximal to the tip lead.

41. An ultrasonic horn configured for use with a surgical ultrasonic resonator, the ultrasonic horn configured to receive ultrasonic energy and conduct the received ultrasonic energy along its length, the ultrasonic horn comprising:

an elongated member having a longitudinal centerline, a proximal end, a generally planar distal end, a first intermediate point disposed between the proximal end and the distal end, a second intermediate point disposed between the first intermediate point and the distal end, a third intermediate point disposed between the second intermediate point and the distal end, the elongated member being formed of a single piece of rigid ultrasonic conducting material;

an internal channel disposed through the elongated member;

the elongated member having a first hollow portion having a Gaussian profile, the first hollow portion extending from the proximal end of the elongated member to the first intermediate point, the first hollow portion being centered along the longitudinal centerline with its hollow portion forming a part of the internal channel;

the elongated member having a second hollow portion having a substantially straight constant diameter profile extending distally from the first intermediate point to the second intermediate point, the constant diameter profile corresponding to a diameter of the Gaussian profile at the first intermediate point, the second hollow portion adjoining the first hollow portion and being centered along the longitudinal centerline with its hollow portion forming a part of the internal channel;

the elongated member having a third hollow portion having a flared exponential profile extending distally from the second intermediate point to the third intermediate point, the third hollow portion adjoining the second hollow portion and being centered along the longitudinal centerline with its hollow portion forming a part of the internal channel; and the elongated member having a fourth hollow portion having a conical profile and the generally planar distal end, the fourth hollow portion forming a tip lead of the elongated member, the tip lead having an abrasive mill-file external surface formed according to the conical profile, the fourth hollow portion adjoining the third hollow portion and being centered along the longitudinal centerline with its hollow portion forming a part of the internal channel.

42. The ultrasonic horn of claim 41, further including an adapter configured for connection to the elongated member with a resonator.

43. The ultrasonic horn of claim 41, further including pre-aspiration apertures formed through the elongated member at a location proximal to the tip lead and extending from the internal channel to an external surface of the elongated member.

44. The ultrasonic horn of claim 41, wherein the internal channel has a closed end at a location proximal to the tip lead.

* * * * *